United States Patent
Jefferies et al.

(10) Patent No.: US 10,058,619 B2
(45) Date of Patent: Aug. 28, 2018

(54) P97-POLYNUCLEOTIDE CONJUGATES

(71) Applicant: biOasis Technologies, Inc., Richmond (CA)

(72) Inventors: Wilfred Jefferies, Surrey (CA); Reinhard Gabathuler, Montreal (CA)

(73) Assignee: Bioasis Technologies, Inc., Guilford, CT (US)

( * ) Notice: Subject to any disclaimer, the term of this patent is extended or adjusted under 35 U.S.C. 154(b) by 0 days.

(21) Appl. No.: 15/306,978

(22) PCT Filed: May 1, 2015

(86) PCT No.: PCT/US2015/028743
§ 371 (c)(1),
(2) Date: Oct. 26, 2016

(87) PCT Pub. No.: WO2015/168521
PCT Pub. Date: Nov. 5, 2015

(65) Prior Publication Data
US 2017/0049897 A1 Feb. 23, 2017

Related U.S. Application Data

(60) Provisional application No. 62/144,598, filed on Apr. 8, 2015, provisional application No. 62/033,903, filed on (Continued)

(51) Int. Cl.
*C07K 14/47* (2006.01)
*A61K 49/00* (2006.01)
(Continued)

(52) U.S. Cl.
CPC .......... *A61K 47/483* (2013.01); *A61K 9/0019* (2013.01); *A61K 31/7088* (2013.01);
(Continued)

(58) Field of Classification Search
None
See application file for complete search history.

(56) References Cited

U.S. PATENT DOCUMENTS

| 4,391,904 A | 7/1983 | Litman et al. |
| 4,394,448 A | 7/1983 | Szoka, Jr. et al. |

(Continued)

FOREIGN PATENT DOCUMENTS

WO WO2008/118013 * 10/2008 ............. A61K 47/48

OTHER PUBLICATIONS

Karkan et al., A Unique Carrier for Delivery of Therapeutic Compounds beyond the Blood-Brain Barrier. PlosOne Jun. 2008 | vol. 3 | Issue 6 | e2469 1-14 (Year: 2008).*
(Continued)

*Primary Examiner* — Adam Weidner
*Assistant Examiner* — Aurora M Fontainhas

(57) ABSTRACT

Provided are conjugates between p97 (melanotransferrin) and polynucleotides such as small interfering RNA (siRNA) molecules, and related compositions and methods of use thereof, for instance, to facilitate delivery of polynucleotides such as siRNA molecules across the blood-brain barrier (BBB) and/or improve their tissue penetration in CNS and/or peripheral tissues, and thereby treat and/or diagnose various diseases, including those having a central nervous system (CNS) component.

13 Claims, 19 Drawing Sheets
Specification includes a Sequence Listing.

Related U.S. Application Data on Aug. 6, 2014, provisional application No. 61/987,228, filed on May 1, 2014.

(51) Int. Cl.

| | | |
|---|---|---|
| *C07K 7/06* | (2006.01) | |
| *C07K 7/08* | (2006.01) | |
| *A61K 47/48* | (2006.01) | |
| *C12N 15/113* | (2010.01) | |
| *A61K 9/00* | (2006.01) | |
| *A61K 31/7088* | (2006.01) | |
| *A61K 47/64* | (2017.01) | |

(52) U.S. Cl.
CPC .......... *A61K 47/644* (2017.08); *C12N 15/113* (2013.01); *C12N 15/1137* (2013.01); *C12N 2310/11* (2013.01); *C12N 2310/14* (2013.01); *C12N 2310/3513* (2013.01)

(56) References Cited

U.S. PATENT DOCUMENTS

| | | | |
|---|---|---|---|
| 4,399,216 A | 8/1983 | Axel et al. | |
| 4,683,195 A | 7/1987 | Mullis et al. | |
| 4,683,202 A | 7/1987 | Mullis | |
| 4,704,362 A | 11/1987 | Itakura et al. | |
| 4,766,075 A | 8/1988 | Goeddel et al. | |
| 4,784,950 A | 11/1988 | Hagen et al. | |
| 4,800,159 A | 1/1989 | Mullis et al. | |
| 4,801,542 A | 1/1989 | Murray et al. | |
| 4,866,042 A | 9/1989 | Neuwelt | |
| 4,935,349 A | 6/1990 | McKnight et al. | |
| 4,946,778 A | 8/1990 | Ladner et al. | |
| 5,091,513 A | 2/1992 | Huston et al. | |
| 5,132,405 A | 7/1992 | Huston et al. | |
| 5,186,941 A | 2/1993 | Callahan et al. | |
| 5,672,683 A | 9/1997 | Friden et al. | |
| 5,677,171 A | 10/1997 | Hudziak et al. | |
| 5,720,937 A | 2/1998 | Hudziak et al. | |
| 5,720,954 A | 2/1998 | Hudziak et al. | |
| 5,725,856 A | 3/1998 | Hudziak et al. | |
| 5,770,195 A | 6/1998 | Hudziak et al. | |
| 5,772,997 A | 6/1998 | Hudziak et al. | |
| 5,798,239 A | 8/1998 | Wilson et al. | |
| 5,844,093 A | 12/1998 | Kettleborough et al. | |
| 5,932,211 A | 8/1999 | Wilson et al. | |
| 5,962,012 A | 10/1999 | Lin et al. | |
| 5,981,194 A | 11/1999 | Jefferies et al. | |
| 6,015,557 A | 1/2000 | Tobinick et al. | |
| 6,165,464 A | 12/2000 | Hudziak et al. | |
| 6,177,077 B1 | 1/2001 | Tobinick | |
| 6,261,595 B1 | 7/2001 | Stanley et al. | |
| 6,387,371 B1 | 5/2002 | Hudziak et al. | |
| 6,399,063 B1 | 6/2002 | Hudziak et al. | |
| 6,419,934 B1 | 7/2002 | Tobinick | |
| 6,419,944 B2 | 7/2002 | Tobinick | |
| 6,455,494 B1 | 9/2002 | Jefferies et al. | |
| 6,537,549 B2 | 3/2003 | Tobinick | |
| 6,537,785 B1 | 3/2003 | Canfield | |
| 6,596,541 B2 | 7/2003 | Murphy et al. | |
| 6,765,087 B1 | 7/2004 | Casterman et al. | |
| 6,838,254 B1 | 1/2005 | Hamers et al. | |
| 6,982,089 B2 | 1/2006 | Tobinick | |
| 7,132,511 B2 | 11/2006 | Carr et al. | |
| 7,138,371 B2 | 11/2006 | DeFrees et al. | |
| 7,179,617 B2 | 2/2007 | DeFrees et al. | |
| 7,214,658 B2 | 5/2007 | Tobinick | |
| 7,244,592 B2 | 7/2007 | Hoogenboom et al. | |
| 7,247,301 B2 | 7/2007 | van de Winkel et al. | |
| 7,462,697 B2 | 12/2008 | Couto et al. | |
| 7,595,378 B2 | 9/2009 | van de Winkel et al. | |
| 7,700,554 B2 | 4/2010 | Beliveau et al. | |
| 7,723,484 B2 | 5/2010 | Beidler et al. | |
| 7,939,072 B2 | 5/2011 | Yarden et al. | |
| 7,960,516 B2 | 6/2011 | Matheus et al. | |
| 8,546,319 B2 | 10/2013 | Starr et al. | |
| 8,722,019 B2 | 5/2014 | Jeffries et al. | |
| 9,150,846 B2 | 10/2015 | Hutchison et al. | |
| 9,161,992 B2 | 10/2015 | Jefferies et al. | |
| 9,364,567 B2 | 6/2016 | Vitalis et al. | |
| 2002/0059032 A1* | 5/2002 | Camara Y. Ferrer | ...................... C12N 15/1089 702/20 |
| 2002/0119095 A1 | 8/2002 | Gabathuler et al. | |
| 2003/0072761 A1 | 4/2003 | LeBowitz | |
| 2003/0129186 A1 | 7/2003 | Beliveau et al. | |
| 2004/0055022 A1 | 3/2004 | Cheng et al. | |
| 2004/0137557 A1 | 7/2004 | DeFrees et al. | |
| 2005/0026823 A1 | 2/2005 | Zankel et al. | |
| 2005/0158296 A1 | 7/2005 | Starr et al. | |
| 2007/0167365 A1 | 7/2007 | Beliveau et al. | |
| 2008/0014188 A1 | 1/2008 | Zankel et al. | |
| 2008/0152645 A1 | 6/2008 | Pardridge et al. | |
| 2009/0226421 A1 | 9/2009 | Parren et al. | |
| 2010/0129359 A1 | 5/2010 | Tobinick | |
| 2010/0183581 A1 | 7/2010 | Beliveau et al. | |
| 2010/0297120 A1 | 11/2010 | Beliveau et al. | |
| 2010/0303797 A1 | 12/2010 | Starr et al. | |
| 2011/0093962 A1 | 4/2011 | Heidbrink et al. | |
| 2011/0142763 A1 | 6/2011 | Zankel et al. | |
| 2011/0318323 A1 | 12/2011 | Zhu et al. | |
| 2012/0003202 A1 | 1/2012 | Calias et al. | |
| 2012/0107302 A1 | 5/2012 | Berry et al. | |
| 2013/0108548 A1 | 5/2013 | Vlieghe et al. | |
| 2013/0183368 A1 | 7/2013 | Hutchison et al. | |
| 2013/0236442 A1 | 9/2013 | Lee et al. | |
| 2014/0105880 A1 | 4/2014 | Starr et al. | |
| 2014/0178350 A1 | 6/2014 | Vitalis et al. | |
| 2014/0322132 A1 | 10/2014 | Vitalis et al. | |
| 2015/0056218 A1 | 2/2015 | Jefferies et al. | |
| 2015/0093399 A1 | 4/2015 | Jefferies | |
| 2016/0053237 A1 | 2/2016 | Jefferies et al. | |
| 2016/0324937 A1 | 11/2016 | Vitalis et al. | |
| 2016/0347821 A1 | 12/2016 | Vitalis et al. | |
| 2017/0204386 A1 | 7/2017 | Vitalis et al. | |

OTHER PUBLICATIONS

Altenhofer et al., The NOX toolbox: validating the role of NADPH oxidases in physiology and disease. Cell. Mol. Life Sci. (2012) 69: 2327-2343 (Year: 2012).*

Gabathuler, Reinhard; "A natural solution to deliver medicine to brain"; Poster presented at the Drug Delivery & Formulation Summit; Apr. 2015; retrieved from http://www.ddfsummit.com/wp-content/uploads/2015/04/Reinhard-Gabathuler.pdf on Mar. 15, 2018.

* cited by examiner

A

B

SEQUENCE LISTING

<160> NUMBER OF SEQ ID NOS: 59

<210> SEQ ID NO 1
<211> LENGTH: 738
<212> TYPE: PRT
<213> ORGANISM: Homo sapiens

<400> SEQUENCE: 1

```
Met Arg Gly Pro Ser Gly Ala Leu Trp Leu Leu Leu Ala Leu Arg Thr
1               5                   10                  15

Val Leu Gly Gly Met Glu Val Arg Trp Cys Ala Thr Ser Asp Pro Glu
            20                  25                  30

Gln His Lys Cys Gly Asn Met Ser Glu Ala Phe Arg Glu Ala Gly Ile
        35                  40                  45

Gln Pro Ser Leu Leu Cys Val Arg Gly Thr Ser Ala Asp His Cys Val
    50                  55                  60

Gln Leu Ile Ala Ala Gln Glu Ala Asp Ala Ile Thr Leu Asp Gly Gly
65                  70                  75                  80

Ala Ile Tyr Glu Ala Gly Lys Glu His Gly Leu Lys Pro Val Val Gly
                85                  90                  95

Glu Val Tyr Asp Gln Glu Val Gly Thr Ser Tyr Tyr Ala Val Ala Val
            100                 105                 110

Val Arg Arg Ser Ser His Val Thr Ile Asp Thr Leu Lys Gly Val Lys
        115                 120                 125

Ser Cys His Thr Gly Ile Asn Arg Thr Val Gly Trp Asn Val Pro Val
    130                 135                 140

Gly Tyr Leu Val Glu Ser Gly Arg Leu Ser Val Met Gly Cys Asp Val
145                 150                 155                 160

Leu Lys Ala Val Ser Asp Tyr Phe Gly Gly Ser Cys Val Pro Gly Ala
                165                 170                 175

Gly Glu Thr Ser Tyr Ser Glu Ser Leu Cys Arg Leu Cys Arg Gly Asp
            180                 185                 190

Ser Ser Gly Glu Gly Val Cys Asp Lys Ser Pro Leu Glu Arg Tyr Tyr
        195                 200                 205

Asp Tyr Ser Gly Ala Phe Arg Cys Leu Ala Glu Gly Ala Gly Asp Val
    210                 215                 220

Ala Phe Val Lys His Ser Thr Val Leu Glu Asn Thr Asp Gly Lys Thr
225                 230                 235                 240

Leu Pro Ser Trp Gly Gln Ala Leu Leu Ser Gln Asp Phe Glu Leu Leu
                245                 250                 255
```

```
Cys Arg Asp Gly Ser Arg Ala Asp Val Thr Glu Trp Arg Gln Cys His
            260                 265                 270

Leu Ala Arg Val Pro Ala His Ala Val Val Arg Ala Asp Thr Asp
        275                 280                 285

Gly Gly Leu Ile Phe Arg Leu Leu Asn Glu Gly Gln Arg Leu Phe Ser
290                 295                 300

His Glu Gly Ser Ser Phe Gln Met Phe Ser Ser Glu Ala Tyr Gly Gln
305                 310                 315                 320

Lys Asp Leu Leu Phe Lys Asp Ser Thr Ser Glu Leu Val Pro Ile Ala
                325                 330                 335

Thr Gln Thr Tyr Glu Ala Trp Leu Gly His Glu Tyr Leu His Ala Met
            340                 345                 350

Lys Gly Leu Leu Cys Asp Pro Asn Arg Leu Pro Pro Tyr Leu Arg Trp
        355                 360                 365

Cys Val Leu Ser Thr Pro Glu Ile Gln Lys Cys Gly Asp Met Ala Val
370                 375                 380

Ala Phe Arg Arg Gln Arg Leu Lys Pro Glu Ile Gln Cys Val Ser Ala
385                 390                 395                 400

Lys Ser Pro Gln His Cys Met Glu Arg Ile Gln Ala Glu Gln Val Asp
                405                 410                 415

Ala Val Thr Leu Ser Gly Glu Asp Ile Tyr Thr Ala Gly Lys Thr Tyr
            420                 425                 430

Gly Leu Val Pro Ala Ala Gly Glu His Tyr Ala Pro Glu Asp Ser Ser
        435                 440                 445

Asn Ser Tyr Tyr Val Val Ala Val Val Arg Arg Asp Ser Ser His Ala
450                 455                 460

Phe Thr Leu Asp Glu Leu Arg Gly Lys Arg Ser Cys His Ala Gly Phe
465                 470                 475                 480

Gly Ser Pro Ala Gly Trp Asp Val Pro Val Gly Ala Leu Ile Gln Arg
                485                 490                 495

Gly Phe Ile Arg Pro Lys Asp Cys Asp Val Leu Thr Ala Val Ser Glu
            500                 505                 510

Phe Phe Asn Ala Ser Cys Val Pro Val Asn Asn Pro Lys Asn Tyr Pro
        515                 520                 525

Ser Ser Leu Cys Ala Leu Cys Val Gly Asp Glu Gln Gly Arg Asn Lys
530                 535                 540

Cys Val Gly Asn Ser Gln Glu Arg Tyr Tyr Gly Tyr Arg Gly Ala Phe
545                 550                 555                 560

Arg Cys Leu Val Glu Asn Ala Gly Asp Val Ala Phe Val Arg His Thr
                565                 570                 575

Thr Val Phe Asp Asn Thr Asn Gly His Asn Ser Glu Pro Trp Ala Ala
            580                 585                 590

Glu Leu Arg Ser Glu Asp Tyr Glu Leu Leu Cys Pro Asn Gly Ala Arg
        595                 600                 605

Ala Glu Val Ser Gln Phe Ala Ala Cys Asn Leu Ala Gln Ile Pro Pro
610                 615                 620

His Ala Val Met Val Arg Pro Asp Thr Asn Ile Phe Thr Val Tyr Gly
625                 630                 635                 640

Leu Leu Asp Lys Ala Gln Asp Leu Phe Gly Asp His Asn Lys Asn
                645                 650                 655

Gly Phe Lys Met Phe Asp Ser Ser Asn Tyr His Gly Gln Asp Leu Leu
            660                 665                 670

Phe Lys Asp Ala Thr Val Arg Ala Val Pro Val Gly Glu Lys Thr Thr
```

```
                675                 680                 685
Tyr Arg Gly Trp Leu Gly Leu Asp Tyr Val Ala Ala Leu Glu Gly Met
    690                 695                 700

Ser Ser Gln Gln Cys Ser Gly Ala Ala Ala Pro Ala Pro Gly Ala Pro
705                 710                 715                 720

Leu Leu Pro Leu Leu Leu Pro Ala Leu Ala Ala Arg Leu Leu Pro Pro
                725                 730                 735

Ala Leu

<210> SEQ ID NO 2
<211> LENGTH: 692
<212> TYPE: PRT
<213> ORGANISM: Homo sapiens

<400> SEQUENCE: 2

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
                20                  25                  30

Leu Leu Cys Val Arg Gly Thr Ser Ala Asp His Cys Val Gln Leu Ile
            35                  40                  45

Ala Ala Gln Glu Ala Asp Ala Ile Thr Leu Asp Gly Gly Ala Ile Tyr
        50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
                100                 105                 110

Thr Gly Ile Asn Arg Thr Val Gly Trp Asn Val Pro Val Gly Tyr Leu
            115                 120                 125

Val Glu Ser Gly Arg Leu Ser Val Met Gly Cys Asp Val Leu Lys Ala
        130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
                180                 185                 190

Gly Ala Phe Arg Cys Leu Ala Glu Gly Ala Gly Asp Val Ala Phe Val
            195                 200                 205

Lys His Ser Thr Val Leu Glu Asn Thr Asp Gly Lys Thr Leu Pro Ser
        210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
                260                 265                 270

Ile Phe Arg Leu Leu Asn Glu Gly Gln Arg Leu Phe Ser His Glu Gly
            275                 280                 285

Ser Ser Phe Gln Met Phe Ser Ser Glu Ala Tyr Gly Gln Lys Asp Leu
        290                 295                 300

Leu Phe Lys Asp Ser Thr Ser Glu Leu Val Pro Ile Ala Thr Gln Thr
```

-continued

```
            305                 310                 315                 320
        Tyr Glu Ala Trp Leu Gly His Glu Tyr Leu His Ala Met Lys Gly Leu
                        325                 330                 335
        Leu Cys Asp Pro Asn Arg Leu Pro Pro Tyr Leu Arg Trp Cys Val Leu
                        340                 345                 350
        Ser Thr Pro Glu Ile Gln Lys Cys Gly Asp Met Ala Val Ala Phe Arg
                        355                 360                 365
        Arg Gln Arg Leu Lys Pro Glu Ile Gln Cys Val Ser Ala Lys Ser Pro
                370                 375                 380
        Gln His Cys Met Glu Arg Ile Gln Ala Glu Gln Val Asp Ala Val Thr
        385                 390                 395                 400
        Leu Ser Gly Glu Asp Ile Tyr Thr Ala Gly Lys Thr Tyr Gly Leu Val
                        405                 410                 415
        Pro Ala Ala Gly Glu His Tyr Ala Pro Glu Asp Ser Ser Asn Ser Tyr
                        420                 425                 430
        Tyr Val Val Ala Val Val Arg Arg Asp Ser Ser His Ala Phe Thr Leu
                        435                 440                 445
        Asp Glu Leu Arg Gly Lys Arg Ser Cys His Ala Gly Phe Gly Ser Pro
                450                 455                 460
        Ala Gly Trp Asp Val Pro Val Gly Ala Leu Ile Gln Arg Gly Phe Ile
        465                 470                 475                 480
        Arg Pro Lys Asp Cys Asp Val Leu Thr Ala Val Ser Glu Phe Phe Asn
                        485                 490                 495
        Ala Ser Cys Val Pro Val Asn Asn Pro Lys Asn Tyr Pro Ser Ser Leu
                        500                 505                 510
        Cys Ala Leu Cys Val Gly Asp Glu Gln Gly Arg Asn Lys Cys Val Gly
                        515                 520                 525
        Asn Ser Gln Glu Arg Tyr Tyr Gly Tyr Arg Gly Ala Phe Arg Cys Leu
                530                 535                 540
        Val Glu Asn Ala Gly Asp Val Ala Phe Val Arg His Thr Thr Val Phe
        545                 550                 555                 560
        Asp Asn Thr Asn Gly His Asn Ser Glu Pro Trp Ala Ala Glu Leu Arg
                        565                 570                 575
        Ser Glu Asp Tyr Glu Leu Leu Cys Pro Asn Gly Ala Arg Ala Glu Val
                        580                 585                 590
        Ser Gln Phe Ala Ala Cys Asn Leu Ala Gln Ile Pro Pro His Ala Val
                        595                 600                 605
        Met Val Arg Pro Asp Thr Asn Ile Phe Thr Val Tyr Gly Leu Leu Asp
                610                 615                 620
        Lys Ala Gln Asp Leu Phe Gly Asp Asp His Asn Lys Asn Gly Phe Lys
        625                 630                 635                 640
        Met Phe Asp Ser Ser Asn Tyr His Gly Gln Asp Leu Leu Phe Lys Asp
                        645                 650                 655
        Ala Thr Val Arg Ala Val Pro Val Gly Glu Lys Thr Thr Tyr Arg Gly
                        660                 665                 670
        Trp Leu Gly Leu Asp Tyr Val Ala Ala Leu Glu Gly Met Ser Ser Gln
                        675                 680                 685
        Gln Cys Ser Gly
                690

<210> SEQ ID NO 3
<211> LENGTH: 11
<212> TYPE: PRT
<213> ORGANISM: Homo sapiens
```

```
<400> SEQUENCE: 3

Trp Cys Ala Thr Ser Asp Pro Glu Gln His Lys
1               5                   10

<210> SEQ ID NO 4
<211> LENGTH: 11
<212> TYPE: PRT
<213> ORGANISM: Homo sapiens

<400> SEQUENCE: 4

Arg Ser Ser His Val Thr Ile Asp Thr Leu Lys
1               5                   10

<210> SEQ ID NO 5
<211> LENGTH: 13
<212> TYPE: PRT
<213> ORGANISM: Homo sapiens

<400> SEQUENCE: 5

Ser Ser His Val Thr Ile Asp Thr Leu Lys Gly Val Lys
1               5                   10

<210> SEQ ID NO 6
<211> LENGTH: 14
<212> TYPE: PRT
<213> ORGANISM: Homo sapiens

<400> SEQUENCE: 6

Leu Cys Arg Gly Asp Ser Ser Gly Glu Gly Val Cys Asp Lys
1               5                   10

<210> SEQ ID NO 7
<211> LENGTH: 16
<212> TYPE: PRT
<213> ORGANISM: Homo sapiens

<400> SEQUENCE: 7

Gly Asp Ser Ser Gly Glu Gly Val Cys Asp Lys Ser Pro Leu Glu Arg
1               5                   10                  15

<210> SEQ ID NO 8
<211> LENGTH: 9
<212> TYPE: PRT
<213> ORGANISM: Homo sapiens

<400> SEQUENCE: 8

Tyr Tyr Asp Tyr Ser Gly Ala Phe Arg
1               5

<210> SEQ ID NO 9
<211> LENGTH: 7
<212> TYPE: PRT
<213> ORGANISM: Homo sapiens

<400> SEQUENCE: 9

Ala Asp Val Thr Glu Trp Arg
1               5

<210> SEQ ID NO 10
<211> LENGTH: 9
<212> TYPE: PRT
<213> ORGANISM: Homo sapiens

<400> SEQUENCE: 10
```

```
Val Pro Ala His Ala Val Val Val Arg
1               5
```

<210> SEQ ID NO 11
<211> LENGTH: 10
<212> TYPE: PRT
<213> ORGANISM: Homo sapiens

<400> SEQUENCE: 11

```
Ala Asp Thr Asp Gly Gly Leu Ile Phe Arg
1               5                   10
```

<210> SEQ ID NO 12
<211> LENGTH: 9
<212> TYPE: PRT
<213> ORGANISM: Homo sapiens

<400> SEQUENCE: 12

```
Cys Gly Asp Met Ala Val Ala Phe Arg
1               5
```

<210> SEQ ID NO 13
<211> LENGTH: 11
<212> TYPE: PRT
<213> ORGANISM: Homo sapiens

<400> SEQUENCE: 13

```
Leu Lys Pro Glu Ile Gln Cys Val Ser Ala Lys
1               5                   10
```

<210> SEQ ID NO 14
<211> LENGTH: 12
<212> TYPE: PRT
<213> ORGANISM: Homo sapiens

<400> SEQUENCE: 14

```
Asp Ser Ser His Ala Phe Thr Leu Asp Glu Leu Arg
1               5                   10
```

<210> SEQ ID NO 15
<211> LENGTH: 13
<212> TYPE: PRT
<213> ORGANISM: Homo sapiens

<400> SEQUENCE: 15

```
Ser Glu Asp Tyr Glu Leu Leu Cys Pro Asn Gly Ala Arg
1               5                   10
```

<210> SEQ ID NO 16
<211> LENGTH: 15
<212> TYPE: PRT
<213> ORGANISM: Homo sapiens

<400> SEQUENCE: 16

```
Ala Gln Asp Leu Phe Gly Asp Asp His Asn Lys Asn Gly Phe Lys
1               5                   10                  15
```

<210> SEQ ID NO 17
<211> LENGTH: 40
<212> TYPE: PRT
<213> ORGANISM: Homo sapiens

<400> SEQUENCE: 17

```
Phe Ser Ser Glu Ala Tyr Gly Gln Lys Asp Leu Leu Phe Lys Asp Ser
```

```
                1               5                  10                 15
            Thr Ser Glu Leu Val Pro Ile Ala Thr Gln Thr Tyr Glu Ala Trp Leu
                            20                  25                 30
            Gly His Glu Tyr Leu His Ala Met
                            35                  40
```

<210> SEQ ID NO 18
<211> LENGTH: 221
<212> TYPE: PRT
<213> ORGANISM: Homo sapiens

<400> SEQUENCE: 18

```
Glu Arg Ile Gln Ala Glu Gln Val Asp Ala Val Thr Leu Ser Gly Glu
1               5                  10                 15
Asp Ile Tyr Thr Ala Gly Lys Thr Tyr Gly Leu Val Pro Ala Ala Gly
                20                  25                 30
Glu His Tyr Ala Pro Glu Asp Ser Ser Asn Ser Tyr Tyr Val Val Ala
                35                  40                 45
Val Val Arg Arg Asp Ser Ser His Ala Phe Thr Leu Asp Glu Leu Arg
    50                  55                  60
Gly Lys Arg Ser Cys His Ala Gly Phe Gly Ser Pro Ala Gly Trp Asp
65                  70                  75                 80
Val Pro Val Gly Ala Leu Ile Gln Arg Gly Phe Ile Arg Pro Lys Asp
                85                  90                 95
Cys Asp Val Leu Thr Ala Val Ser Glu Phe Phe Asn Ala Ser Cys Val
                100                 105                110
Pro Val Asn Asn Pro Lys Asn Tyr Pro Ser Ser Leu Cys Ala Leu Cys
                115                 120                125
Val Gly Asp Glu Gln Gly Arg Asn Lys Cys Val Gly Asn Ser Gln Glu
                130                 135                140
Arg Tyr Tyr Gly Tyr Arg Gly Ala Phe Arg Cys Leu Val Glu Asn Ala
145                 150                 155                160
Gly Asp Val Ala Phe Val Arg His Thr Thr Val Phe Asp Asn Thr Asn
                165                 170                175
Gly His Asn Ser Glu Pro Trp Ala Ala Glu Leu Arg Ser Glu Asp Tyr
                180                 185                190
Glu Leu Leu Cys Pro Asn Gly Ala Arg Ala Glu Val Ser Gln Phe Ala
                195                 200                205
Ala Cys Asn Leu Ala Gln Ile Pro Pro His Ala Val Met
                210                 215                220
```

<210> SEQ ID NO 19
<211> LENGTH: 32
<212> TYPE: PRT
<213> ORGANISM: Homo sapiens

<400> SEQUENCE: 19

```
Val Arg Pro Asp Thr Asn Ile Phe Thr Val Tyr Gly Leu Leu Asp Lys
1               5                  10                 15
Ala Gln Asp Leu Phe Gly Asp Asp His Asn Lys Asn Gly Phe Lys Met
                20                  25                 30
```

<210> SEQ ID NO 20
<211> LENGTH: 564
<212> TYPE: PRT
<213> ORGANISM: Homo sapiens

<400> SEQUENCE: 20

```
Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
        355                 360                 365

Arg Gln Arg Leu Lys Pro Glu Ile Gln Cys Val Ser Ala Lys Ser Pro
370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415
```

```
Pro Ala Ala Gly Glu His Tyr Ala Pro Glu Asp Ser Ser Asn Ser Tyr
            420                 425                 430

Tyr Val Ala Val Val Arg Arg Asp Ser Ser His Ala Phe Thr Leu
        435                 440                 445

Asp Glu Leu Arg Gly Lys Arg Ser Cys His Ala Gly Phe Gly Ser Pro
    450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
            530                 535                 540

Val Glu Asn Ala Gly Asp Val Ala Phe Val Arg His Thr Thr Val Phe
545                 550                 555                 560

Asp Asn Thr Asn

<210> SEQ ID NO 21
<211> LENGTH: 22
<212> TYPE: PRT
<213> ORGANISM: Homo sapiens

<400> SEQUENCE: 21

Gly His Asn Ser Glu Pro Trp Ala Ala Glu Leu Arg Ser Glu Asp Tyr
1               5                   10                  15

Glu Leu Leu Cys Pro Asn
            20

<210> SEQ ID NO 22
<211> LENGTH: 51
<212> TYPE: PRT
<213> ORGANISM: Homo sapiens

<400> SEQUENCE: 22

Gly Ala Arg Ala Glu Val Ser Gln Phe Ala Ala Cys Asn Leu Ala Gln
1               5                   10                  15

Ile Pro Pro His Ala Val Met Val Arg Pro Asp Thr Asn Ile Phe Thr
            20                  25                  30

Val Tyr Gly Leu Leu Asp Lys Ala Gln Asp Leu Phe Gly Asp Asp His
        35                  40                  45

Asn Lys Asn
    50

<210> SEQ ID NO 23
<211> LENGTH: 53
<212> TYPE: PRT
<213> ORGANISM: Homo sapiens

<400> SEQUENCE: 23

Gly Phe Lys Met Phe Asp Ser Ser Asn Tyr His Gly Gln Asp Leu Leu
1               5                   10                  15

Phe Lys Asp Ala Thr Val Arg Ala Val Pro Val Gly Glu Lys Thr Thr
            20                  25                  30

Tyr Arg Gly Trp Leu Gly Leu Asp Tyr Val Ala Ala Leu Glu Gly Met
        35                  40                  45
```

Ser Ser Gln Gln Cys
    50

<210> SEQ ID NO 24
<211> LENGTH: 586
<212> TYPE: PRT
<213> ORGANISM: Homo sapiens

<400> SEQUENCE: 24

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
            20                  25                  30

Leu Leu Cys Val Arg Gly Thr Ser Ala Asp His Cys Val Gln Leu Ile
        35                  40                  45

Ala Ala Gln Glu Ala Asp Ala Ile Thr Leu Asp Gly Gly Ala Ile Tyr
    50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
            100                 105                 110

Thr Gly Ile Asn Arg Thr Val Gly Trp Asn Val Pro Val Gly Tyr Leu
        115                 120                 125

Val Glu Ser Gly Arg Leu Ser Val Met Gly Cys Asp Val Leu Lys Ala
    130                 135                 140

Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg

```
            355                 360                 365
Arg Gln Arg Leu Lys Pro Glu Ile Gln Cys Val Ser Ala Lys Ser Pro
            370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Lys Thr Tyr Gly Leu Val
                    405                 410                 415

Pro Ala Ala Gly Glu His Tyr Ala Pro Glu Asp Ser Ser Asn Ser Tyr
                420                 425                 430

Tyr Val Val Ala Val Arg Arg Asp Ser Ser His Ala Phe Thr Leu
            435                 440                 445

Asp Glu Leu Arg Gly Lys Arg Ser Cys His Ala Gly Phe Gly Ser Pro
            450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Asn
                    485                 490                 495

Ala Ser Cys Val Pro Val Asn Asn Pro Lys Asn Tyr Pro Ser Ser Leu
                500                 505                 510

Cys Ala Leu Cys Val Gly Asp Glu Gln Gly Arg Asn Lys Cys Val Gly
            515                 520                 525

Asn Ser Gln Glu Arg Tyr Tyr Gly Tyr Arg Gly Ala Phe Arg Cys Leu
            530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
                    565                 570                 575

Ser Glu Asp Tyr Glu Leu Leu Cys Pro Asn
                580                 585

<210> SEQ ID NO 25
<211> LENGTH: 637
<212> TYPE: PRT
<213> ORGANISM: Homo sapiens

<400> SEQUENCE: 25

Gly Met Glu Val Arg Trp Cys Ala Thr Ser Asp Pro Glu Gln His Lys
1               5                   10                  15

Cys Gly Asn Met Ser Glu Ala Phe Arg Glu Ala Gly Ile Gln Pro Ser
                20                  25                  30

Leu Leu Cys Val Arg Gly Thr Ser Ala Asp His Cys Val Gln Leu Ile
            35                  40                  45

Ala Ala Gln Glu Ala Asp Ala Ile Thr Leu Asp Gly Gly Ala Ile Tyr
        50                  55                  60

Glu Ala Gly Lys Glu His Gly Leu Lys Pro Val Val Gly Glu Val Tyr
65                  70                  75                  80

Asp Gln Glu Val Gly Thr Ser Tyr Tyr Ala Val Ala Val Val Arg Arg
                85                  90                  95

Ser Ser His Val Thr Ile Asp Thr Leu Lys Gly Val Lys Ser Cys His
                100                 105                 110

Thr Gly Ile Asn Arg Thr Val Gly Trp Asn Val Pro Val Gly Tyr Leu
            115                 120                 125

Val Glu Ser Gly Arg Leu Ser Val Met Gly Cys Asp Val Leu Lys Ala
        130                 135                 140
```

```
Val Ser Asp Tyr Phe Gly Gly Ser Cys Val Pro Gly Ala Gly Glu Thr
145                 150                 155                 160

Ser Tyr Ser Glu Ser Leu Cys Arg Leu Cys Arg Gly Asp Ser Ser Gly
                165                 170                 175

Glu Gly Val Cys Asp Lys Ser Pro Leu Glu Arg Tyr Tyr Asp Tyr Ser
            180                 185                 190

Gly Ala Phe Arg Cys Leu Ala Glu Gly Ala Gly Asp Val Ala Phe Val
        195                 200                 205

Lys His Ser Thr Val Leu Glu Asn Thr Asp Gly Lys Thr Leu Pro Ser
    210                 215                 220

Trp Gly Gln Ala Leu Leu Ser Gln Asp Phe Glu Leu Leu Cys Arg Asp
225                 230                 235                 240

Gly Ser Arg Ala Asp Val Thr Glu Trp Arg Gln Cys His Leu Ala Arg
                245                 250                 255

Val Pro Ala His Ala Val Val Arg Ala Asp Thr Asp Gly Gly Leu
            260                 265                 270

Ile Phe Arg Leu Leu Asn Glu Gly Gln Arg Leu Phe Ser His Glu Gly
        275                 280                 285

Ser Ser Phe Gln Met Phe Ser Ser Glu Ala Tyr Gly Gln Lys Asp Leu
    290                 295                 300

Leu Phe Lys Asp Ser Thr Ser Glu Leu Val Pro Ile Ala Thr Gln Thr
305                 310                 315                 320

Tyr Glu Ala Trp Leu Gly His Glu Tyr Leu His Ala Met Lys Gly Leu
                325                 330                 335

Leu Cys Asp Pro Asn Arg Leu Pro Pro Tyr Leu Arg Trp Cys Val Leu
            340                 345                 350

Ser Thr Pro Glu Ile Gln Lys Cys Gly Asp Met Ala Val Ala Phe Arg
        355                 360                 365

Arg Gln Arg Leu Lys Pro Glu Ile Gln Cys Val Ser Ala Lys Ser Pro
    370                 375                 380

Gln His Cys Met Glu Arg Ile Gln Ala Glu Gln Val Asp Ala Val Thr
385                 390                 395                 400

Leu Ser Gly Glu Asp Ile Tyr Thr Ala Gly Lys Thr Tyr Gly Leu Val
                405                 410                 415

Pro Ala Ala Gly Glu His Tyr Ala Pro Glu Asp Ser Ser Asn Ser Tyr
            420                 425                 430

Tyr Val Val Ala Val Val Arg Arg Asp Ser Ser His Ala Phe Thr Leu
        435                 440                 445

Asp Glu Leu Arg Gly Lys Arg Ser Cys His Ala Gly Phe Gly Ser Pro
    450                 455                 460

Ala Gly Trp Asp Val Pro Val Gly Ala Leu Ile Gln Arg Gly Phe Ile
465                 470                 475                 480

Arg Pro Lys Asp Cys Asp Val Leu Thr Ala Val Ser Glu Phe Phe Asn
                485                 490                 495

Ala Ser Cys Val Pro Val Asn Asn Pro Lys Asn Tyr Pro Ser Ser Leu
            500                 505                 510

Cys Ala Leu Cys Val Gly Asp Glu Gln Gly Arg Asn Lys Cys Val Gly
        515                 520                 525

Asn Ser Gln Glu Arg Tyr Tyr Gly Tyr Arg Gly Ala Phe Arg Cys Leu
    530                 535                 540

Val Glu Asn Ala Gly Asp Val Ala Phe Val Arg His Thr Thr Val Phe
545                 550                 555                 560

Asp Asn Thr Asn Gly His Asn Ser Glu Pro Trp Ala Ala Glu Leu Arg
```

565                 570                 575

Ser Glu Asp Tyr Glu Leu Leu Cys Pro Asn Gly Ala Arg Ala Glu Val
            580                 585                 590

Ser Gln Phe Ala Ala Cys Asn Leu Ala Gln Ile Pro Pro His Ala Val
            595                 600                 605

Met Val Arg Pro Asp Thr Asn Ile Phe Thr Val Tyr Gly Leu Leu Asp
610                 615                 620

Lys Ala Gln Asp Leu Phe Gly Asp Asp His Asn Lys Asn
625                 630                 635

<210> SEQ ID NO 26
<211> LENGTH: 73
<212> TYPE: PRT
<213> ORGANISM: Homo sapiens

<400> SEQUENCE: 26

Gly His Asn Ser Glu Pro Trp Ala Ala Glu Leu Arg Ser Glu Asp Tyr
1               5                   10                  15

Glu Leu Leu Cys Pro Asn Gly Ala Arg Ala Glu Val Ser Gln Phe Ala
            20                  25                  30

Ala Cys Asn Leu Ala Gln Ile Pro Pro His Ala Val Met Val Arg Pro
        35                  40                  45

Asp Thr Asn Ile Phe Thr Val Tyr Gly Leu Leu Asp Lys Ala Gln Asp
    50                  55                  60

Leu Phe Gly Asp Asp His Asn Lys Asn
65                  70

<210> SEQ ID NO 27
<211> LENGTH: 126
<212> TYPE: PRT
<213> ORGANISM: Homo sapiens

<400> SEQUENCE: 27

Gly His Asn Ser Glu Pro Trp Ala Ala Glu Leu Arg Ser Glu Asp Tyr
1               5                   10                  15

Glu Leu Leu Cys Pro Asn Gly Ala Arg Ala Glu Val Ser Gln Phe Ala
            20                  25                  30

Ala Cys Asn Leu Ala Gln Ile Pro Pro His Ala Val Met Val Arg Pro
        35                  40                  45

Asp Thr Asn Ile Phe Thr Val Tyr Gly Leu Leu Asp Lys Ala Gln Asp
    50                  55                  60

Leu Phe Gly Asp Asp His Asn Lys Asn Gly Phe Lys Met Phe Asp Ser
65                  70                  75                  80

Ser Asn Tyr His Gly Gln Asp Leu Leu Phe Lys Asp Ala Thr Val Arg
                85                  90                  95

Ala Val Pro Val Gly Glu Lys Thr Thr Tyr Arg Gly Trp Leu Gly Leu
            100                 105                 110

Asp Tyr Val Ala Ala Leu Glu Gly Met Ser Ser Gln Gln Cys
        115                 120                 125

<210> SEQ ID NO 28
<211> LENGTH: 104
<212> TYPE: PRT
<213> ORGANISM: Homo sapiens

<400> SEQUENCE: 28

Gly Ala Arg Ala Glu Val Ser Gln Phe Ala Ala Cys Asn Leu Ala Gln
1               5                   10                  15

```
Ile Pro Pro His Ala Val Met Val Arg Pro Asp Thr Asn Ile Phe Thr
            20                  25                  30

Val Tyr Gly Leu Leu Asp Lys Ala Gln Asp Leu Phe Gly Asp Asp His
        35                  40                  45

Asn Lys Asn Gly Phe Lys Met Phe Asp Ser Ser Asn Tyr His Gly Gln
 50                  55                  60

Asp Leu Leu Phe Lys Asp Ala Thr Val Arg Ala Val Pro Val Gly Glu
65                  70                  75                  80

Lys Thr Thr Tyr Arg Gly Trp Leu Gly Leu Asp Tyr Val Ala Ala Leu
                85                  90                  95

Glu Gly Met Ser Ser Gln Gln Cys
            100

<210> SEQ ID NO 29
<211> LENGTH: 14
<212> TYPE: PRT
<213> ORGANISM: Artificial Sequence
<220> FEATURE:
<223> OTHER INFORMATION: Modified p97 protein fragment

<400> SEQUENCE: 29

Asp Ser Ser His Ala Phe Thr Leu Asp Glu Leu Arg Tyr Cys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Modified p97 protein fragment

<400> SEQUENCE: 30

Asp Ser Ser His Ala Phe Thr Leu Asp Glu Leu Arg Cys
1               5                   10

<210> SEQ ID NO 31
<211> LENGTH: 21
<212> TYPE: DNA
<213> ORGANISM: Artificial Sequence
<220> FEATURE:
<223> OTHER INFORMATION: Antisense NOX4 polynucleotide (siRNA)

<400> SEQUENCE: 31
auguucacaa agucaggguct t                                          21

<210> SEQ ID NO 32
<211> LENGTH: 21
<212> TYPE: DNA
<213> ORGANISM: Artificial Sequence
<220> FEATURE:
<223> OTHER INFORMATION: Antisense NOX4 polynucleotide (siRNA)

<400> SEQUENCE: 32
gaccugacuu ugugaacaut t                                           21

<210> SEQ ID NO 33
<211> LENGTH: 12
<212> TYPE: PRT
<213> ORGANISM: Jaculus jaculus

<400> SEQUENCE: 33

Asp Ser Ser Asp Ala Phe Thr Leu Asp Glu Leu Arg
1               5                   10
```

```
<210> SEQ ID NO 34
<211> LENGTH: 12
<212> TYPE: PRT
<213> ORGANISM: Otolemur garnettii

<400> SEQUENCE: 34

Asp Ser Ser His Ser Phe Thr Leu Asp Glu Leu Arg
1               5                   10

<210> SEQ ID NO 35
<211> LENGTH: 12
<212> TYPE: PRT
<213> ORGANISM: Ictidomys tridecemlineatus

<400> SEQUENCE: 35

Asp Ser Ser Tyr Ala Phe Thr Leu Asp Glu Leu Arg
1               5                   10

<210> SEQ ID NO 36
<211> LENGTH: 12
<212> TYPE: PRT
<213> ORGANISM: Ceratotherium simum simum

<400> SEQUENCE: 36

Asn Ser Ser His Ala Phe Thr Leu Asp Glu Leu Arg
1               5                   10

<210> SEQ ID NO 37
<211> LENGTH: 12
<212> TYPE: PRT
<213> ORGANISM: Vicugna pacos

<400> SEQUENCE: 37

Asn Ser Ser Tyr Ala Phe Thr Leu Asp Glu Leu Arg
1               5                   10

<210> SEQ ID NO 38
<211> LENGTH: 12
<212> TYPE: PRT
<213> ORGANISM: Ochotona princeps

<400> SEQUENCE: 38

Asp Ser Ser Tyr Ala Phe Pro Leu Asp Glu Leu Arg
1               5                   10

<210> SEQ ID NO 39
<211> LENGTH: 12
<212> TYPE: PRT
<213> ORGANISM: Tupaia chinensis

<400> SEQUENCE: 39

Asp Ser Thr His Ala Phe Thr Val Asp Glu Leu Arg
1               5                   10

<210> SEQ ID NO 40
<211> LENGTH: 12
<212> TYPE: PRT
<213> ORGANISM: Mus musculus

<400> SEQUENCE: 40

Asp Ser Ser Tyr Ser Phe Thr Leu Asp Glu Leu Arg
1               5                   10
```

<210> SEQ ID NO 41
<211> LENGTH: 12
<212> TYPE: PRT
<213> ORGANISM: Orcinus orca

<400> SEQUENCE: 41

Asn Ser Ser Asn Ala Phe Thr Leu Asp Glu Leu Arg
1               5                   10

<210> SEQ ID NO 42
<211> LENGTH: 12
<212> TYPE: PRT
<213> ORGANISM: Chinchilla lanigera

<400> SEQUENCE: 42

Asp Ser Ser Ser Ala Phe Thr Leu Asn Glu Leu Arg
1               5                   10

<210> SEQ ID NO 43
<211> LENGTH: 12
<212> TYPE: PRT
<213> ORGANISM: Dasypus novemcinctus

<400> SEQUENCE: 43

Asp Ser Ser Tyr Ala Phe Thr Leu Asp Glu Leu Trp
1               5                   10

<210> SEQ ID NO 44
<211> LENGTH: 12
<212> TYPE: PRT
<213> ORGANISM: Odobenus rosmarus divergens

<400> SEQUENCE: 44

Asn Ser Ser Ser Ala Phe Thr Leu Asp Glu Leu Arg
1               5                   10

<210> SEQ ID NO 45
<211> LENGTH: 12
<212> TYPE: PRT
<213> ORGANISM: Cyphellophora europaea

<400> SEQUENCE: 45

Ala Thr Ser His Ala Ile Thr Leu Asp Glu Leu Arg
1               5                   10

<210> SEQ ID NO 46
<211> LENGTH: 12
<212> TYPE: PRT
<213> ORGANISM: Loxodonta africana

<400> SEQUENCE: 46

Asn Ser Ser Tyr Ala Phe Thr Met Asp Glu Leu Arg
1               5                   10

<210> SEQ ID NO 47
<211> LENGTH: 12
<212> TYPE: PRT
<213> ORGANISM: Cricetulus griseus

<400> SEQUENCE: 47

Asp Arg Ser Tyr Ser Phe Thr Leu Asp Glu Leu Arg
1               5                   10

<210> SEQ ID NO 48
<211> LENGTH: 12

```
<212> TYPE: PRT
<213> ORGANISM: Oryctolagus cuniculus

<400> SEQUENCE: 48

Asp Ser Ala Tyr Ala Phe Thr Val Asp Glu Leu Arg
1               5                   10

<210> SEQ ID NO 49
<211> LENGTH: 12
<212> TYPE: PRT
<213> ORGANISM: Octodon degus

<400> SEQUENCE: 49

Asp Ser Ser Ser Ala Phe Asn Leu Asn Glu Leu Arg
1               5                   10

<210> SEQ ID NO 50
<211> LENGTH: 12
<212> TYPE: PRT
<213> ORGANISM: Canis lupus familiaris

<400> SEQUENCE: 50

Asn Ser Ser Asp Ala Phe Ser Leu Asp Glu Leu Arg
1               5                   10

<210> SEQ ID NO 51
<211> LENGTH: 12
<212> TYPE: PRT
<213> ORGANISM: Monodelphis domestica

<400> SEQUENCE: 51

Asn Ser Ser Tyr Ser Phe Thr Leu Asp Glu Leu Arg
1               5                   10

<210> SEQ ID NO 52
<211> LENGTH: 12
<212> TYPE: PRT
<213> ORGANISM: Equus caballus

<400> SEQUENCE: 52

Asn Ser Ser Tyr Ala Phe Thr Val Asp Glu Leu Arg
1               5                   10

<210> SEQ ID NO 53
<211> LENGTH: 12
<212> TYPE: PRT
<213> ORGANISM: Condylura cristata

<400> SEQUENCE: 53

Asn Ser Ser Tyr Ala Phe Ser Leu Asp Glu Leu Arg
1               5                   10

<210> SEQ ID NO 54
<211> LENGTH: 11
<212> TYPE: PRT
<213> ORGANISM: Homo sapien

<400> SEQUENCE: 54

Ser Ala Ser Asp Leu Thr Trp Asp Asn Leu Lys
1               5                   10

<210> SEQ ID NO 55
<211> LENGTH: 11
<212> TYPE: PRT
<213> ORGANISM: Homo sapien
```

```
<400> SEQUENCE: 55

Ser Asp Thr Ser Leu Thr Trp Asn Ser Val Lys
1               5                   10

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
aactttggca ttgtggaagg                                              20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
acacattggg ggtaggaaca                                              20

<210> SEQ ID NO 58
<211> LENGTH: 20
<212> TYPE: DNA
<213> ORGANISM: Artificial Sequence
<220> FEATURE:
<223> OTHER INFORMATION: Primer

<400> SEQUENCE: 58
gcctttattg tgcggagaga                                              20

<210> SEQ ID NO 59
<211> LENGTH: 22
<212> TYPE: DNA
<213> ORGANISM: Artificial Sequence
<220> FEATURE:
<223> OTHER INFORMATION: Primer

<400> SEQUENCE: 59
cttgacttga tggaggcagt ag                                           22
```

P97-POLYNUCLEOTIDE CONJUGATES

CROSS-REFERENCE TO RELATED APPLICATIONS

This application claims priority under 35 U.S.C. § 119(e) to U.S. Application No. 62/144,598, filed Apr. 8, 2014; U.S. Application No. 62/033,903, filed Aug. 6, 2014; and U.S. Application No. 61/987,228, filed May 1, 2014, each of which is incorporated by reference in its entirety.

SEQUENCE LISTING

The Sequence Listing associated with this application is provided in text format in lieu of a paper copy, and is hereby incorporated by reference into the specification. The name of the text file containing the Sequence Listing is BIOA_010_03WO_ST25.txt. The text file is about 42 KB, was created on May 1, 2015, and is being submitted electronically via EFS-Web.

BACKGROUND

Technical Field

The present invention relates to conjugates between p97 (melanotransferrin) and polynucleotides such as small interfering RNA (siRNA) molecules, and related compositions and methods of use thereof, for instance, to facilitate delivery of siRNA agents across the blood-brain barrier (BBB) and/or improve their tissue penetration in CNS and/or peripheral tissues, and thereby treat and/or diagnose various diseases, including those having a central nervous system (CNS) component.

Description of the Related Art

RNA interference (RNAi) is a biological process in which RNA molecules inhibit gene expression, typically by causing the destruction of specific mRNA molecules. It may be possible to exploit RNA interference in therapy. Although it is difficult to introduce long dsRNA strands into mammalian cells due to the interferon response, the use of short interfering RNA (siRNA) has been more successful.

However, delivery into desired tissues such as tissues of the central nervous system (CNS) presents challenges to the therapeutic use of siRNA molecules. As one problem, the blood-brain barrier (BBB) blocks the free transfer of many agents from blood to brain. For this reason, diseases that present with significant neurological aspect are not expected to be as responsive to routine routes of administration such as IV or subcutaneous administration. For such diseases and others, methods of improving the delivery of the siRNA molecules across the BBB would be highly desirable.

BRIEF SUMMARY OF THE INVENTION

Embodiments of the present invention include conjugates between p97 (melanotransferrin) and polynucleotides such as small interfering RNA (siRNA) molecules, and related compositions and methods of use thereof. Thus, certain embodiments include p97 conjugates, comprising a p97 polypeptide that is covalently linked to a first polynucleotide of about 15-40 nucleotides in length with an optional linker (L) in between, and a second polynucleotide of about 15-40 nucleotides in length which is substantially complementary to and hybridized to the first polynucleotide, where the first or second polynucleotide is an antisense strand that is substantially complementary to a target mRNA sequence.

In some embodiments, the first and second polynucleotides form 1-3 nucleotide overhang(s) at the 3' end of the antisense strand, the 5' end of the antisense strand, or both. In certain embodiments, the first polynucleotide is the antisense strand and the second polynucleotide is a sense strand. In certain embodiments, the second polynucleotide is the antisense strand and the first polynucleotide is a sense strand.

In certain embodiments, the first and second polynucleotides are about 15, 16, 17, 18, 19, 20, 21, 22, 23, 24, 25, 26, 27, 28, 29, 30, 31, 32, 33, 34, 35, 36, 37, 38, 39, or 40 nucleotides in length. In some embodiments, the antisense strand is substantially or fully complementary to a target mRNA sequence of a gene selected from Table 2.

In certain embodiments, the gene is a human NOX gene. In some embodiments, the human NOX gene is one or more of NOX1, NOX2, or NOX4. In specific embodiments, the human NOX gene is NOX4 and where the first and second polynucleotides are selected from 5'-A UGU UCA CAA AGU CAG GUC TT-3' (SEQ ID NO:31) and 5'-GAC CUG ACU UUG UGA ACA UTT-3' (SEQ ID NO:32).

In certain embodiments, the p97 polypeptide comprises (a) an amino acid sequence set forth in SEQ ID NO:1-30 or Table 1 or Table B; (b) an amino acid sequence at least 90% identical to a sequence of (a); (c) or an amino acid sequence that differs from a sequence of (a) by addition, substitution, insertion, or deletion of about 1-50 amino acids. In some embodiments, the p97 polypeptide is about 10-50 amino acids in length. In certain embodiments, the p97 polypeptide is about 12, 13, 14, 15, 16, 17, 18, 19, 20, 21, 22, 23, 24, 25, 26, 27, 28, 29, or 30 amino acids in length.

In particular embodiments, the p97 polypeptide comprises, consists, or consists essentially of DSSHAFTLDELR (SEQ ID NO:14) or DSSHAFTLDELRYC (SEQ ID NO:29) or DSSHAFTLDELRC (SEQ ID NO:30). In certain embodiments, the p97 polypeptide has a cysteine residue at the C-terminus, the N-terminus, or both. In some embodiments, the conjugate comprises the linker (L) in between.

Also included are pharmaceutical compositions, comprising a pharmaceutically-acceptable carrier and a p97 conjugate described herein, where the pharmaceutical composition is sterile and non-pyrogenic.

Also included are methods for the treatment of a disease in a subject in need thereof, comprising administering to the subject a p97 conjugate or pharmaceutical composition described herein. In certain embodiments, the target gene is a human NOX gene, optionally NOX1, NOX2, or NOX4, and where the subject has a NOX-associated disease or condition of the central nervous system (CNS). In some embodiments, the NOX-associated disease or condition of the CNS is a neurodegenerative disease, a psychiatric disease, ischemia, stroke, CNS trauma, or neuropathic pain.

In certain embodiments, the p97 conjugate or pharmaceutical composition is administered by intravenous (IV) infusion or subcutaneous injection.

BRIEF DESCRIPTION OF THE DRAWINGS

FIG. 9A shows that NOX4 mRNA is significantly down-regulated in brain tissues from mice treated with p97-siRNA conjugate relative to controls (PBS and unconjugated siRNA). FIG. 9B shows the percentage reduction in endogenous NOX4 expression in brain tissues from mice treated with p97-siRNA conjugate relative to unconjugated siRNA. FIG. 9C shows the fold-reduction (~1.8-fold) in NOX4 expression in brain tissues from mice treated with p97-siRNA conjugate relative to unconjugated siRNA.

FIG. 12A shows that MTfp-siRNA pretreatment led to lower Nox4 induction in the stroke-induced portion of brain relative to PBS or siRNA-only ($\Delta Ct=Ct(nox4, PBS\text{-}sham)-Ct(B\text{-}actin, PBS\text{-}sham)$). FIG. 12B likewise shows that MTfp-siRNA pretreatment reduced NOX4 mRNA expression in the stroke induced brain relative to PBS or siRNA-only ($\Delta\Delta CT=(CT(Nox4,PBS\text{-}sham)-CT(B\text{-}actin, PBS\text{-}sham))-(CT(Nox4, MTfp\text{-}siRNA\text{-}stroke)-CT(B\text{-}actin, MTfp\text{-}siRNA\text{-}stroke))$).

DETAILED DESCRIPTION

Figure 1:
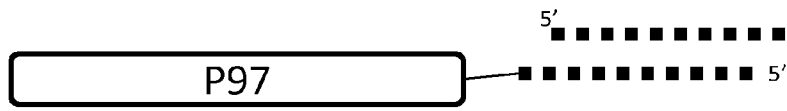
FIGS. 1A-1L illustrate the general structure of exemplary conjugates having a p97 (melanotransferrin) polypeptide that is covalently linked least one strand of an siRNA molecule or an shRNA molecule, and optionally a linker (L).
Figure 1:
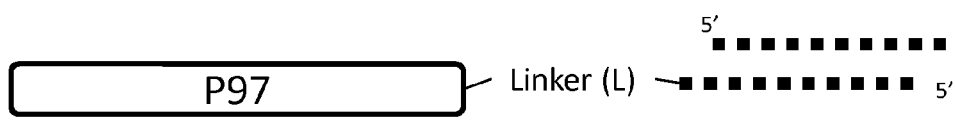
Figure 1:
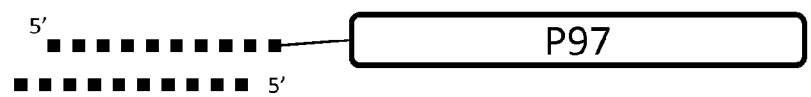
Figure 1:
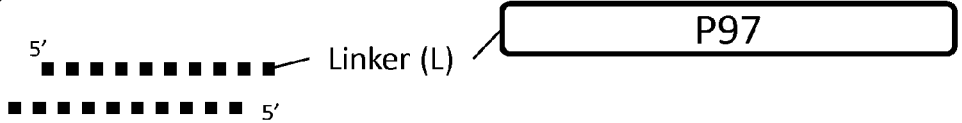
Figure 1:
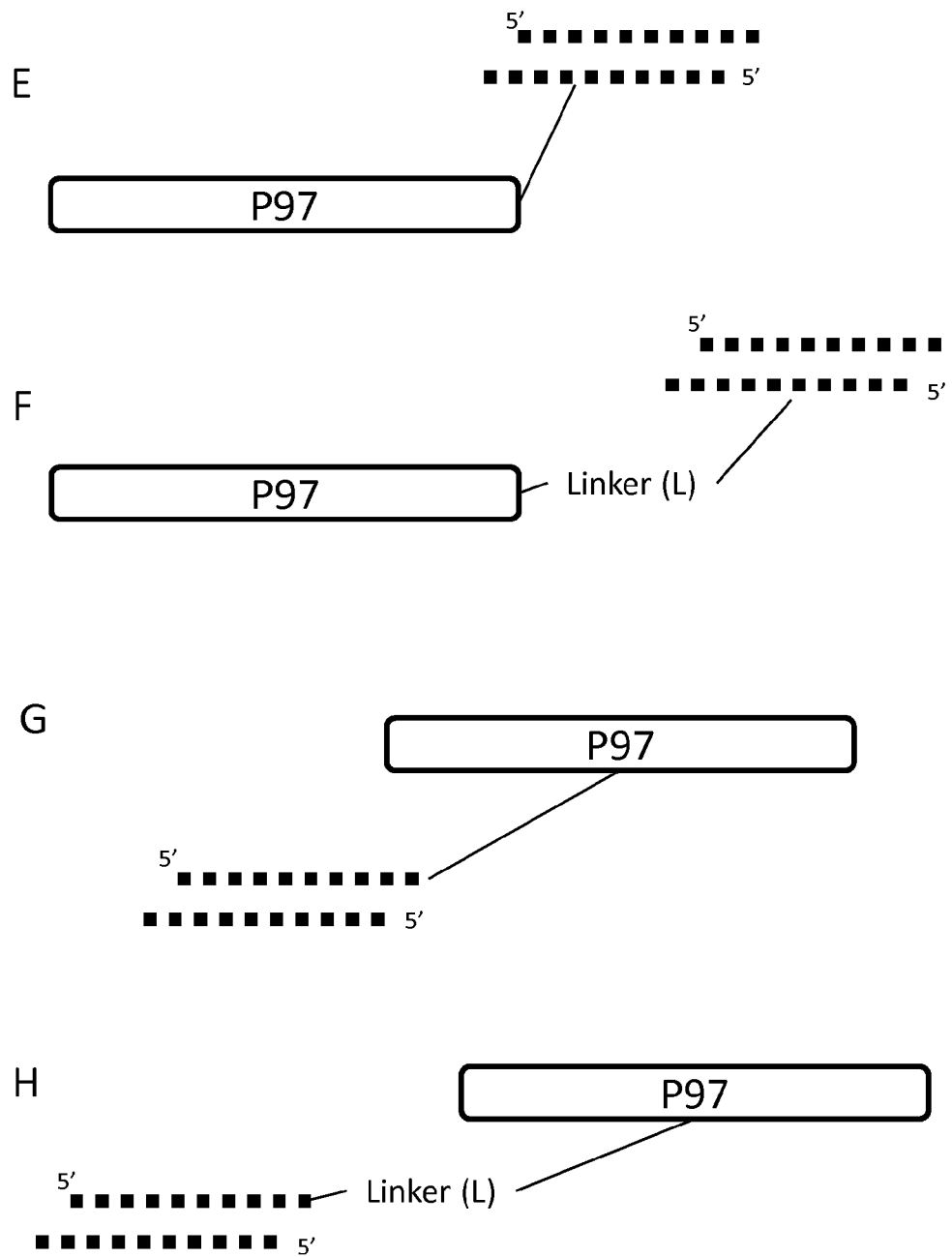
Figure 1:
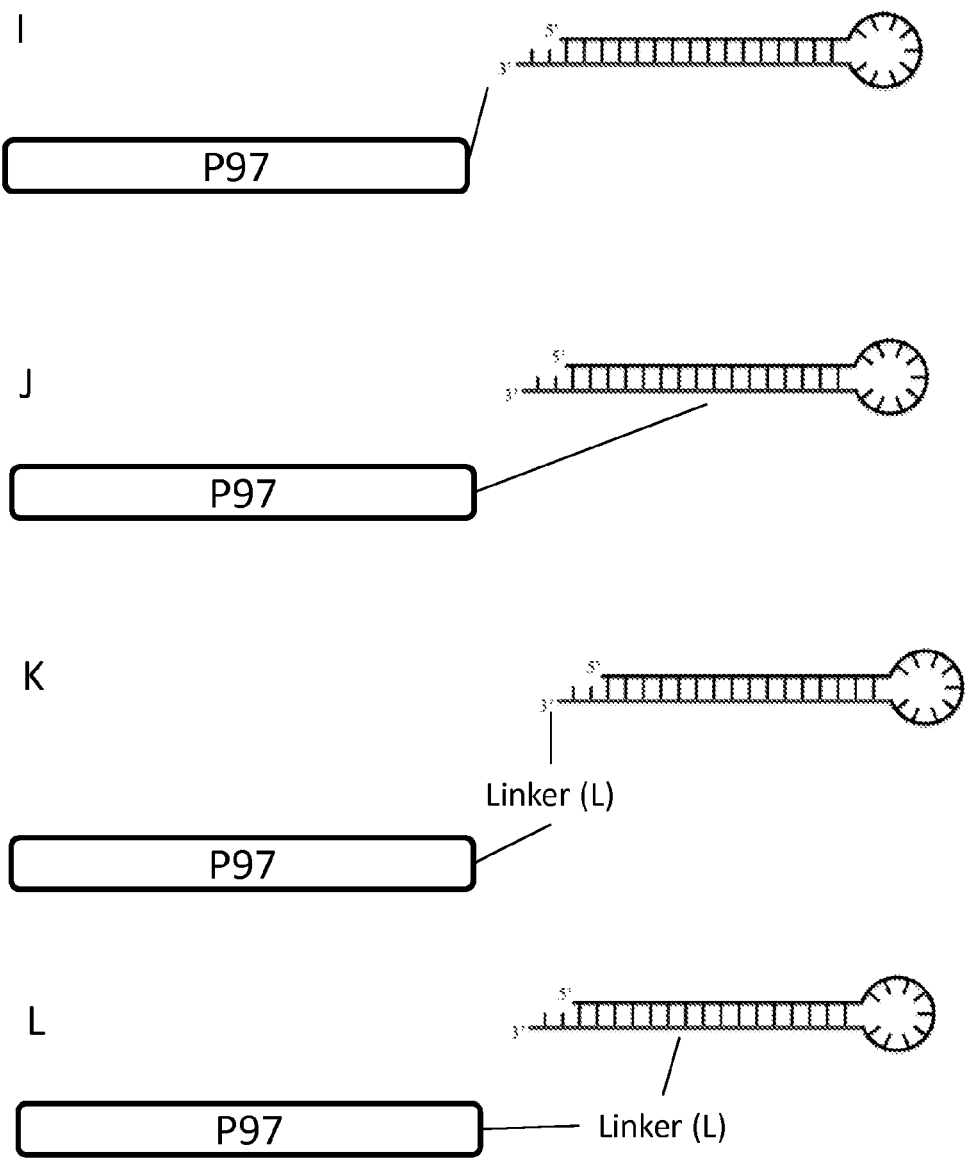
Figure 2:
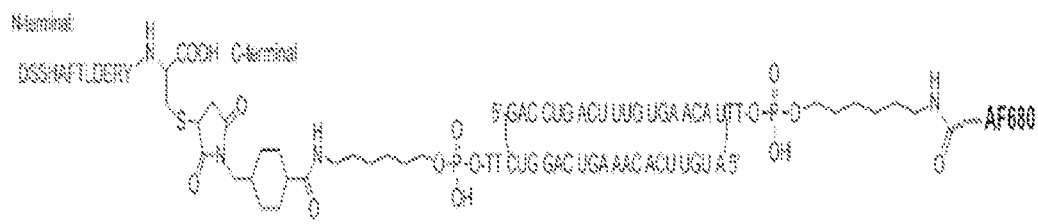
FIG. 2 illustrates the structure of an exemplary p97-siRNA conjugate (see Example 1).
Figure 2:
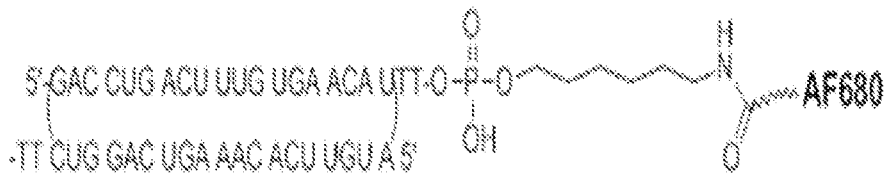

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., Molecular Cloning: A Laboratory Manual (3rd Edition, 2000); DNA Cloning: A Practical Approach, vol. I & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, 5th Ed. Hoboken N.J., John Wiley & Sons; B. Perbal, A Practical Guide to Molecular Cloning (3rd Edition 2010); Farrell, R., RNA Methodologies: A Laboratory Guide for Isolation and Characterization (3rd Edition 2005). Poly(ethylene glycol), Chemistry and Biological Applications, ACS, Washington, 1997; Veronese, F., and J. M. Harris, Eds., Peptide and protein PEGylation, Advanced Drug Delivery Reviews, 54(4) 453-609 (2002); Zalipsky, S., et al., "Use of functionalized Poly(Ethylene Glycols) for modification of polypeptides" in Polyethylene Glycol Chemistry: Biotechnical and Biomedical Applications.

All publications, patents, and patent applications cited herein are hereby incorporated by reference in their entirety.

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" is intended to refer to the entity formed as a result of covalent or non-covalent attachment or linkage of an agent or other molecule, e.g., a biologically active molecule, to a p97 polypeptide.

As used herein, the terms "function" and "functional" and the like refer to a biological, enzymatic, or therapeutic function.

"Homology" refers to the percentage number of amino acids that are identical or constitute conservative substitutions. Homology may be determined using sequence comparison programs such as GAP (Deveraux et al., *Nucleic Acids Research*. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the amount produced by no composition (e.g., the absence of a conjugate of the invention) or a control composition, sample or test subject. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition or a control composition, including all integers in between. As one non-limiting example, a control could compare the activity, such as the amount or rate of transport/delivery across the blood brain barrier, the rate and/or levels of distribution to central nervous system tissue, and/or the $C_{max}$ for plasma, central nervous system tissues, or any other systemic or peripheral non-central nervous system tissues, or the ability to attenuate expression of a target gene (e.g., in CNS tissues), of a p97-siRNA conjugate relative to the siRNA molecule alone. Other examples of comparisons and "statistically significant" amounts are described herein.

The phrase "attenuating expression" with reference to a gene or an mRNA as used herein means administering or expressing an amount of an siRNA to reduce translation of a target mRNA into protein, either through mRNA cleavage or through direct inhibition of translation. The terms "inhibit," "silencing," and "attenuating" as used herein refer to a measurable reduction in expression of a target mRNA or the corresponding protein as compared with the expression of the target mRNA or the corresponding protein in the absence of an interfering RNA of the invention. The reduction in expression of the target mRNA or the corresponding protein can be evaluated relative to levels present following administration or expression of a non-targeting control siRNA and/or an unconjugated siRNA. In certain embodiments, a p97-siRNA conjugate has "increased" attenuation of target gene expression in CNS tissues (e.g., upon peripheral administration in vivo) relative to a corresponding, unconjugated siRNA.

Unless otherwise specified, the term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. In some embodiments, all nucleotides are selected from the group of modified or unmodified A, C, G or U.

The term nucleotide is also meant to include modified bases and universal bases. By way of example, universal bases include but are not limited to 3-nitropyrrole, 5-nitroindole, or nebularine. The term "nucleotide" is also meant to include the N3' to P5' phosphoramidate, resulting from the substitution of a ribosyl 3' oxygen with an amine group.

Further, the term nucleotide also includes those species that have a detectable label, such as for example a radioactive or fluorescent moiety, or mass label attached to the nucleotide.

In certain embodiments, the "purity" of any given agent (e.g., a p97 conjugate) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

A "physiologically cleavable" or "hydrolyzable" or "degradable" linker or bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include, but are not limited to: carboxylate ester, phosphate ester, anhydride, acetal, ketal, acyloxyalkyl ether, imine, orthoester, thio ester, thiol ester, carbonate, and hydrazone, peptides and oligonucleotides.

A "releasable linker" includes, but is not limited to, a physiologically cleavable linker and an enzymatically degradable linker. Thus, a "releasable linker" is a linker that may undergo either spontaneous hydrolysis, or cleavage by some other mechanism (e.g., enzyme-catalyzed, acid-catalyzed, base-catalyzed, and so forth) under physiological conditions. For example, a "releasable linker" can involve an elimination reaction that has a base abstraction of a proton, (e.g., an ionizable hydrogen atom, Ha), as the driving force. For purposes herein, a "releasable linker" is synonymous with a "degradable linker." An "enzymatically degradable linkage" includes a linkage, e.g., amino acid sequence that is subject to degradation by one or more enzymes, e.g., peptidases or proteases. In particular embodiments, a releasable or otherwise degradable linker has a half-life at pH 7.4, 25° C., e.g., a physiological pH, human body temperature (e.g., in vivo), of about 30 minutes, about 1 hour, about 2 hour, about 3 hours, about 4 hours, about 5 hours, about 6 hours, about 12 hours, about 18 hours, about 24 hours, about 36 hours, about 48 hours, about 72 hours, or about 96 hours or less.

The term "reference sequence" refers generally to a nucleic acid coding sequence, or amino acid sequence, to which another sequence is being compared. All polypeptide and polynucleotide sequences described herein are included as references sequences, including those described by name and those described in the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99%, or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., *Nucl. Acids Res.* 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of a protein or conjugate to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (~37° C.). In certain embodiments, a p97 conjugate has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at about 37° C.

A "subject," as used herein, includes any animal that exhibits a symptom, or is at risk for exhibiting a symptom, which can be treated or diagnosed with a p97 conjugate of the invention. Suitable subjects (patients) include laboratory animals (such as mouse, rat, rabbit, or guinea pig), farm animals, and domestic animals or pets (such as a cat or dog). Non-human primates and, preferably, human patients, are included.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

The term "target" is used in a variety of different forms throughout this document and is defined by the context in which it is used. "Target mRNA" refers to a messenger RNA to which a given siRNA can be directed against. "Target sequence" and "target site" refer to a sequence within the mRNA to which the sense strand of an siRNA shows varying degrees of identity and the antisense strand exhibits varying degrees of complementarity. The phrase "siRNA target" can refer to the gene, mRNA, or protein against which an siRNA is directed. Similarly, "target silencing" can refer to the state of a gene, or the corresponding mRNA or protein.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild type gene or gene product (e.g., a polypeptide) is that which is most frequently observed in a population and is thus arbitrarily designed the "normal" or "wild-type" form of the gene.

p97-Polynucleotide Conjugates

Embodiments of the present invention relate generally to conjugates that comprise a p97 (melanotransferrin; MTf) polypeptide that is covalently or operatively linked to at least one polynucleotide, for example, at least one strand of a double-stranded small interfering RNA (siRNA) molecule, and related compositions and methods of use thereof. Exemplary p97 polypeptide sequences (e.g., Table 1) and siRNA target genes (e.g., Table 2) are described herein. In certain embodiments, the p97 conjugate comprises one or more linkers (L) between the p97 polypeptide and the nucleic acid molecule, examples of which are provided herein. Variants and fragments of any of the foregoing are also included and described herein.

In certain embodiments, the p97 conjugate comprises, consists, or consists essentially of at least one of the exemplary, non-limiting configurations illustrated in FIGS. 1A-1H or 2A. For example, in certain embodiments, a polynucleotide strand of the siRNA molecule is conjugated to the N-terminus of the p97 polypeptide. In some embodiments, a polynucleotide strand of the siRNA molecule is conjugated to the C-terminus of the p97 polypeptide. In particular embodiments, a polynucleotide strand of the siRNA molecule is conjugated to an internal amino acid of the p97 polypeptide, for example, an S-containing amino acid such as a methionine or cysteine. In some of these and related embodiments, the polynucleotide strand of the siRNA molecule is conjugated to the p97 polypeptide via a linker.

In certain embodiments, the p97 polypeptide is conjugated to the 3'-end of a polynucleotide strand of the siRNA molecule. In certain embodiments, the p97 polypeptide is conjugated to the 5'-end of a polynucleotide strand of the siRNA molecule. In particular embodiments, the p97 polypeptide is conjugated to an internal nucleobase of a polynucleotide strand of the siRNA molecule. In some of these and related embodiments, the p97 polypeptide is conjugated to the polynucleotide of the siRNA molecule via a linker.

In some embodiments, the p97 polypeptide is conjugated to the sense polynucleotide strand of the siRNA molecule, as described herein. In certain embodiments, the p97 polypeptide is conjugated to the antisense polynucleotide strand of the siRNA molecule, as described herein.

Certain conjugates can employ more than one p97 polypeptide. For instance, in some embodiments, a first p97 polypeptide is conjugated to the sense strand and a second p97 polypeptide (being the same or different) is conjugated to the antisense strand. In some embodiments, 1, 2, 3, 4, or 5 p97 polypeptides are conjugated to a polynucleotide strand of an siRNA molecule.

Some conjugates may employ more than one siRNA molecule. For instance, in certain embodiments, a p97 polypeptide is conjugated to 1, 2, 3, 4, or 5 polynucleotide strands of an siRNA molecule. In some aspects, a p97 polypeptide is conjugated to 1, 2, 3, 4, or 5 sense strands of an siRNA molecule. In certain aspects, a p97 polypeptide is conjugated to 1, 2, 3, 4, or 5 antisense strands of an siRNA molecule. In particular aspects, a p97 polypeptide is conjugated to mixture of sense and antisense strands, such as 1, 2, 3, 4, or 5 sense strands and 1, 2, 3, 4, or 5 antisense strands of an siRNA molecule.

Also included are combinations of any of the foregoing.

Figure 6:
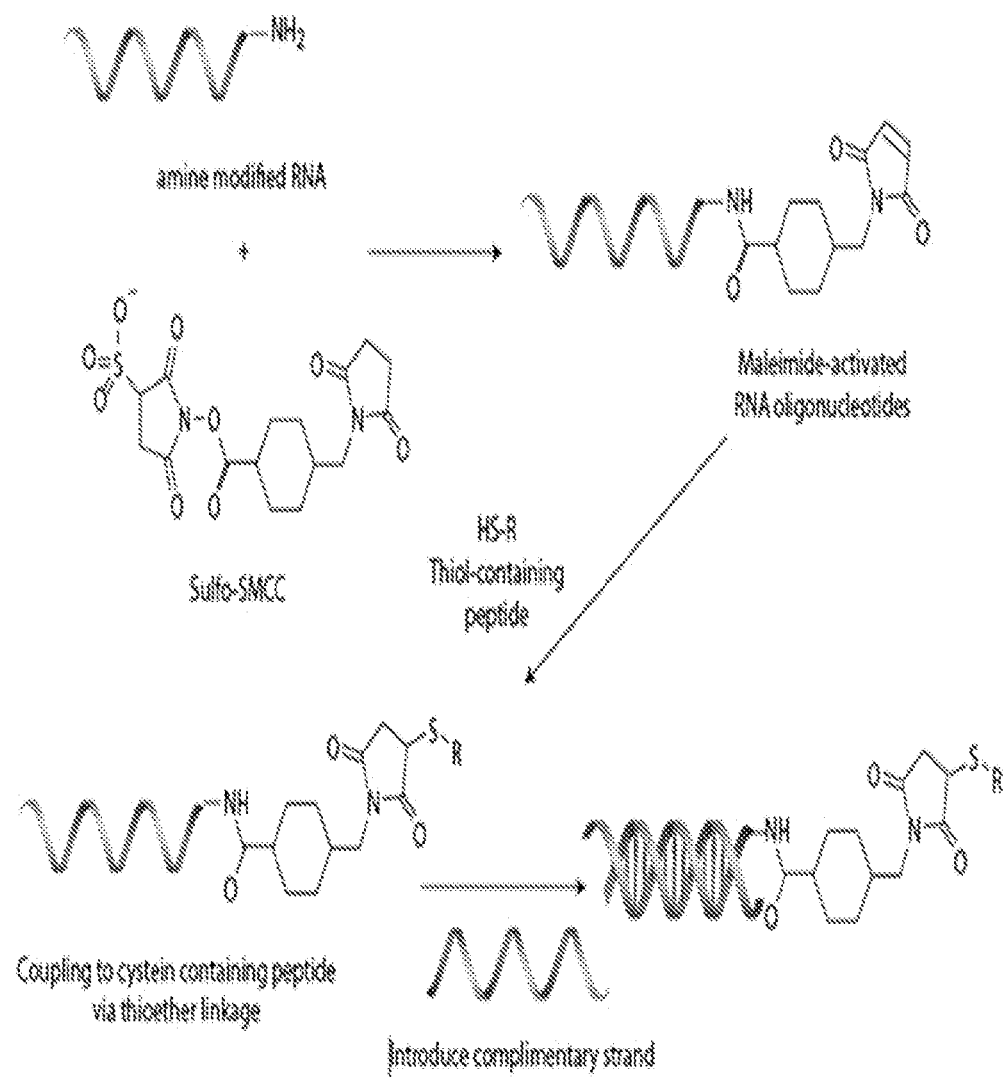
FIG. 6 illustrates a reaction scheme for conjugating a p97 polypeptide to a polynucleotide strand of an siRNA molecule to create a p97-siRNA conjugate.

Conjugates between p97 polypeptides and polynucleotide strands of siRNA molecules can be prepared according to a variety of techniques in the art. For example, certain embodiments may utilize thiol-containing siRNAs (see Muratovska and Eccles, FEBS Lett. 558:63-68, 2004) or other approaches (see Jeong et al., Bioconjugate Chem. 20:5-14, 2009). In some embodiments, the 5'-terminus, internal nucleobase(s), or 3'-terminus of an siRNA strand can be covalently linked to the N-terminus, internal residue (s), or C-terminus of a peptide using one or more preactivated small molecules with functional groups that reside in the polypeptide and polynucleotide such as amine, thiol, carboxylate, hydroxyl, aldehyde and ketone, active hydrogen, photo-chemical and cycloaddition reactions, and by crosslinking with one another through variety of different conjugation chemistries that include either stable, cleavable, or labile linkages. In some aspects, polymer conjugates can be prepared, for example, by conjugating an aminooxy-derivatized cationic block copolymer to the p97 polypeptide by means of genetically encoded p-acetyl phenylalanine (pAcF) (see Lu et al., J Am Chem Soc. 135:13885-91, 2013), and then conjugating a polynucleotide strand of the siRNA molecule to the copolymer. Another example of a method for linking complex molecules such as polynucleotides to a p97 polypeptide is the SATA/sulfo-SMCC cross-linking reaction (Pierce (Rockford, Ill.)). One exemplary approach is illustrated in FIG. 6.

Conjugates can be constructed using any of the p97, L, or siRNA molecules described herein, including functional or active variants and fragments thereof.

In certain embodiments, the conjugates have a purity of at least about 90%, as measured according to routine techniques in the art. In certain embodiments, such as diagnostic compositions or certain therapeutic compositions, the conjugates have a purity of at least about 95%. In specific embodiments, such as therapeutic or pharmaceutical compositions, the conjugates have a purity of at least about 97% or 98% or 99%. In other embodiments, such as when being used as reference or research reagents, conjugates can be of lesser purity, and may have a purity of at least about 50%, 60%, 70%, or 80%. Purity can be measured overall or in relation to selected components, such as other proteins, e.g., purity on a protein basis.

In certain embodiments, as noted above, the conjugates and/or compositions described herein are about substantially endotoxin free, including, for example, about 95% endotoxin free, preferably about 99% endotoxin free, and more preferably about 99.99% endotoxin free. The presence of endotoxins can be detected according to routine techniques in the art, as described herein.

p97 Polypeptides. In certain embodiments, a p97 polypeptide sequence used in a conjugate comprises, consists essentially of, or consists of a human p97 reference sequence provided in Table 1 below. Also included are variants and fragments thereof.

TABLE 1

Exemplary p97 Sequences

| Description | Sequence | SEQ ID NO: |
|---|---|---|
| FL Human p97 | MRGPSGALWLLLALRTVLGGMEVRWCATSDPEQ PHKCGNMSEAFREAGIQSLLCVRGTSADHCVQL IAAQEADAITLDGGAIYEAGKEHGLKPVVGEVY DQEVGTSYYAVAVVRRSSHVTIDTLKGVKSCHT GINRTVGWNVPVGYLVESGRLSVMGCDVLKAVS DYFGGSCVPGAGETSYSESLCRLCRGDSSGEGV CDKSPLERYYDYSGAFRCLAEGAGDVAFVKHST VLENTDGKTLPSWGQALLSQDFELLCRDGSRAD VTEWRQCHLARVPAHAVVVRADTDGGLIFRLLN EGQRLFSHEGSSFQMFSSEAYGQKDLLFKDSTS ELVPIATQTYEAWLGHEYLHAMKGLLCDPNRLP PYLRWCVLSTPEIQKCGDMAVAFRRQRLKPEIQ CVSAKSPQHCMERIQAEQVDAVTLSGEDIYTAG KTYGLVPAAGEHYAPEDSSNSYYVVAVVRRDSS HAFTLDELRGKRSCHAGFGSPAGWDVPVGALIQ RGFIRPKDCDVLTAVSEFFNASCVPVNNPKNYP SSLCALCVGDEQGRNKCVGNSQERYYGYRGAFR CLVENAGDVAFVRHTTVFDNTNGHNSEPWAAEL RSEDYELLCPNGARAEVSQFAACNLAQIPPHAV MVRPDTNIFTVYGLLDKAQDLFGDDHNKNGFKM FDSSNYHGQDLLFKDATVRAVPVGEKTTYRGWL GLDYVAALEGMSSQQCSGAAAPAPGAPLLPLLL PALAARLLPPAL | 1 |
| Soluble Human p97 | GMEVRWCATSDPEQHKCGNMSEAFREAGIQPSL LCVRGTSADHCVQLIAAQEADAITLDGGAIYEA GKEHGLKPVVGEVYDQEVGTSYYAVAVVRRSSH VTIDTLKGVKSCHTGINRTVGWNVPVGYLVESG RLSVMGCDVLKAVSDYFGGSCVPGAGETSYSES LCRLCRGDSSGEGVCDKSPLERYYDYSGAFRCL AEGAGDVAFVKHSTVLENTDGKTLPSWGQALLS QDFELLCRDGSRADVTEWRQCHLARVPAHAVVV RADTDGGLIFRLLNEGQRLFSHEGSSFQMFSSE AYGQKDLLFKDSTSELVPIATQTYEAWLGHEYL HAMKGLLCDPNRLPPYLRWCVLSTPEIQKCGDM AVAFRRQRLKPEIQCVSAKSPQHCMERIQAEQV DAVTLSGEDIYTAGKTYGLVPAAGEHYAPEDSS NSYYVVAVVRRDSSHAFTLDELRGKRSCHAGFG SPAGWDVPVGALIQRGFIRPKDCDVLTAVSEFF NASCVPVNNPKNYPSSLCALCVGDEQGRNKCVG NSQERYYGYRGAFRCLVENAGDVAFVRHTTVFD NTNGHNSEPWAAELRSEDYELLCPNGARAEVSQ FAACKLAQIPPHAVMVRPDTNIFTVYGLLDKAQ DLFGDDHNKNGFKMFDSSNYHGQDLLFKDATVR AVPVGEKTTYRGWLGLDYVAALEGMSSQQCSG | 2 |
| P97 fragment | WCATSDPEQHK | 3 |
| P97 fragment | RSSHVTIDTLK | 4 |
| P97 fragment | SSHVTIDTLKGVK | 5 |
| P97 fragment | LCRGDSSGEGVCDK | 6 |
| P97 fragment | GDSSGEGVCDKSPLER | 7 |
| P97 fragment | YYDYSGAFR | 8 |
| P97 fragment | ADVTEWR | 9 |
| P97 fragment | VPAHAVVVR | 10 |
| P97 fragment | ADTDGGLIFR | 11 |
| P97 fragment | CGDMAVAFR | 12 |
| P97 fragment | LKPEIQCVSAK | 13 |
| P97 fragment | DSSHAFTLDELR | 14 |
| P97 fragment | SEDYELLCPNGAR | 15 |
| P97 fragment | AQDLFGDDHNKNGFK | 16 |
| P97 fragment | FSSEAYGQKDLLFKDSTSELVPIATQTYEAWLG HEYLHAM | 17 |
| P97 fragment | ERIQAEQVDAVTLSGEDIYTAGKTYGLVPAAGE HYAPEDSSNSYYVVAVVRRDSSHAFTLDELRGK RSCHAGFGSPAGWDVPVGALIQRGFIRPKDCDV LTAVSEFFNASCVPVNNPKNYPSSLCALCVGDE QGRNKCVGNSQERYYGYRGAFRCLVENAGDVAF VRHTTVFDNTNGHNSEPWAAELRSEDYELLCPN GARAEVSQFAACNLAQIPPHAVM | 18 |
| P97 fragment | VRPDTNIFTVYGLLDKAQDLFGDDHNKNGFKM | 19 |
| P97 fragment | GMEVRWCATSDPEQHKCGNMSEAFREAGIQPSL LCVRGTSADHCVQLIAAQEADAITLDGGAIYEA GKEHGLKPVVGEVYDQEVGTSYYAVAVVRRSSH VTIDTLKGVKSCHTGINRTVGWNVPVGYLVESG RLSVMGCDVLKAVSDYFGGSCVPGAGETSYSES LCRLCRGDSSGEGVCDKSPLERYYDYSGAFRCL AEGAGDVAFVKHSTVLENTDGKTLPSWGQALLS QDFELLCRDGSRADVTEWRQCHLARVPAHAVVV RADTDGGLIFRLLNEGQRLFSHEGSSFQMFSSE AYGQKDLLFKDSTSELVPIATQTYEAWLGHEYL HAMKGLLCDPNRLPPYLRWCVLSTPEIQKCGDM AVAFRRQRLKPEIQCVSAKSPQHCMERIQAEQV DAVTLSGEDIYTAGKTYGLVPAAGEHYAPEDSS NSYYVVAVVRRDSSHAFTLDELRGKRSCHAGFG SPAGWDVPVGALIQRGFIRPKDCDVLTAVSEFF NASCVPVNNPKNYPSSLCALCVGDEQGRNKCVG NSQERYYGYRGAFRCLVENAGDVAFVRHTTVFD NTN | 20 |
| P97 fragment | GHNSEPWAAELRSEDYELLCPN | 21 |

TABLE 1-continued

Exemplary p97 Sequences

| Description | Sequence | SEQ ID NO: |
|---|---|---|
| P97 fragment | GARAEVSQFAACNLAQIPPHAVMVRPDTNIFTV YGLLDKAQDLFGDDHNKN | 22 |
| P97 fragment | GFKMFDSSNYHGQDLLFKDATVRAVPVGEKTTY RGWLGLDYVAALEGMSSQQC | 23 |
| P97 fragment | GMEVRWCATSDPEQHKCGNMSEAFREAGIQPSL LCVRGTSADHCVQLIAAQEADAITLDGGAIYEA GKEHGLKPVVGEVYDQEVGTSYYAVAVVRRSSH VTIDTLKGVKSCHTGINRTVGWNVPVGYLVESG RLSVMGCDVLKAVSDYFGGSCVPGAGETSYSES LCRLCRGDSSGEGVCDKSPLERYYDYSGAFRCL AEGAGDVAFVKHSTVLENTDGKTLPSWGQALLS QDFELLCRDGSRADVTEWRQCHLARVPAHAVVV RADTDGGLIFRLLNEGQRLFSHEGSSFQMFSSE AYGQKDLLFKDSTSELVPIATQTYEAWLGHEYL HAMKGLLCDPNRLPPYLRWCVLSTPEIQKCGDM AVAFRRQRLKPEIQCVSAKSPQHCMERIQAEQV DAVTLSGEDIYTAGKTYGLVPAAGEHYAPEDSS NSYYVVAVVRRDSSHAFTLDELRGKRSCHAGFG SPAGWDVPVGALIQRGFIRPKDCDVLTAVSEFF NASCVPVNNPKNYPSSLCALCVGDEQGRNKCVG NSQERYYGYRGAFRCLVENAGDVAFVRHTTVFD NTNGHNSEPWAAELRSEDYELLCPN | 24 |
| P97 fragment | GMEVRWCATSDPEQHKCGNMSEAFREAGIQPSL LCVRGTSADHCVQLIAAQEADAITLDGGAIYEA GKEHGLKPVVGEVYDQEVGTSYYAVAVVRRSSH VTIDTLKGVKSCHTGINRTVGWNVPVGYLVESG YRLSVMGCDVLKAVSDFGGSCVPGAGETSYSES LCRLCRGDSSGEGVCDKSPLERYYDYSGAFRCL AEGAGDVAFVKHSTVLENTDGKTLPSWGQALLS QDFELLCRDGSRADVTEWRQCHLARVPAHAVVV RADTDGGLIFRLLNEGQRLFSHEGSSFQMFSSE AYGQKDLLFKDSTSELVPIATQTYEAWLGHEYL HAMKGLLCDPNRLPPYLRWCVLSTPEIQKCGDM AVAFRRQRLKPEIQCVSAKSPQHCMERIQAEQV DAVTLSGEDIYTAGKTYGLVPAAGEHYAPEDSS NSYYVVAVVRRDSSHAFTLDELRGKRSCHAGFG SPAGWDVPVGALIQRGFIRPKDCDVLTAVSEFF NASCVPVNNPKNYPSSLCALCVGDEQGRNKCVG NSQERYYGYRGAFRCLVENAGDVAFVRHTTVFD NTNGHNSEPWAAELRSEDYELLCPNGARAEVSQ FAACNLAQIPPHAVMVRPDTNIFTVYGLLDKAQ DLFGDDHNKN | 25 |
| P97 fragment | GHNSEPWAAELRSEDYELLCPNGARAEVSQFAA CNLAQIPPHAVMVRPDTNIFTVYGLLDKAQDLF GDDHNKN | 26 |
| P97 fragment | GHNSEPWAAELRSEDYELLCPNGARAEVSQFAA CNLAQIPPHAVMVRPDTNIFTVYGLLDKAQDLF GDDHNKNGFKMFDSSNYHGQDLLFKDATVRAVP VGEKTTYRGWLGLDYVAALEGMSSQQC | 27 |
| P97 fragment | GARAEVSQFAACNLAQIPPHAVMVRPDTNIFTV YGLLDKAQDLFGDDHNKNGFKMFDSSNYHGQDL LFKDATVRAVPVGEKTTYRGWLGLDYVAALEGM SSQQC | 28 |

In some embodiments, a p97 polypeptide sequence comprises a sequence having at least 70%, 75%, 80%, 85%, 90%, 95%, 96%, 97%, 98%, or 99% identity or homology, along its length, to a human p97 sequence in Table 1, or a fragment thereof.

In particular embodiments, a p97 polypeptide sequence comprises a fragment of a human p97 sequence in Table 1. In certain embodiments, a p97 polypeptide fragment is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 700, 710, 720, 730 or more amino acids in length, including all integers and ranges in between, and which may comprise all or a portion of the sequence of a p97 reference sequence, including any adjacent N-terminal and/or C-terminal sequences of a reference p97 fragment, as defined by SEQ ID NO:1.

In certain embodiments, a p97 polypeptide fragment is about 5-700, 5-600, 5-500, 5-400, 5-300, 5-200, 5-100, 5-50, 5-40, 5-30, 5-25, 5-20, 5-15, 5-10, 10-700, 10-600, 10-500, 10-400, 10-300, 10-200, 10-100, 10-50, 10-40, 10-30, 10-25, 10-20, 10-15, 20-700, 20-600, 20-500, 20-400, 20-300, 20-200, 20-100, 20-50, 20-40, 20-30, 20-25, 30-700, 30-600, 30-500, 30-400, 30-300, 30-200, 30-100, 30-50, 30-40, 40-700, 40-600, 40-500, 40-400, 40-300, 40-200, 40-100, 40-50, 50-700, 50-600, 50-500, 50-400, 50-300, 50-200, 50-100, 60-700, 60-600, 60-500, 60-400, 60-300, 60-200, 60-100, 60-70, 70-700, 70-600, 70-500, 70-400, 70-300, 70-200, 70-100, 70-80, 80-700, 80-600, 80-500, 80-400, 80-300, 80-200, 80-100, 80-90, 90-700, 90-600, 90-500, 90-400, 90-300, 90-200, 90-100, 100-700, 100-600, 100-500, 100-400, 100-300, 100-250, 100-200, 100-150, 200-700, 200-600, 200-500, 200-400, 200-300, or 200-250 amino acids in length, and comprises all or a portion of a p97 reference sequence, including any adjacent N-terminal and/or C-terminal sequences of a reference p97 fragment, as defined by SEQ ID NO:1.

Certain embodiments comprise one or more p97 polypeptides, for example, 2, 3, 4, or 5 polypeptides, as illustrated by the formula $[X]_n$, where X is a p97 polypeptide described herein and n is an integer from 1-5. In specific embodiments, X is DSSHAFTLDELR (SEQ ID NO:14).

In some embodiments, the p97 polypeptide has one or more terminal (e.g., N-terminal, C-terminal) cysteines and/or tyrosines, which can be added for conjugation and iodination, respectively. In some aspects, the cysteine residue provides a free sulfhydryl group to allow conjugation of the p97 polypeptide to the polynucleotide strand of the siRNA molecule, either directly or via a linker such as PEG-based linker.

In certain embodiments, p97 polypeptide sequences of interest include p97 amino acid sequences, subsequences, and/or variants of p97 that are effective for transporting an agent of interest across the blood brain barrier and into the central nervous system (CNS). In particular embodiments, the variant or fragment comprises the N-lobe of human p97 (residues 20-361 of SEQ ID NO:1). In specific aspects, the variant or fragment comprises an intact and functional $Fe^{3+}$-binding site.

In some embodiments, a p97 polypeptide sequence is a soluble form of a p97 polypeptide (see Yang et al., *Prot Exp Purif.* 34:28-48, 2004), or a fragment or variant thereof. In some aspects, the soluble p97 polypeptide has a deletion of the all or a portion of the hydrophobic domain (residues 710-738 of SEQ ID NO:1), alone or in combination with a deletion of all or a portion of the signal peptide (residues 1-19 of SEQ ID NO:1). In specific aspects, the soluble p97 polypeptide comprises or consists of SEQ ID NO:2 (residues 20-711 of SEQ ID NO:1), including variants and fragments thereof.

In certain embodiments, for instance, those that employ liposomes, the p97 polypeptide sequence is a lipid soluble form of a p97 polypeptide. For instance, certain of these and related embodiments include a p97 polypeptide that comprises all or a portion of the hydrophobic domain, optionally with or without the signal peptide.

In certain other embodiments, the p97 fragment or variant is capable of specifically binding to a p97 receptor, an LRP1 receptor and/or an LRP1B receptor.

In some embodiments, the p97 polypeptide is a recombinant polypeptide made, for example, from a bacterial cell, a yeast cell, an insect cell, or a eukaryotic cell such as a mammalian or human cell. In some embodiments, the recombinant p97 polypeptides are produced in substantially or completely serum free media. In some embodiments, the p97 polypeptide is a synthetic polypeptide.

Variants and fragments of reference p97 polypeptides and other reference polypeptides are described in greater detail below.

siRNA Molecules and other Polynucleotides. As noted above, embodiments of the present invention include p97 polypeptides that are covalently or otherwise attached to at least one polynucleotide. In particular embodiments, the polynucleotide is at least one strand of an siRNA molecule. The term "siRNA molecule" or "siRNA" refers to small inhibitory RNA duplexes that induce the RNA interference (RNAi) pathway. As used herein, these molecules can vary in length (generally 15-30 base pairs plus optionally overhangs) and contain varying degrees of complementarity to their target mRNA in the antisense strand. Some, but not all, siRNA have unpaired overhanging bases on the 5' or 3' end of the sense strand and/or the antisense strand.

The term "siRNA" includes duplexes of two separate strands, and unless otherwise specified also includes single strands that can form hairpin structures comprising a duplex region, such as short-hairpin RNAs ("shRNA"). Thus, in some embodiments, the polynucleotide is a shRNA molecule, and the p97 polypeptide is covalently or otherwise attached to a single-stranded polynucleotide that comprises a duplex region (see, e.g., FIGS. 1I-1L). In particular embodiments, a single-stranded hairpin shRNA molecule comprises, consists, or consists essentially of a stem of about, at least about, or no more than about 19-29 base pairs (i.e., about 19, 20, 21, 22, 23, 24, 25, 26, 27, 28, or 29 bp), a loop of about, at least about, or no more than about 4, 5, 6, 7, or 8 nucleotides, and optionally a dinucleotide overhang at the 3' end.

Also included as polynucleotides are CRISPR (clustered regularly interspaced short palindromic repeats) RNA oligonucleotides and TALEN (transcription activator-like effector nuclease) RNA oligonucleotides, including RNAs that form part of CRISPR RNA-guided surveillance complexes such as Cas9-crRNA complexes and others (see, e.g., WO 2013/142578; and U.S. Application Nos. 2010/0076057; 2011/018977; 2013/0011828; and 20130330778, which are incorporated by reference).

The term "sense strand" refers to a polynucleotide that comprises a sequence that is in whole or in part, the same as a target nucleic acid sequence such as messenger RNA or a sequence of DNA. The term "antisense strand" refers to a polynucleotide that comprises a sequence that is in whole or in part, the complement of a target nucleic acid sequence such as messenger RNA or a sequence of DNA.

Examples of lengths of sense strands and/or antisense strands include about 15-40 bases, about 19-36 bases, about 19-30 bases, about 19-25 bases, and about 19-23 bases. In particular embodiments, first and/or second single-stranded polynucleotides of an siRNA-conjugate are about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 bases or nucleotides in length including all ranges in between. These strand lengths include possible overhang regions. Thus, in particular embodiments, the first and second polynucleotides of an siRNA molecule form 1, 2, or 3 nucleotide overhang(s) at the 3' end of the antisense strand, the 5' end of the antisense strand, or both.

When a sequence of an siRNA is provided, by convention, unless otherwise indicated it is of the sense strand, and the complementary antisense strand is implicit. In a duplex siRNA (formed from two separate strands) one strand may be the sense strand, and the other strand may be the antisense strand. If overhangs are present, the phrase "sense region" may refer to the nucleotide sequence portion of the sense strand other than overhang regions. Similarly, the phrase "antisense region" may refer to the nucleotide sequence portion of the antisense strand other than overhang regions. If the siRNA is a shRNA, there are not two separate strands, and the "sense region" is the portion of the duplex region that has a sequence that is in whole or in part the same as the target sequence, and the "antisense region" is the sequence of nucleotides that is in whole or in part complementary to the target sequence and to the sense region.

Typically, siRNA, shRNA, or miRNA molecules comprise or form a duplex region. The term "duplex region" refers to the region in two complementary or substantially complementary polynucleotides that form base pairs with one another, either by Watson-Crick base pairing or any other manner that allows for a stabilized duplex between polynucleotide strands that are complementary or substantially complementary. Examples of sizes of duplex regions include but are not limited to about 17-30 base pairs, 17-25 base pairs, 17-23 base pairs, 18-30 base pairs, 18-25 base pairs, 18-23 base pairs, 19-30 base pairs, 19-25 base pairs and 19-23 base pairs. A duplex region may be defined by the length of base pairs, as well as the degree of complementarity over that range.

Thus, when the duplex region is formed from two separate strands of nucleotides, the antisense strand and the sense strand, each strand may contain nucleotides that are part of the duplex and nucleotides that are not part of the duplex at either the 5' end or the 3' end. An siRNA may be designed such that on the antisense strand, all nucleotides that are complementary to a target are part of the duplex region, and thus have complementary nucleotides on the sense strand. However, the siRNA may be also be designed such that the antisense strand also contains nucleotides at either its 3' end and/or its 5' end that although not having complementary nucleotides on the sense strand, are part of a continuous stretch of nucleotides within the antisense strand that have complementary nucleotides on the target.

By way of example, a sense strand may contain 19 nucleotides and an antisense strand may contain 21 nucleotides. All but the two 3' most nucleotides of the antisense strand may be complementary to the 19 nucleotides on the sense strand, while the entire stretch of 21 nucleotides of the antisense strand may be complementary to a stretch of 21 nucleotides of the target. Alternatively, the two 3' most nucleotides of the antisense strand may be selected so as not to be complementary to a portion of the target, or selected randomly or to facilitate processing such that one or both might or might not be complementary to the two nucleotides of the target that are adjacent to the nucleotides to which the other 19 nucleotides of the antisense strand are complementary. In some embodiments, there may for example be no mismatches, one mismatch, two mismatches, three mismatches, four mismatches, or five mismatches within a duplex region.

The term "mismatch" includes a situation in which Watson-Crick base pairing does not take place between a nucleotide of a sense strand and a nucleotide of an antisense strand. Examples of mismatches include but are not limited to an A across from a G, a C across from an A, a U across from a C, a U across from a G, an A across from an A, a G across from a G, a C across from C, and a U across from a U.

Typically, the first and second polynucleotide strands of an siRNA molecule are fully or substantially complementary to each other. The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can hydrogen bond with a nucleotide unit of a second polynucleotide strand. Less than perfect complementarity refers to the situation in which some, but not all, nucleotide units of two strands can hydrogen bond with each other. For example, for two 20-mers, if only two base pairs on each strand can hydrogen bond with each other, the polynucleotide strands exhibit 10% complementarity. In the same example, if 18 base pairs on each strand can hydrogen bond with each other, the polynucleotide strands exhibit 90% complementarity. In some embodiments, within a duplex region, there is at least 75% complementarity, at least 80% complementarity, at least 90% complementarity, at least 95% complementarity, or 100% complementarity.

In certain embodiments, the antisense strand of the siRNA molecule is fully or substantially complementary to a target mRNA sequence in a target gene. In some embodiments, the target mRNA sequence is pre-messenger RNA (pre-processed or pre-mRNA) sequence including introns and exons, or the processed mRNA sequence, typically including only the exonic sequences. In some embodiments, the antisense strand is at least 75% complementary, at least 80% complementary, at least 90% complementary, at least 95% complementary, or 100% complementary to a target mRNA sequence in a target gene. In particular embodiments, the antisense strand is fully or substantially complementary to a target mRNA sequence of a target gene selected from Table 2 below. Likewise, in some embodiments, the sense strand of the siRNA molecule is fully or substantially identical to a target mRNA sequence in a target gene. In some embodiments, the sense strand has at least 75% identity, at least 80% identity, at least 90% identity, at least 95% identity, or 100% identity to a target mRNA sequence in a target gene. In particular embodiments, the antisense strand is fully or substantially identical to a target mRNA sequence of a target gene selected from Table 2 below.

TABLE 2

| Target gene(s) | Examples of activity or disease association |
|---|---|
| NOX (NADPH Oxidase) genes such as NOX2 and NOX4 | Diseases associated with cell death, chronic kidney disease, diabetes and diabetic complications, neurocardiovascular disease such as myocardial infarction-induced cardiac dysfunction, neurodegenerative diseases, ischemic stroke |
| IKK-gamma | Activator of the NF-kappaB pathway (NF-kb), mediator of diseases such as asthma, arthritis, cancer, chronic inflammation, neurodegenerative diseases and heart disease |
| alpha-synuclein | Parkinson's disease |
| Beta-Amyloid | Alzheimer's disease |
| BACE1 | Alzheimer's disease |
| HD gene | Huntington's disease |
| IL-4 or IL-4 receptors | Inflammatory diseases such as asthma and other respiratory diseases, cardiovascular diseases |
| IL-13 or IL-13 receptors | Inflammatory diseases such as asthma and other respiratory diseases, cardiovascular diseases |
| influenza virus genes such as NP, PA, PB1, PB2, M, NS | Influenza virus infection |
| NOGO & NOGO Receptors | spinal cord injury |
| p38 | Inflammation |
| PTP-1B | Cardiovascular, diabetes, obesity |
| Retinoblastoma 1 | Hearing loss |
| RSV (Respiratory syncytial virus) targets such as P gene, nucleocapsid (N), NS1 | RSV infection |
| NGF, BDGF, PDGF and their receptors HER2, BRAC1 and BRAC2, RAS, RAF, Myc, SRC | Cancers |
| HBV (Hepatitis B virus) targets such as HBsAg | HBV infection |
| HCV (Hepatitis C virus) targets such as the 5' untranslated region (UTR), E2, HCV core, NS3, NS4B, and NS5B | HCV infection |
| HIV (Human Immunodeficiency Virus) targets such as nef, vif, gag (MA, CA, SP1, NC, SP2, P6), pol (RT, IN, PR), env (gp120, gp41), tat, rev, vpr, vpu | HIV infection, e.g., having a neurological component |

Provided with a target gene, such as a target gene in Table 2, the skilled artisan can select or design the specific polynucleotide sequences of an siRNA molecule according to a variety of techniques in the art. As one example, the skilled artisan can scan for AA dinucleotide sequences and select each AA and the 3' adjacent 19 nucleotides as potential siRNA target sites. This strategy for choosing siRNA target sites is based on the observation by Elbashir et al. (EMBO J 20: 6877-6888, 2001) that siRNA molecules with 3' overhanging UU dinucleotides are highly effective. Particular target sequences can then be selected, for example, by identifying siRNAs with 30-50% GC content, and/or by comparing the potential target sites to the appropriate genome database (human, mouse, rat, etc.) and eliminating from consideration any target sequences with more than 16-17 contiguous base pairs of homology to other coding sequences. A variety of software tools are also available for generating specific siRNA target sites in any given gene. See also Birmingham et al., Nat Protoc. 2:2068-78, 2007; and U.S. Pat. Nos. 7,056,704; 7,078,196; 8,101,348; 8,394,628; 8,420,391; 8,445,237; and 8,552,171, incorporated by reference in their entireties.

In specific embodiments, the target gene is a NOX (NADPH Oxidase) gene such as NOX1 (NADPH oxidase 1), NOX2 (NADPH oxidase 2; Cytochrome b-245 heavy chain) and/or NOX4 (NADPH oxidase 4). NOX enzymes are superoxide producing transmembrane proteins. NOX enzymes are expressed in many cell types and tissues. However, there is increasing evidence that overactivation of NOX enzymes may contribute to CNS-associated and other diseases. Hence, certain conjugates comprise an siRNA molecule, where the antisense strand is fully or substantially complementary to a NOX1 sequence (see, e.g., Accession: AJ438989.1; Accession: NM_007052.4; Accession: NM_013955.2, Accession: NM_001271815.1), a NOX2 sequence (see, e.g., Accession: NM_000397.3) and/or a NOX4 target sequence (see, e.g., Accession: NM_001143837.1; Accession: NM_001143836.1; Accession: NM_016931.3; Accession: AY288918.1). In specific embodiments, the siRNA molecule comprises or consists of 5'-A UGU UCA CAA AGU CAG GUC TT-3' (SEQ ID NO:31) and/or 5'-GAC CUG ACU UUG UGA ACA UTT-3' (SEQ ID NO:32) (see Example 1).

In particular embodiments, the target is a microRNA (miRNA). Non-limiting examples of miRNA targets include miRNA-132, the inhibition of which prevented angiogenesis in an orthotopic mouse model of ovarian and breast carcinoma, and miRNA-21, the inhibition of which led to regression of malignant pre-B-lymphoid tumors. In some embodiments, the antisense strand is at least 75% complementary, at least 80% complementary, at least 90% complementary, at least 95% complementary, or 100% complementary to a target miRNA sequence. In particular embodiments, the antisense strand is fully or substantially complementary to a target miRNA sequence. Likewise, in some embodiments, the sense strand of the siRNA molecule is fully or substantially identical to a target miRNA sequence. In some embodiments, the sense strand has at least 75% identity, at least 80% identity, at least 90% identity, at least 95% identity, or 100% identity to a target miRNA sequence.

In certain embodiments, the siRNA molecule or one or both of the polynucleotide strands of the siRNA are synthetic oligonucleotides.

Figure 5A:
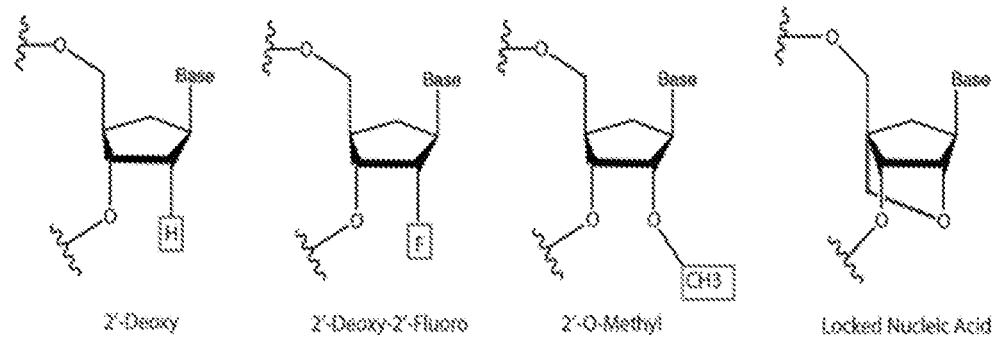
FIGS. 5A-5B show exemplary modifications to the sugar (5A) and nucleobase (5B) chemistries of siRNA molecules.
Figure 5A:
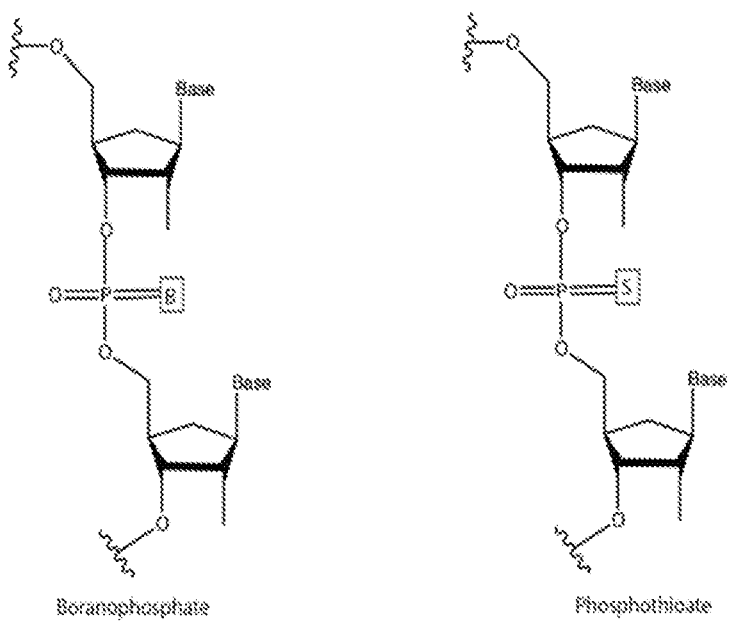
Figure 5B:
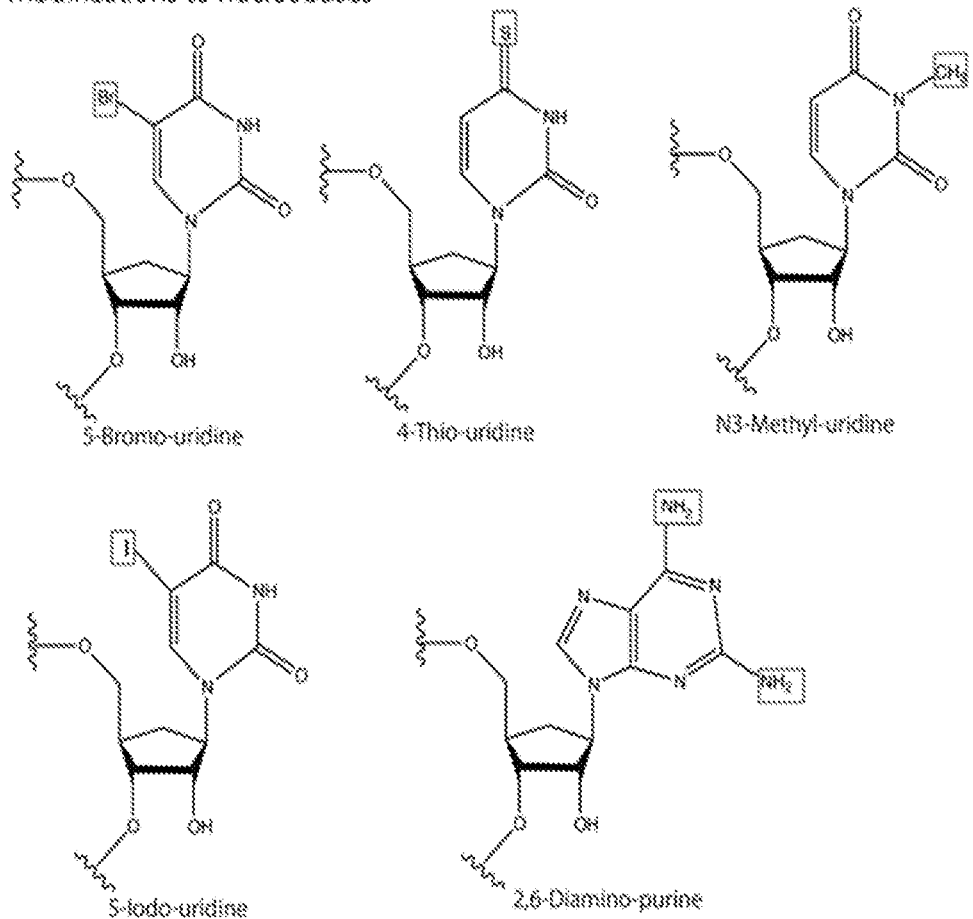

Certain embodiments employ modified siRNA molecules. Examples include the incorporation of nucleotide analogs having modifications in the chemical structure of the base, sugar and/or phosphate (see, e.g., FIG. 5), including, but not limited to, 5-position pyrimidine modifications, 8-position purine modifications, modifications at cytosine exocyclic amines, and substitution of 5-bromo-uracil; and 2'-position sugar modifications, including but not limited to, sugar-modified ribonucleotides in which the 2'-OH is replaced by a group such as an H, OR, R, halo, SH, SR, NH$_2$, NHR, NR$_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as methylphosphonates, phosphorothioates and peptides.

Also included are 2'-fluoro, 2'-amino and/or 2'-thio modifications. Particular examples include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thiouridine; and/or 5-amino-allyl-uridine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides can be used within modified siRNAs of this invention, but are preferably included within the sense strand of the siRNA duplex. Additional modified residues have been described in the art and are commercially available including, deoxy-abasic, inosine, N3-methyl-uridine, N6,N6-dimethyl-adenosine, pseudouridine, purine ribonucleoside and ribavirin.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any 0- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

Modifications include substitutions with alkyl, alkoxy, amino, deaza, halo, hydroxyl, thiol groups, or a combination thereof, for example. Nucleotides may be substituted with analogs with greater stability such as replacing a ribonucleotide with a deoxyribonucleotide, or having sugar modifications such as 2' OH groups replaced by 2' amino groups, 2' O-methyl groups, 2' methoxyethyl groups, or a 2-O, 4'-C methylene bridge, for example. Examples of a purine or pyrimidine analog of nucleotides include a xanthine, a hypoxanthine, an azapurine, a methylthioadenine, 7-deaza-adenosine and O- and N-modified nucleotides.

Modification of the linkage between nucleotides or nucleotide analogs is also preferred, e.g., substitution of phosphorothioate linkages for phosphodiester linkages. The phosphate group of the nucleotide may be modified by substituting one or more of the oxygens of the phosphate group with nitrogen or with sulfur (phosphorothioates). Modifications are useful, for example, to enhance function, to improve stability or permeability, or to direct localization or targeting.

Linkers. As noted above, certain conjugates may employ one or more linker groups. The term "linkage," "linker," "linker moiety," or "l" is used herein to refer to a linker that can be used to separate a p97 polypeptide from an agent (e.g., a strand of an siRNA molecule), or to separate a first agent from another agent or label (fluorescence label), for instance where two or more agents are linked to form a p97 conjugate. The linker may be physiologically stable or may include a releasable linker such as a labile linker or an enzymatically degradable linker (e.g., proteolytically cleavable linkers). In certain aspects, the linker may be a peptide linker. In some aspects, the linker may be a non-peptide linker or non-proteinaceous linker. In some aspects, the linker may be particle, such as a nanoparticle.

The linker may be charge neutral or may bear a positive or negative charge. A reversible or labile linker contains a reversible or labile bond. A linker may optionally include a spacer that increases the distance between the two joined atoms. A spacer may further add flexibility and/or length to the linker. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides.

A labile bond is a covalent bond other than a covalent bond to a hydrogen atom that is capable of being selectively broken or cleaved under conditions that will not break or cleave other covalent bonds in the same molecule. More specifically, a labile bond is a covalent bond that is less stable (thermodynamically) or more rapidly broken (kinetically) under appropriate conditions than other non-labile covalent bonds in the same molecule. Cleavage of a labile bond within a molecule may result in the formation of two molecules. For those skilled in the art, cleavage or lability of a bond is generally discussed in terms of half-life ($t_{1/2}$) of bond cleavage (the time required for half of the bonds to cleave). Thus, labile bonds encompass bonds that can be selectively cleaved more rapidly than other bonds a molecule.

Appropriate conditions are determined by the type of labile bond and are well known in organic chemistry. A labile bond can be sensitive to pH, oxidative or reductive conditions or agents, temperature, salt concentration, the presence of an enzyme (such as esterases, including nucleases, and proteases), or the presence of an added agent. For example, increased or decreased pH is the appropriate conditions for a pH-labile bond.

In some embodiments, the linker is an organic moiety constructed to contain an alkyl, aryl and/or amino acid backbone, and containing an amide, ether, ester, hydrazone, disulphide linkage or any combination thereof. Linkages containing amino acid, ether and amide bound components are stable under conditions of physiological pH, normally 7.4 in serum. As above, also included are linkages that contain esters or hydrazones and are stable at serum pH, but which hydrolyze to release the siRNA molecule when exposed to lysosomal pH. Disulphide linkages are also included, at least in part because they are sensitive to reductive cleavage. In addition, amino acid linkers may be designed to be sensitive to cleavage by specific enzymes in the desired target organ or, for example, in the lysosome. Exemplary linkers are described in Blattler et al. (19S5) Biochem. 24:1517-1524; King et al (1986) Biochem. 25:5774-5779; Srinivasachar and Nevill (1989) Biochem. 28:2501-2509, and elsewhere (see also FIG. 2).

In some embodiments, the linker is about 1 to about 30 atoms in length, or about 1, 2, 3, 4, 5, 6, 7, 8, 9, 0, 11, 12, 13, 14, 15, 16, 17, 18, 19, 20, 21, 22, 23, 24, 25, 26, 27, 28, 29, or 30 atoms in length, including all ranges in between. In certain embodiments, the linker is about 1 to 30 atoms in length with carbon chain atoms which may be substituted by heteroatoms independently selected from the group consisting of O, N. or S. In some embodiments, from 1-4 or from 5 to 15 of the C atoms are substituted with a heteroatom independently selected from O, N, S.

In certain embodiments, the linker comprises or consists of a structure selected from the following: —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —CH$_2$—CH$_2$—CH$_2$—CH$_2$—C(O)—NH—, —NH—C(O)—CH$_2$—, —CH$_2$—NH—C(O)—CH$_2$—, —CH$_2$—CH$_2$—NH—C(O)—CH$_2$—, —CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

In some embodiments, the linker comprises a releasable linker. In some embodiments, the releasable linker is selected from the group consisting of: carboxylate ester, phosphate ester, anhydride, acetal, ketal, acyloxyalkyl ether, imine, orthoester, thio ester, thiol ester, carbonate, and hydrazone. In certain embodiments, the linker contains a moiety subject to hydrolysis upon delivery to the lysosomal environment (e.g., susceptible to hydrolysis at the lysosomal pH or upon contact to a lysosomal enzyme).

In some embodiments, the linker comprises a stable linker. In some embodiments, the stable linkage is selected from the group consisting of: succinimide, propionic acid, carboxymethylate linkages, ethers, carbamates, amides, amines, carbamides, imides, aliphatic C—C bonds, and thio ethers.

In some embodiments, the linker comprises or consists of polymer such as a polyethylene glycol or polypropylene glycol. The terms "PEG," "polyethylene glycol" and "poly (ethylene glycol)" as used herein, are interchangeable and meant to encompass any water-soluble poly(ethylene oxide) derivative. PEG is a well-known polymer with good solubility in many aqueous and organic solvents, which exhibits low toxicity, lack of immunogenicity, and is clear, colorless, odorless, and stable. Similar products may be obtained with other water-soluble polymers, as described herein, including without limitation; polyvinyl alcohol, other poly(alkylene oxides) such as poly(propylene glycol) and the like, poly (oxyethylated polyols) such as poly(oxyethylated glycerol) and the like, carboxymethylcellulose, dextran, polyvinyl alcohol, polyvinyl purrolidone, poly-1,3-dioxolane, poly-1, 3,6-trioxane, ethylene/maleic anhydride, and polyaminoacids. One skilled in the art will be able to select the desired polymer based on the desired dosage, circulation time, resistance to proteolysis, and other considerations.

Typically, PEGs for use in accordance with the conjugates described herein comprise the following structure "—(OCH2CH2)n-" where (n) is about 1 to 4000, about 20 to 1400, or about 20-800. In particular embodiments, PEG also includes "—O—(CH2CH2O)n-CH2CH2-" and "—(OCH2CH2)n-O—" depending upon whether or not the terminal oxygens have been displaced. The term "PEG" includes structures having various terminal or "end capping" groups. The term "PEG" also includes a polymer that contains a majority, that is to say, greater than 50%, of —OCH2CH2- repeating subunits. With respect to specific forms, the PEG can take any number of a variety of molecular weights, as well as structures or geometries such as "branched," "linear," "forked," "multifunctional" PEG molecules.

Representative polymeric reagents and methods for conjugating such polymers to an active moiety are described in Harris, J. M. and Zalipsky, S., Eds, Poly(ethylene glycol), Chemistry and Biological Applications, ACS, Washington, 1997; Veronese, F., and J. M. Harris, Eds., Peptide and Protein PEGylation, Advanced Drug Delivery Reviews, 54(4); 453-609 (2002); Zalipsky, S., et al., "Use of Functionalized Poly Ethylene Glycols) for Modification of Polypeptides" in Polyethylene Glycol Chemistry: Biotechnical and Biomedical Applications, J. M. Harris, ed., Plenus Press, New York (1992); Zalipsky (1995) Advanced Drug Reviews 16:157-182; and in Roberts et al., Adv. Drug Delivery Reviews, 54, 459-476 (2002).

A wide variety of PEG derivatives are both commercially available and suitable for use in the preparation of the PEG-conjugates of the invention. For example, NOF Corp.'s SUNBRIGHT® Series provides numerous PEG derivatives, including methoxypolyethylene glycols and activated PEG derivatives such as succinimidyl ester, methoxy-PEG amines, maleimides, and carboxylic acids, for coupling by various methods to polypeptides and polynucleotides and Nektar Therapeutics' Advanced PEGylation also offers diverse PEG-coupling technologies to improve the safety and efficacy of therapeutics. Additional PEGs for use in forming a p97-siRNA conjugate include those available from Polypure (Norway), from QuantaBioDesign LTD (Ohio) JenKem Technology, Nanocs Corporation, and Sunbio, Inc (South Korea). Further PEG reagents suitable for use in forming a conjugate, and methods of conjugation are described, for example, in Pasut et al., Expert Opin. Ther. Patents. 14(6) 859-893, 2004.

The preparation of linear or branched PEG polymers and derivatives or conjugates thereof is described, for example, in U.S. Pat. Nos. 4,904,584; 5,428,128; 5,621,039; 5,622, 986; 5,643,575; 5,728,560; 5,730,990; 5,738,846; 5,811, 076; 5,824,701; 5,840,900; 5,880,131; 5,900,402; 5,902, 588; 5,919,455; 5,951,974; 5,965,119; 5,965,566; 5,969, 040; 5,981,709; 6,011,042; 6,042,822; 6,113,906; 6,127, 355; 6,132,713; 6,177,087; 6,180,095; 6,448,369; 6,495, 659; 6,602,498; 6,858,736; 6,828,401; 7,026,440; 7,608, 678; 7,655,747; 7,786,221; 7,872,072; and 7,910,661, each of which is incorporated herein by reference in its entirety.

In some embodiments, the linker group is hydrophilic, for instance, to enhance the solubility of the conjugate in body fluids. In some embodiments, the p97 polypeptide and siRNA molecule are joined by a linker comprising amino acids or peptides, lipids, or sugar residues. In some embodiments, the p97 polypeptide and siRNA molecule are joined at groups introduced synthetically or by posttranslational modifications.

Variant Sequences. Certain embodiments include variants of the reference polypeptide and polynucleotide sequences described herein, whether described by name or by reference to a sequence identifier, including p97 sequences, IDS sequences, linker sequences, signal peptide sequences, purification tags, and protease sites (see, e.g., Tables 1-6 and the Sequence Listing). The wild-type or most prevalent sequences of these polypeptides are known in the art, and can be used as a comparison for the variants and fragments described herein.

A "variant" sequence, as the term is used herein, refers to a polypeptide or polynucleotide sequence that differs from a reference sequence disclosed herein by one or more substitutions, deletions (e.g., truncations), additions, and/or insertions. Certain variants thus include fragments of a reference sequence described herein. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table A below.

TABLE A

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take one or more of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gLn, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, variants of the DSSHAFTLDELR (SEQ ID NO:14) p97 polypeptide can be based on the sequence of p97 sequences from other organisms, as shown in Table B below. Variant amino acids relative to the human sequence are underlined.

TABLE B

| Common Name | Species | Protein Name | % Identity | Sequence | SEQ ID NO: |
|---|---|---|---|---|---|
| Human | Homo Sapien | Melanotransferrin | 100% | DSSHAFTLDELR | 14 |
| Black-capped squirrel monkey | Saimiri boliviensis boliviensis | Melanotransferrin | 100% | DSSHAFTLDELR | 14 |
| Bonobo | Pan paniscus | Melanotransferrin | 100% | DSSHAFTLDELR | 14 |
| Chimpanzee | Pan troglodytes | Melanotransferrin | 100% | DSSHAFTLDELR | 14 |
| Crab-eating macaque | Macaca fascicularis | hypothetical protein | 100% | DSSHAFTLDELR | 14 |

TABLE B-continued

| Common Name | Species | Protein Name | % Identity | Sequence | SEQ ID NO: |
|---|---|---|---|---|---|
| Northern white-cheeked gibbon | Nomascus leucogenys | Melanotransferrin | 100% | DSSHAFTLDELR | 14 |
| Olive baboon | Papio anubis | Melanotransferrin | 100% | DSSHAFTLDELR | 14 |
| Rhesus macaque | Macaca mulatta | hypothetical protein | 100% | DSSHAFTLDELR | 14 |
| Rhesus macaque | Macaca mulatta | hypothetical protein | 100% | DSSHAFTLDELR | 14 |
| Western lowland gorilla | Gorilla gorilla gorilla | Melanotransferrin | 100% | DSSHAFTLDELR | 14 |
| White-tufted-ear marmoset | Callithrix jacchus | Melanotransferrin | 100% | DSSHAFTLDELR | 14 |
| Lesser Egyptian jerboa | Jaculus jaculus | Melanotransferrin | 92% | DSSDAFTLDELR | 33 |
| Northern greater galago | Otolemur garnettii | Melanotransferrin | 92% | DSSHSFTLDELR | 34 |
| Sumatran orangutan | Pongo abelii | Melanotransferrin | 92% | DSSDAFTLDELR | 33 |
| Thirteen-lined ground squirrel | Ictidomys tridecemlineatus | Melanotransferrin | 92% | DSSYAFTLDELR | 35 |
| white rhinoceros | Ceratotherium simum simum | Melanotransferrin | 92% | NSSHAFTLDELR | 36 |
| alpaca | Vicugna pacos | Melanotransferrin | 83% | NSSYAFTLDELR | 37 |
| American pika | Ochotona princeps | Melanotransferrin | 83% | DSSYAFPLDELR | 38 |
| black flying fox | Pteropus alecto | Melanotransferrin | 83% | NSSYAFTLDELR | 37 |
| bottlenosed dolphin | Tursiops truncatus | Melanotransferrin | 83% | NSSYAFTLDELR | 37 |
| Chinese tree shrew | Tupaia chinensis | Melanotransferrin | 83% | DSTHAFTVDELR | 39 |
| Chiru | Pantholops hodgsonii | Melanotransferrin | 83% | NSSYAFTLDELR | 37 |
| Domestic cat | Felis catus | Melanotransferrin | 83% | NSSYAFTLDELR | 37 |
| Domestic cattle | Bos taurus | Melanotransferrin | 83% | NSSYAFTLDELR | 37 |
| Domestic ferret | Mustela putorius furo | Melanotransferrin | 83% | NSSYAFTLDELR | 37 |
| Giant panda | Ailuropoda Melanoleuca | Melanotransferrin | 83% | NSSYAFTLDELR | 37 |
| Goat | Capra hircus | Melanotransferrin | 83% | NSSYAFTLDELR | 37 |
| House mouse | Mus musculus | Melanotransferrin | 83% | DSSYSFTLDELR | 40 |

TABLE B-continued

| Common Name | Species | Protein Name | % Identity | Sequence | SEQ ID NO: |
|---|---|---|---|---|---|
| Killer whale | Orcinus orca | Melanotransferrin | 83% | NSSNAFTLDELR | 41 |
| Long-tailed chinchilla | Chinchilla lanigera | Melanotransferrin | 83% | DSSSAFTLNELR | 42 |
| Nine-banded armadillo | Dasypus novemcinctus | Melanotransferrin | 83% | DSSYAFTLDELW | 43 |
| Norway rat | Rattus norvegicus | Melanotransferrin | 83% | DSSYSFTLDELR | 40 |
| Pacific walrus | Odobenus rosmarus divergens | Melanotransferrin | 83% | NSSSAFTLDELR | 44 |
| Prairie vole | Microtus ochrogaster | Melanotransferrin | 83% | DSSYSFTLDELR | 40 |
| Sheep | Ovis aries | Melanotransferrin | 83% | NSSYAFTLDELR | 37 |
| Weddell seal | Leptonychotes weddellii | Melanotransferrin | 83% | NSSYAFTLDELR | 37 |
| Wild Bactrian camel | Camelus ferus | Melanotransferrin | 83% | NSSYAFTLDELR | 37 |
| Wild boar | Sus scrofa | Melanotransferrin | 83% | NSSYAFTLDELR | 37 |
| Yak | Bos mutus | Melanotransferrin | 83% | NSSYAFTLDELR | 37 |
| (Fungus) | Cyphellophora europaea | hypothetical protein | 75% | ATSHAITLDELR | 45 |
| African savanna elephant | Loxodonta africana | Melanotransferrin | 75% | NSSYAFTMDELR | 46 |
| Chinese hamster | Cricetulus griseus | Melanotransferrin | 75% | DRSYSFTLDELR | 47 |
| Common rabbit | Oryctolagus cuniculus | Melanotransferrin | 75% | DSAYAFTVDELR | 48 |
| Degu | Octodon degus | Melanotransferrin | 75% | DSSSAFNLNELR | 49 |
| Domestic Dog | Canis lupus familiaris | Melanotransferrin | 75% | NSSDAFSLDELR | 50 |
| Domestic guinea pig | Cavia porcellus | Melanotransferrin | 75% | DSSSAFSLNELR | 49 |
| European shrew | Sorex araneus | Melanotransferrin | 75% | NSSDAFSLDELR | 50 |
| Florida manatee | Trichechus manatus latirostris | Melanotransferrin | 75% | NSSYAFTMDELR | 46 |
| Golden hamster | Mesocricetus auratus | Melanotransferrin | 75% | DRSYSFTLDELR | 47 |
| Gray short-tailed opossum | Monodelphis domestica | Melanotransferrin | 75% | NSSYSFTLDELR | 51 |
| Horse | Equus caballus | Melanotransferrin | 75% | NSSYAFTVDELR | 52 |
| Small Madagascar hedgehog | Echinops telfairi | Melanotransferrin | 75% | NSSYAFTVDELR | 52 |

TABLE B-continued

| Common Name | Species | Protein Name | % Identity | Sequence | SEQ ID NO: |
|---|---|---|---|---|---|
| Star-nosed mole | Condylura cristata | Melanotransferrin | 75% | NSSYAFSLDELR | 53 |
| Human | Homo sapien | Transferrin | 33% | SASD_LTWDNLK | 54 |
| Human | Homo sapien | Lactoferrin | 17% | _SDTSLTWNSVK | 55 |

Hence, in certain embodiments, the p97 peptide comprises, consists, or consists essentially of a sequence in Table B. In specific aspects, the p97 peptide retains the short alpha-helix (LDEL) at the C-terminus of the DSSHAFTLDELR (SEQ ID NO:14) peptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700. 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Sequence Listing).

In certain embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Sequence Listing).

In some embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases, for example, to identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA.* 89:10915-10919, 1992). GAP uses the algorithm of Needleman and Wunsch (*J Mol Biol.* 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA.* 82:

488-492, 1985); Kunkel et al., (*Methods in Enzymol.* 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering.* 6: 327-331, 1993).

Detectable Entities. In some embodiments, the p97 conjugate is operatively linked to a "detectable entity." Exemplary detectable entities include, without limitation, iodine-based labels, radioisotopes, fluorophores/fluorescent dyes, and nanoparticles.

Exemplary iodine-based labels include diatrizoic acid (Hypaque®, GE Healthcare) and its anionic form, diatrizoate. Diatrizoic acid is a radio-contrast agent used in advanced X-ray techniques such as CT scanning. Also included are iodine radioisotopes, described below.

Exemplary radioisotopes that can be used as detectable entities include $^{32}P$, $^{33}P$, $^{35}S$, $^{3}H$, $^{18}F$, $^{11}C$, $^{13}N$, $^{15}O$, $^{111}In$, $^{169}Yb$, $^{99m}Tc$, $^{55}Fe$, and isotopes of iodine such as $^{123}I$, $^{124}I$, $^{125}I$, and $^{131}I$. These radioisotopes have different half-lives, types of decay, and levels of energy which can be tailored to match the needs of a particular protocol. Certain of these radioisotopes can be selectively targeted or better targeted to CNS tissues by conjugation to p97 conjugates, for instance, to improve the medical imaging of such tissues.

Examples of fluorophores or fluorochromes that can be used as directly detectable entities include fluorescein, tetramethylrhodamine, Texas Red, Oregon Green®, and a number of others (e.g., Haugland, *Handbook of Fluorescent Probes*—9th Ed., 2002, Molec. Probes, Inc., Eugene Oreg.; Haugland, *The Handbook: A Guide to Fluorescent Probes and Labeling Technologies*—10th Ed., 2005, Invitrogen, Carlsbad, Calif.). Also included are light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-($\epsilon$-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy2; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750. Certain embodiments include conjugation to chemotherapeutic agents (e.g., paclitaxel, adriamycin) that are labeled with a detectable entity, such as a fluorophore (e.g., Oregon Green®, Alexa Fluor 488).

Nanoparticles usually range from about 1-1000 nm in size and include diverse chemical structures such as gold and silver particles and quantum dots. When irradiated with angled incident white light, silver or gold nanoparticles ranging from about 40-120 nm will scatter monochromatic light with high intensity. The wavelength of the scattered light is dependent on the size of the particle. Four to five different particles in close proximity will each scatter monochromatic light, which when superimposed will give a specific, unique color. Derivatized nanoparticles such as silver or gold particles can be attached to a broad array of molecules including, proteins, antibodies, small molecules, receptor ligands, and nucleic acids. Specific examples of nanoparticles include metallic nanoparticles and metallic nanoshells such as gold particles, silver particles, copper particles, platinum particles, cadmium particles, composite particles, gold hollow spheres, gold-coated silica nanoshells, and silica-coated gold shells. Also included are silica, latex, polystyrene, polycarbonate, polyacrylate, PVDF nanoparticles, and colored particles of any of these materials.

Quantum dots are fluorescing crystals about 1-5 nm in diameter that are excitable by light over a large range of wavelengths. Upon excitation by light having an appropriate wavelength, these quantum dots emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, Ark.; Ocean Nanotech, Fayetteville, Ark.; Nanoco Technologies, Manchester, UK; Sigma-Aldrich, St. Louis, Mo.).

Methods of Use and Pharmaceutical Compositions

Certain embodiments of the present invention relate to methods of using the p97 conjugates described herein. Examples of such methods include methods of treatment and methods of diagnosis, including for instance, the use of p97 conjugates for medical imaging of certain organs/tissues, such as those of the nervous system. Some embodiments include methods of diagnosing and/or treating disorders or conditions of the central nervous system (CNS), or disorders or conditions having a CNS component. Particular aspects include methods of treating a lysosomal storage disorder (LSD), including those having a CNS component.

Accordingly, certain embodiments include methods of treating a subject in need thereof, comprising administering a p97 conjugate described herein. Also included are methods of delivering an IDS enzyme to the nervous system (e.g., central nervous system tissues) of a subject, comprising administering a composition that comprises a p97 conjugate described herein. In certain of these and related embodiments, the methods increase the rate of delivery of the agent to the central nervous system tissues, relative, for example, to delivery by a composition that comprises an unconjugated siRNA molecule.

In certain embodiments, the subject has a disease or condition in Table 2. In specific embodiments, the siRNA molecule is targeted against a NOX gene such as NOX1, NOX2 and/or NOX4, and the subject has a disease or condition such as a disease associated with cell death, chronic kidney disease, diabetes or diabetic complications such as diabetic nephropathy (see, e.g., Jha et al., J Am Soc Nephrol. 2014), a neurocardiovascular disease such as myocardial infarction-induced cardiac dysfunction, or a disorder of the CNS (see, e.g., Nayernia et al., Antioxidants & Redox Signaling, doi:10.1089/ars.2013.5703, 2014; Sorce and Krause, Antioxidants & Redox Signaling. 11: 2481-2504, 2009. Particular examples include neurodegenerative diseases, for example, where activation of NOX enzymes in microglia generate a pathological cycle of cell damage leading to increased microglia activation, which leads to further cell damage and so on. Also included is Parkinson's disease, for example, where NOX (e.g., NOX1) expression in dopaminergic neurons could contribute to neurodegeneration.

Also included is the treatment of NOX-associated psychiatric diseases. For example, NOX2 is increasingly implicated in animal models of psychotic disease, in particular in ketamine-induced psychosis. Here, there is evidence that disease-relevant NOX2 activity might be in neurons, and not exclusively be restricted to microglia. Particular examples include Acute Stress Disorder; Adjustment Disorder Unspecified; Adjustment Disorder with Anxiety; Adjustment Disorder with Depressed Mood; Adjustment Disorder with Disturbance of Conduct; Adjustment Disorder with Mixed Anxiety and Depressed Mood; Adjustment Disorder with Mixed Disturbance of Emotions and Conduct; Agoraphobia without History of Panic Disorder; Anorexia Nervosa; Antisocial Personality Disorder; Anxiety Disorder Due to Medical Condition; Anxiety Disorder, NOS; Avoidant Personality Disorder; Bipolar Disorder NOS; Bipolar I Disorder, Most Recent Episode Depressed, In Full Remission; Bipolar I Disorder, Most Recent Episode Depressed, In Partial Remission; Bipolar I Disorder, Most Recent Episode Depressed, Mild; Bipolar I Disorder, Most Recent Episode Depressed, Moderate; Bipolar I Disorder, Most Recent Episode Depressed, Severe With Psychotic Features; Bipolar I Disorder, Most Recent Episode Depressed, Severe Without Psychotic Features; Bipolar I Disorder, Most Recent Episode Depressed, Unspecified; Bipolar I Disorder, Most Recent Episode Manic, In Full Remission; Bipolar I Disorder, Most Recent Episode Manic, In Partial Remission; Bipolar I Disorder, Most Recent Episode Manic, Mild; Bipolar I Disorder, Most Recent Episode Manic, Moderate; Bipolar I Disorder, Most Recent Episode Manic, Severe With Psychotic Features; Bipolar I Disorder, Most Recent Episode Manic, Severe Without Psychotic Features; Bipolar I Disorder, Most Recent Episode Manic, Unspecified; Bipolar I Disorder, Most Recent Episode Mixed, In Full Remission; Bipolar I Disorder, Most Recent Episode Mixed, In Partial Remission; Bipolar I Disorder, Most Recent Episode Mixed, Mild; Bipolar I Disorder, Most Recent Episode Mixed, Moderate; Bipolar I Disorder, Most Recent Episode Mixed, Severe With Psychotic Features; Bipolar I Disorder, Most Recent Episode Mixed, Severe Without Psychotic Features; Bipolar I Disorder, Most Recent Episode Mixed, Unspecified; Bipolar I Disorder, Most Recent Episode Unspecified; Bipolar I Disorder, Most Recent Episode Hypomanic; Bipolar I Disorder, Single Manic Episode, In Full Remission; Bipolar I Disorder, Single Manic Episode, In Partial Remission; Bipolar I Disorder, Single Manic Episode, Mild; Bipolar I Disorder, Single Manic Episode, Moderate; Bipolar I Disorder, Single Manic Episode, Severe With Psychotic Features; Bipolar I Disorder, Single Manic Episode, Severe Without Psychotic Features; Bipolar I Disorder, Single Manic Episode, Unspecified; Bipolar II Disorder; Body Dysmorphic Disorder; Borderline Personality Disorder; Breathing-Related Sleep Disorder; Brief Psychotic Disorder; Bulimia Nervosa; Circadian Rhythm Sleep Disorder; Conversion Disorder; Cyclothymic Disorder; Delusional Disorder; Dependent Personality Disorder; Depersonalization Disorder; Depressive Disorder NOS; Dissociative Amnesia; Dissociative Disorder NOS; Dissociative Fugue; Dissociative Identity Disorder; Dyspareunia; Dyssomnia NOS; Dyssomnia Related to (Another Disorder); Dysthymic Disorder; Eating Disorder NOS; Exhibitionism; Female Dyspareunia Due to Medical Condition; Female Hypoactive Sexual Desire Disorder Due to Medical Condition; Female Orgasmic Disorder; Female Sexual Arousal Disorder; Fetishism; Frotteurism; Gender Identity Disorder in Adolescents or Adults; Gender Identity Disorder in Children; Gender Identity Disorder NOS; Generalized Anxiety Disorder; Histrionic Personality Disorder; Hypoactive Sexual Desire Disorder; Hypochondriasis; Impulse—Control Disorder NOS; Insomnia Related to (Another Disorder); Intermittent Explosive Disorder; Kleptomania; Major Depressive Disorder, Recurrent, In Full Remission; Major Depressive Disorder, Recurrent, In Partial Remission; Major Depressive Disorder, Recurrent, Mild; Major Depressive Disorder, Recurrent, Moderate; Major Depressive Disorder, Recurrent, Severe With Psychotic Features; Major Depressive Disorder, Recurrent, Severe Without Psychotic Features; Major Depressive Disorder, Recurrent, Unspecified; Major Depressive Disorder, Single Episode, In Full Remission; Major Depressive Disorder, Single Episode, In Partial Remission; Major Depressive Disorder, Single Episode, Mild; Major Depressive Disorder, Single Episode, Moderate; Major Depressive Disorder, Single Episode, Severe With Psychotic Features; Major Depressive Disorder, Single Episode, Severe Without Psychotic Features; Major Depressive Disorder, Single Episode, Unspecified; Male Dyspareunia Due to Medical Condition; Male Erectile Disorder; Male Erectile Disorder Due to Medical Condition; Male Hypoactive Sexual Desire Disorder Due to Medical Condition; Male Orgasmic Disorder; Mood Disorder Due to Medical Condition; Narcissistic Personality Disorder; Narcolepsy; Nightmare Disorder; Obsessive Compulsive Disorder; Obsessive-Compulsive Personality Disorder; Other Female Sexual Dysfunction Due to Medical Condition; Other Male Sexual Dysfunction Due to Medical Condition; Pain Disorder Associated with both Psychological Factors and Medical Conditions; Pain Disorder Associated with Psychological Features; Panic Disorder with Agoraphobia; Panic Disorder without Agoraphobia; Paranoid Personality Disorder; Paraphilia, NOS; Parasomnia NOS; Pathological Gambling; Pedophilia; Personality Disorder NOS; Posttraumatic Stress Disorder; Premature Ejaculation; Primary Hypersomnia; Primary Insomnia; Psychotic Disorder Due to Medical Condition, with Delusions; Psychotic Disorder Due to Medical Condition, with Hallucinations; Psychotic Disorder, NOS; Pyromania; Schizoaffective Disorder; Schizoid Personality Disorder; Schizophrenia, Catatonic Type; Schizophrenia, Disorganized Type; Schizophrenia, Paranoid Type; Schizophrenia, Residual Type; Schizophrenia, Undifferentiated Type; Schizophreniform Disorder; Schizotypal Personality Disorder; Sexual Aversion Disorder; Sexual Disorder NOS; Sexual Dysfunction NOS; Sexual Masochism; Sexual Sadism; Shared Psychotic Disorder; Sleep Disorder Due to A Medical Condition, Hypersomnia Type; Sleep Disorder Due to A Medical Condition, Insomnia Type; Sleep Disorder Due to A Medical Condition, Mixed Type; Sleep Disorder Due to A Medical Condition, Parasomnia Type; Sleep Terror Disorder; Sleepwalking Disorder; Social Phobia; Somatization Disorder; Somatoform Disorder NOS; Specific Phobia Also included is the treatment of ischemia or stroke. There is abundant evidence that NOX-deficient mice are protected from stroke. Both neuronal and microglial NOX might play a role. Experimental evidence in favor of NOX2 and NOX4 has been demonstrated (see Radermacher et al., Antioxid Redox Signal. 18:1418-27, 2013; Suzuki et al., Sci Rep. 2:896, 2012). Also included is the treatment of CNS trauma. There is evidence that CNS trauma can lead to long lasting microglia activation and NOX2 expression. This mechanism is thought to contribute to neurodegeneration following CNS trauma. Molecular targeting of NOX4 has also been shown to improve neuropathic pain following peripheral nerve injury such as traumatic injury of the spinal cord (see Im et al., Cell Death Dis. 3:e426, 2012).

Certain embodiments include the treatment of neurodegenerative disorders, such as nerve inflammation, certain types of cancers, multiple sclerosis (MS), amyotrophic lateral sclerosis (ALS), Parkinson's disease, Alzheimer's disease, Friedreich's ataxia, spinal muscular atrophy, Huntington's disease, Dementia with Lewy bodies, spinal muscular atrophy, neuromyelitis optica, major depressive disorder, schizophrenia, glaucoma or peripheral neuropathies (diabetic or AIDS neuropathy).

Also included is the treatment of diseases of the central and peripheral nervous system. Particular examples include Absence of the Septum Pellucidum, Acid Lipase Disease, Acid Maltase Deficiency, Acquired Epileptiform Aphasia, Acute Disseminated Encephalomyelitis, Adie's Pupil, Adie's Syndrome, Adrenoleukodystrophy, Agenesis of the Corpus Callosum, Agnosia, Aicardi Syndrome, Aicardi-Goutieres Syndrome Disorder, AIDS—Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Antiphospholipid Syndrome, Aphasia, Apraxia, Arachnoid Cysts, Arachnoiditis, Arnold-Chiari Malformation, Arteriovenous Malformation, Asperger Syndrome, Ataxia, Ataxia Telangiectasia, Ataxias and Cerebellar or Spinocerebellar Degeneration, Atrial Fibrillation and Stroke, Attention Deficit-Hyperactivity Disorder (ADHD), Autism, Autonomic Dysfunction, Back Pain, Barth Syndrome, Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain infarction, Brain ischemia, Brain Injury, Brown-Sequard Syndrome, Bulbospinal Muscular Atrophy, CADASIL, Canavan Disease, Carpal Tunnel Syndrome, Causalgia, Cavernomas, Cavernous Angioma, Cavernous Malformation, Central Cervical Cord Syndrome, Central Cord Syndrome, Central Pain Syndrome, Central Pontine Myelinolysis, Cephalic Disorders, Ceramidase Deficiency, Cerebellar Degeneration, Cerebellar Hypoplasia, Cerebral Aneurysm, Cerebral Arteriosclerosis, Cerebral Atrophy, Cerebral Beriberi, Cerebral Cavernous Malformation, Cerebral Gigantism, Cerebral Hypoxia, Cerebral Palsy, Cerebro-Oculo-Facio-Skeletal Syndrome, Charcot-Marie-Tooth Disease, Chiari Malformation, Cholesterol Ester Storage Disease, Chorea, Choreoacanthocytosis, Chronic Inflammatory Demyelinating Polyneuropathy (CIDP), Chronic Orthostatic Intolerance, Chronic Pain, Cockayne Syndrome Type II, Coffin Lowry Syndrome, COFS, Colpocephaly, Coma, Complex Regional Pain Syndrome, Congenital Facial Diplegia, Congenital Myasthenia, Congenital Myopathy, Congenital Vascular Cavernous Malformations, Corticobasal Degeneration, Cranial Arteritis, Craniosynostosis, Creutzfeldt-Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia—Multi-Infarct, Dementia—Semantic, Dementia—Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dravet Syndrome, Dysautonomia, Dysgraphia, Dyslexia, Dysphagia, Dyspraxia, Dyssynergia Cerebellaris Myoclonica, Dyssynergia Cerebellaris Progressiva, Dystonias, Early Infantile Epileptic Encephalopathy, Empty Sella Syndrome, Encephalitis, Encephalitis Lethargica, Encephaloceles, Encephalopathy, Encephalopathy, familial infantile, with intracranial calcification and chronic cerebrospinal fluid lymphocytosis; Cree encephalitis; Pseudo-Torch syndrome; Pseudotoxoplasmosis syndrome, Encephalotrigeminal Angiomatosis, Epilepsy, Epileptic Hemiplegia, Erb-Duchenne and Dejerine-Klumpke Palsies, Erb's Palsy, Essential Tremor, Extrapontine Myelinolysis, Fabry Disease, Fahr's Syndrome, Fainting, Familial Dysautonomia, Familial Hemangioma, Familial Idiopathic Basal Ganglia Calcification, Familial Periodic Paralyses, Familial Spastic Paralysis, Farber's Disease, Febrile Seizures, Fibromuscular Dysplasia, Fisher Syndrome, Floppy Infant Syndrome, Foot Drop, Friedreich's Ataxia, Frontotemporal Dementia, Gangliosidoses, Gaucher's Disease, Gerstmann's Syndrome, Gerstmann-Straussler-Scheinker Disease, Giant Axonal Neuropathy, Giant Cell Arteritis, Giant Cell Inclusion Disease, Globoid Cell Leukodystrophy, Glossopharyngeal Neuralgia, Glycogen Storage Disease, Guillain-Barré Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica Polyneuritiformis, Herpes Zoster, Herpes Zoster Oticus, Hirayama Syndrome, Holmes-Adie syndrome, Holoprosencephaly, HTLV-1 Associated Myelopathy, Hughes Syndrome, Huntington's Disease, Hydranencephaly, Hydrocephalus, Hydrocephalus—Normal Pressure, Hydromyelia, Hypercortisolism, Hypersomnia, Hypertonia, Hypotonia, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathies, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Kluver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lipoid Proteinosis, Lissencephaly, Locked-In Syndrome, Lou Gehrig's Disease, Lupus—Neurological Sequelae, Lyme Disease—Neurological Complications, Machado-Joseph Disease, Macrencephaly, Megalencephaly, Melkersson-Rosenthal Syndrome, Meningitis, Meningitis and Encephalitis, Menkes Disease, Meralgia Paresthetica, Metachromatic Leukodystrophy, Microcephaly, Migraine, Miller Fisher Syndrome, Mild Cognitive Impairment, Mini-Strokes, Mitochondrial Myopathies, Moebius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy, Congenital Myopathy, Thyrotoxic Myopathy, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid Lipofuscinosis, Neuronal Migration Disorders, Neuropathy—Hereditary, Neurosarcoidosis, Neurotoxicity, Nevus Cavernosus, Niemann-Pick Disease, Normal Pressure Hydrocephalus, Occipital Neuralgia, Ohtahara Syndrome, Olivopontocerebellar Atrophy, Opsoclonus Myoclonus, Orthostatic Hypotension, O'Sullivan-McLeod Syndrome, Overuse Syndrome, Pain—Chronic, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal Leukoencephalopathy, Progressive Sclerosing Poliodystrophy, Progressive Supranuclear Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated Myelopathy, Rett Syndrome, Reye's Syndrome, Rheumatic Encephalitis, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Severe Myoclonic Epilepsy of Infancy (SMEI), Shaken Baby Syndrome, Shingles, Shy-Drager Syndrome, Sjögren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar Degeneration, Steele-Richardson-Olszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache, Swallowing Disorders, Sydenham Chorea, Syncope, Syphilitic Spinal Sclerosis, Syringohydromyelia, Syringomyelia, Systemic Lupus Erythematosus, Tabes Dorsalis, Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Troyer Syndrome, Tuberous Sclerosis, Vascular Erectile Tumor, Vasculitis Syndromes of the Central and Peripheral Nervous Systems, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, Wolman's Disease, X-Linked Spinal and Bulbar Muscular Atrophy, Zellweger Syndrome, optic neuritis, Chronic fatigue syndrome, fibromyalgia, psychiatric diseases such as mood disorders, major depression, bipolar syndrome, psychosis, schizophrenia, obsessive-compulsive-syndrome, toxic or drug abuse diseases such as alcoholism and drug abuse, and encephalopathy such as hepatic encephalopathy.

Hence, p97-siRNA conjugates directed to NOX genes (e.g., NOX1, NOX2, NOX4), and which have improved penetration of CNS tissues, could provide therapeutic utility in the treatment of these and other NOX-associated diseases or conditions of the CNS.

For in vivo use, for instance, for the treatment of human disease, medical imaging, or testing, the p97 conjugates described herein are generally incorporated into a pharmaceutical composition prior to administration. A pharmaceutical composition comprises one or more of the p97 conjugates described herein in combination with a physiologically acceptable carrier or excipient.

To prepare a pharmaceutical composition, an effective or desired amount of one or more conjugates is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

Administration of conjugates described herein, in pure form or in an appropriate pharmaceutical composition, can be carried out via any of the accepted modes of administration of agents for serving similar utilities. The pharmaceutical compositions can be prepared by combining a conjugate-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other small molecules as described elsewhere herein) and/or suitable excipients such as salts, buffers and stabilizers may, but need not, be present within the composition.

Administration may be achieved by a variety of different routes, including oral, parenteral, nasal, intravenous, intradermal, subcutaneous or topical. Preferred modes of administration depend upon the nature of the condition to be treated or prevented. Particular embodiments include administration by IV infusion.

Carriers can include, for example, pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In certain aspects, the p97 polypeptide sequence and the siRNA molecule(s) are each, individually or as a pre-existing conjugate, bound to or encapsulated within a particle, e.g., a nanoparticle, bead, lipid formulation, lipid particle, or liposome, e.g., immunoliposome. For instance, in particular embodiments, the p97 polypeptide sequence is bound to the surface of a particle, and the siRNA molecule of interest is bound to the surface of the particle and/or encapsulated within the particle. In some of these and related embodiments, the p97 polypeptide and the siRNA molecule(s) are covalently or operatively linked to each other only via the particle itself (e.g., nanoparticle, liposome), and are not covalently linked to each other in any other way; that is, they are bound individually to the same particle. In other embodiments, the p97 polypeptide and the siRNA molecule(s) are first covalently or non-covalently conjugated to each other, as described herein (e.g., via a linker molecule), and are then bound to or encapsulated within a particle (e.g., liposome, nanoparticle). In specific embodiments, the particle is a liposome, and the composition comprises one or more p97 polypeptides, one or more siRNA molecule(s) of interest, and a mixture of lipids to form a liposome (e.g., phospholipids, mixed lipid chains with surfactant properties). In some aspects, the p97 polypeptide and the siRNA molecule(s) are individually mixed with the lipid/liposome mixture, such that the formation of liposome structures operatively links the p97 polypeptide and the siRNA molecule(s) without the need for covalent conjugation. In other aspects, the p97 polypeptide and the siRNA molecule(s) are first covalently or non-covalently conjugated to each other, as described herein, and then mixed with lipids to form a liposome. The p97 polypeptide, the siRNA molecule(s), or the p97 conjugate may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents, such as cytotoxic agents.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described conjugate in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will typically contain a therapeutically effective amount of a conjugate described herein, for treatment of a disease or condition of interest.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a conjugate such that a suitable dosage will be obtained. Typically, this amount is at least 0.01% of the agent of interest in the composition. When intended for oral administration, this amount may be varied to be between 0.1 and about 70% of the weight of the composition. Certain oral pharmaceutical compositions contain between about 4% and about 75% of the agent of interest. In certain embodiments, pharmaceutical compositions and preparations according to the present invention are prepared so that a parenteral dosage unit contains between 0.01 to 10% by weight of the agent of interest prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the conjugate or agent and thereby assists in the delivery of the compound. Suitable agents that may act in this capacity include monoclonal or polyclonal antibodies, one or more proteins or a liposome.

The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the conjugates against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the conjugate so as to facilitate dissolution or homogeneous suspension of the conjugate in the aqueous delivery system.

The compositions may be administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., ~0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g).

Compositions described herein may also be administered simultaneously with, prior to, or after administration of one or more other therapeutic agents, as described herein. For instance, in one embodiment, the conjugate is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Such combination therapy may include administration of a single pharmaceutical dosage formulation, which contains a compound of the invention (i.e., conjugate) and one or more additional active agents, as well as administration of compositions comprising conjugates of the invention and each active agent in its own separate pharmaceutical dosage formulation. For example, a conjugate as described herein and the other active agent can be administered to the patient together in a single oral dosage composition such as a tablet or capsule, or each agent administered in separate oral dosage formulations. Similarly, a conjugate as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising conjugates and one or more additional active agents can be administered at essentially the same time, i.e., concurrently, or at separately staggered times, i.e., sequentially and in any order; combination therapy is understood to include all these regimens.

The various embodiments described herein can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

EXAMPLES

Example 1

Preparation and Testing of p97-siRNA Conjugates

To test the ability of p97 to enhance delivery of siRNA molecules across the blood brain barrier (BBB), the C-terminus of a p97 polypeptide DSSHAFTLDERYC (SEQ ID NO:29) was conjugated via a linker moiety to the 3' end of the antisense strand of an siRNA molecule targeted against the NOX4 gene (5'-A UGU UCA CAA AGU CAG GUC TT-3') (SEQ ID NO:31). For detection, the sense strand of the siRNA molecule (5'-GAC CUG ACU UUG UGA ACA UTT-3') (SEQ ID NO:32) was conjugated via a linker to Alexa Fluor® 680 (AF680). For the positive control, the p97-conjugated antisense and AF680-labeled sense strands were annealed to form the p97-siRNA conjugate (see FIG. 2A). For the negative control, an unconjugated antisense strand and the AF680-labeled sense strands were annealed (see FIG. 2B).

Test molecules were injected into mice, as outlined in the study design shown in Table E1 below.

TABLE E1

| Test Article | Route[1] | Time point (h) | Dose level[2] (mg/kg) | Vascular Perfusion[3] | Number of Mice[4] |
|---|---|---|---|---|---|
| PBS | IV | 1 | N/A | N/A | 1 |
| siRNA$^{AF680}$ | IV | 1 | 10.0 | Yes | 3 |
| p97-siRNA$^{AF680}$ | IV | 1 | 10.0 | Yes | 3 |

Figure 3:
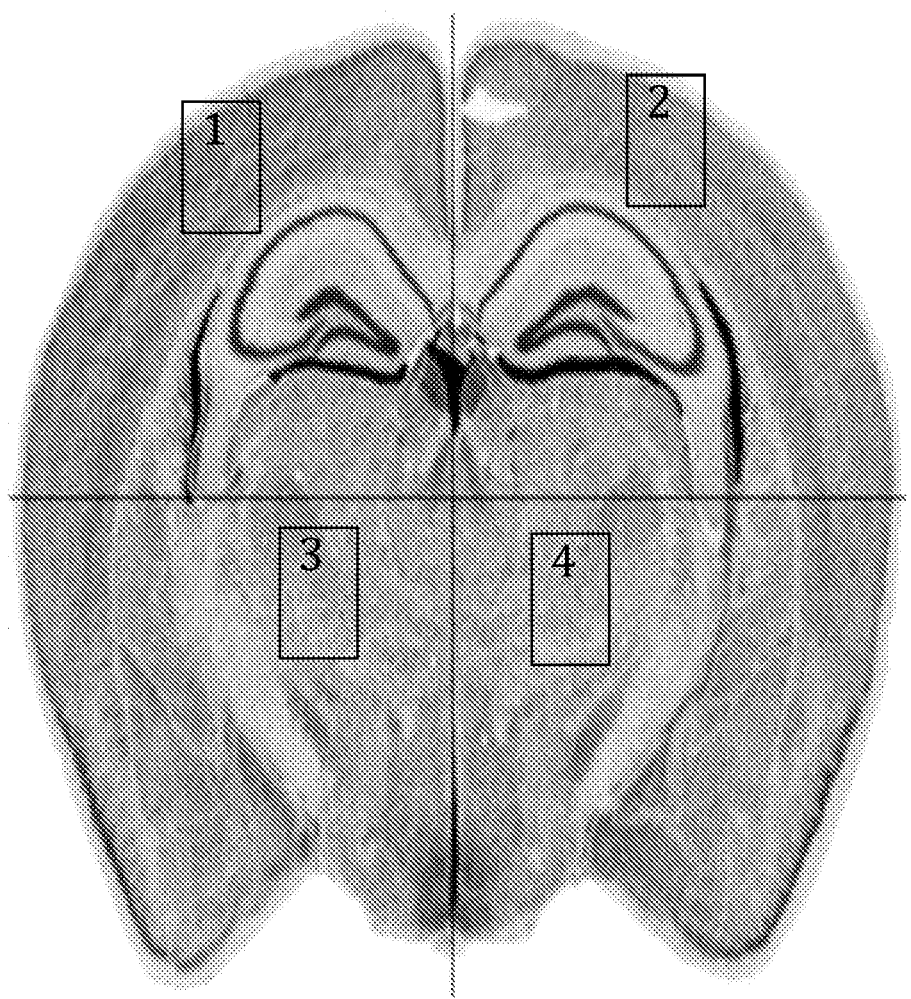
FIG. 3 shows the location of the four fields of view in the brain sections analyzed (see Example 1).

[1]Injection route = IV—intravenous via tail vein
[2]Injection volume = 5 ml/g (~0.1 ml per mouse)
[3]Vascular Perfusion = 10 mins@1 ml/min with PBS pH 7.4 with 2.7% BSA, 100 U/ml heparin
[4]Mouse Strain BALB/c female 6 weeks old, 16-20 g
Test molecules were provided in powder form and re-constituted in Nuclease-free PBS, pH 7.4 at 2 mg/ml Test molecules were intravenously injected (via tail vein) in Balb/c mice and 1 hour later the animals were sacrificed as follows: Prior to euthanasia, mice were injected (i.v.) with tomato Lectin-Texas Red (80 mg) for 10 min to stain the brain vasculature. Blood was cleared by intracardiac perfusion of 10 ml heparinized saline (1 ml/min). Brains were excised and frozen on dry ice and stored at −80° C. Brains were mounted in Tissue Tek and sectioned (25 mm, 3 sections/brain) with a cryostat at −2° C. Sections (n=3/brain) were mounted on Superfrost Plus microscope slides, fixed in cold Acetone/MeOH (1:1) for 10 min at RT, and then washed with PBS. Glass coverslips were mounted on sections using Prolong Gold antifade reagent with DAPI (Molecular probes, P36931). 3D confocal microscopy was performed (4 random fields per section were captured). FIG. 3 shows the location of the four fields of view in the brain sections.

Figure 4:
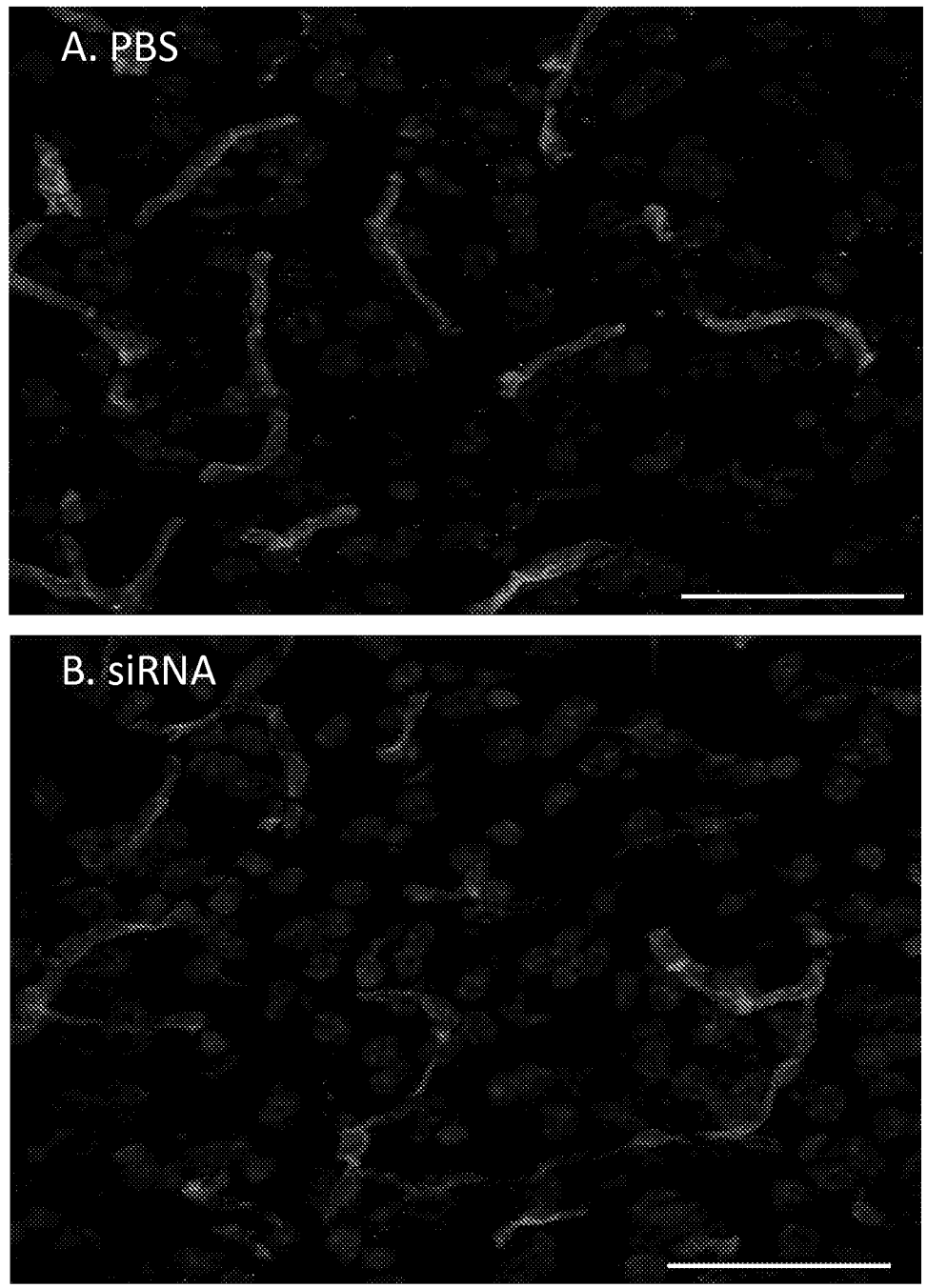
FIGS. 4A-4D show immunofluorescence imaging of mice brain tissues following intravenous administration of test agents. Control test agents PBS only (4A) and unconjugated siRNA (4B) show no AF680 (red) staining in brain tissues. In contrast, p97-siRNA conjugates (4C-4D) show significant AF680 (red) staining in brain tissues, evidencing that conjugation to p97 polypeptides can enhance delivery of siRNA molecules into CNS tissues such as the brain parenchyma.
Figure 4:
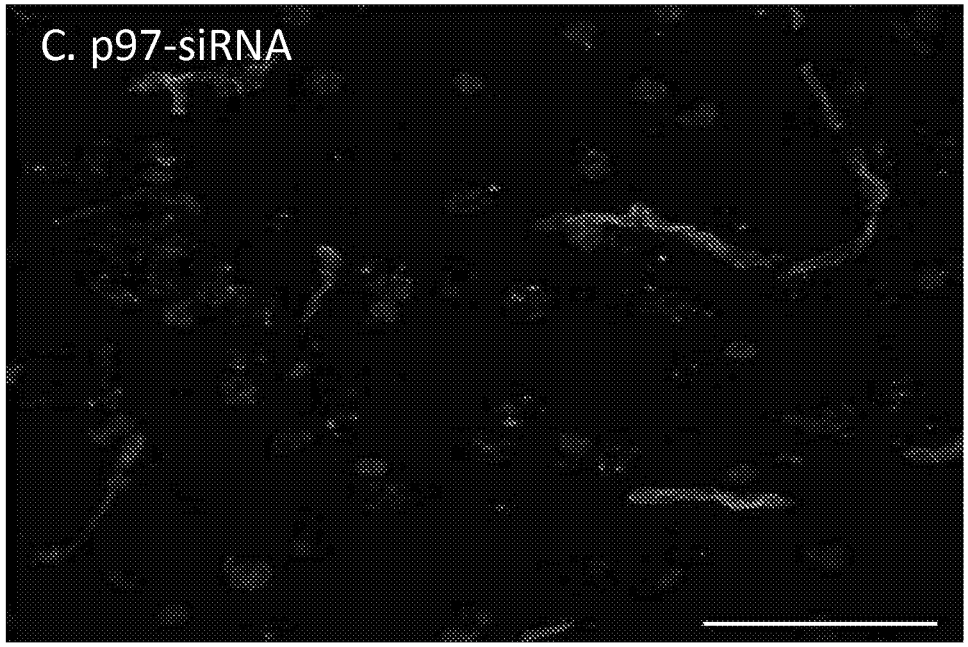
Figure 4:
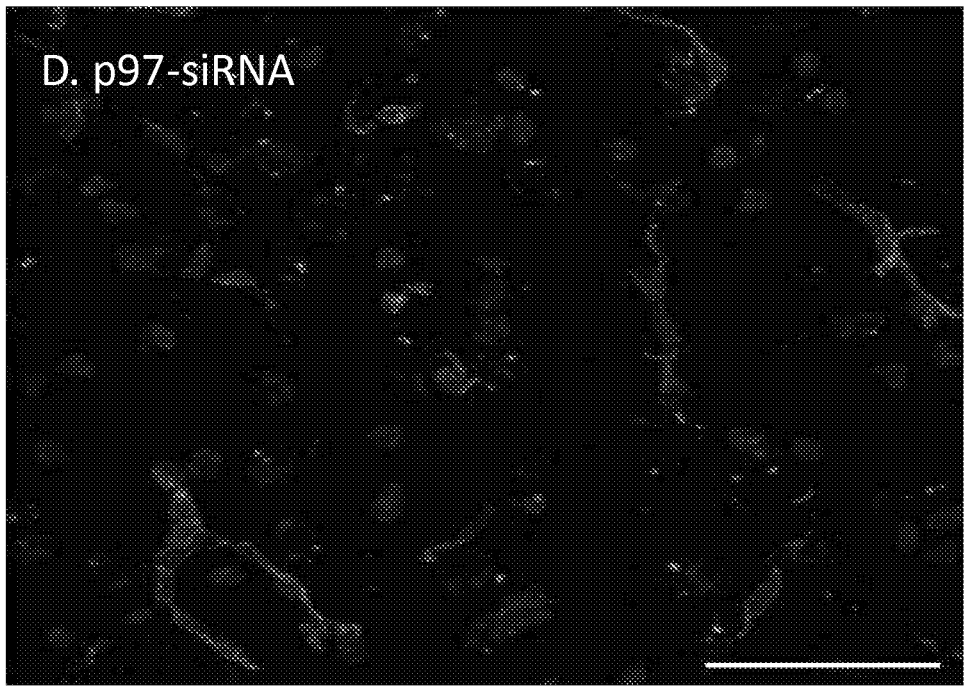
Figure 7:
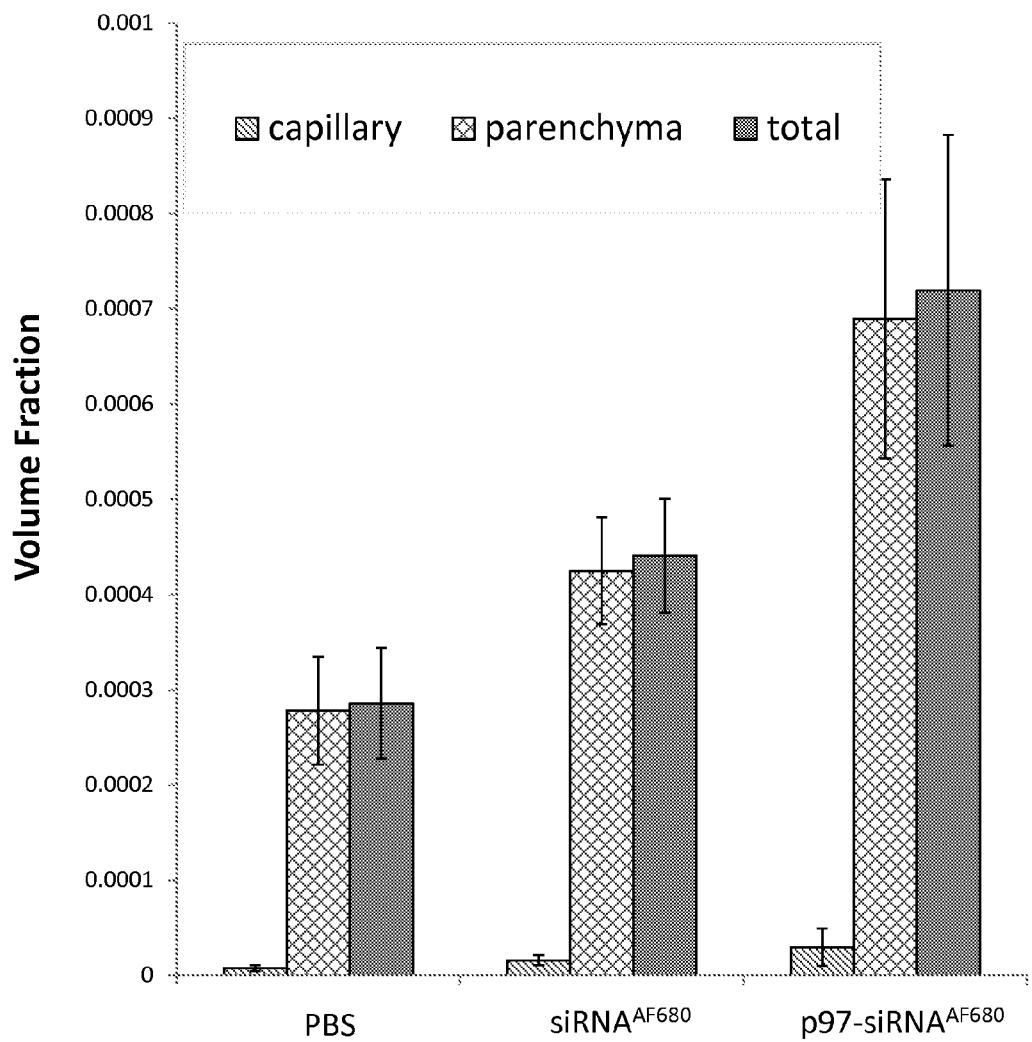
FIG. 7 shows the volume fractions of the siRNA and p97-siRNA conjugate in brain tissues relative to the PBS control.

Signals for all the sections were calibrated with respect to the PBS control group in order to observe only minimal (but not completely null) AF680 fluorescent signal in those sections (see FIG. 4A). For siRNA$^{AF680}$ perinuclear AF680 signal was not detected in the brain parenchyma of any mice (see FIG. 4B) and no AF680 signal was observed in the vasculature. For p97-siRNA$^{AF680}$ perinuclear AF680 signal was detected in the brain parenchyma of all mice (see FIG. 4D), and no AF680 signal was observed in the vasculature. FIG. 7 shows the calculated volume fractions of the siRNA$^{AF680}$ and the p97-siRNA$^{AF680}$ conjugate in brain tissues relative to the PBS control. These results show that conjugation to p97 polypeptides can significantly enhance delivery of siRNA molecules into CNS tissues such as the brain parenchyma.

To measure mRNA levels of NOX4, mice were injected (as above) with a low dose of test molecules (10 mg/kg), and tissue samples were collected for analysis one hour after injection. Total RNA was extracted from frozen brain tissues (see TRIzol® reagents and methods) and real-time PCR was performed on the RNA samples using the primers in Table E2 below.

TABLE E2

| Name | Sequence | SEQ ID NO: |
|---|---|---|
| GAPDH-Fwd | AACTTTGGCATTGTGGAAGG | 56 |
| GAPDH-Rvs | ACACATTGGGGGTAGGAACA | 57 |
| NOX4-Fwd | GCCTTTATTGTGCGGAGAGA | 58 |
| NOX4-Rvs | CTTGACTTGATGGAGGCAGTAG | 59 |

For real-time PCR, 1 μg of each RNA sample was reverse transcribed to cDNA with qScript cDMA SuperMix agent (QuantaBio) using random hexamers and oligo dT. Real-time RT-PCR was then performed using SYBR Green I technology on ABI 7500 FAST REAL TIME PCR System (Applied Biosystems, Foster city, USA). A master mix for each PCR run was prepared with SYBR Green PCR Core Reagents (Applied Biosystems, Foster City, USA) containing: 1×SYBR Green PCR Buffer, 3 mM MgCl2, 1 mM dNTP, 0.625 U Taq polymerase, and 0.25 U Amperase UNG. 10 ng of cDNA were added, and 300 nM each for specific sense and anti-sense primers were used.

Amplification program for Real-time PCR was as follows: 50° C. 2 min, 95° C. 10 min, 40 cycles at 95° C. for 15 s followed by 60° C. for 1 min. All samples were amplified in triplicate from the same RNA preparation and the mean value was considered. The real-time PCR efficiency was determined for each gene and each stress with the slope of a linear regression model. For this, each cDNA sample was bulked and then used as the PCR template in a range of 50, 25, 10, 5, and 2 ng. For each gene, PCR efficiency was determined by measuring the CT to a specific threshold (Walker, 2002) for a serial dilution of bulked cDNA. All PCR reactions displayed efficiencies between 84% and 96%.

Figure 8:
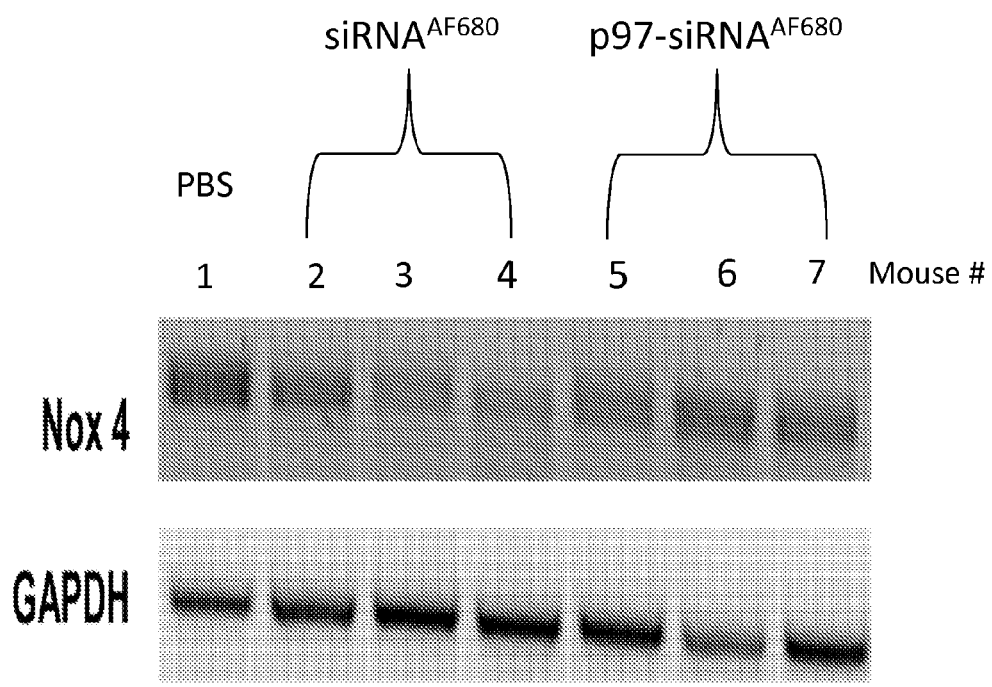
FIG. 8 shows the RT-PCR results for the seven different mice tested (one PBS control and three for each siRNA test molecule, as indicated). Levels of NOX4 mRNA are shown relative to GAPDH control.

The data are shown in FIGS. 8 and 9A-9C. FIG. 8 shows the RT-PCR results for the seven different mice tested (one PBS control and three for each siRNA test molecule). Levels of NOX4 mRNA are shown relative to GAPDH control.

Figure 9A:
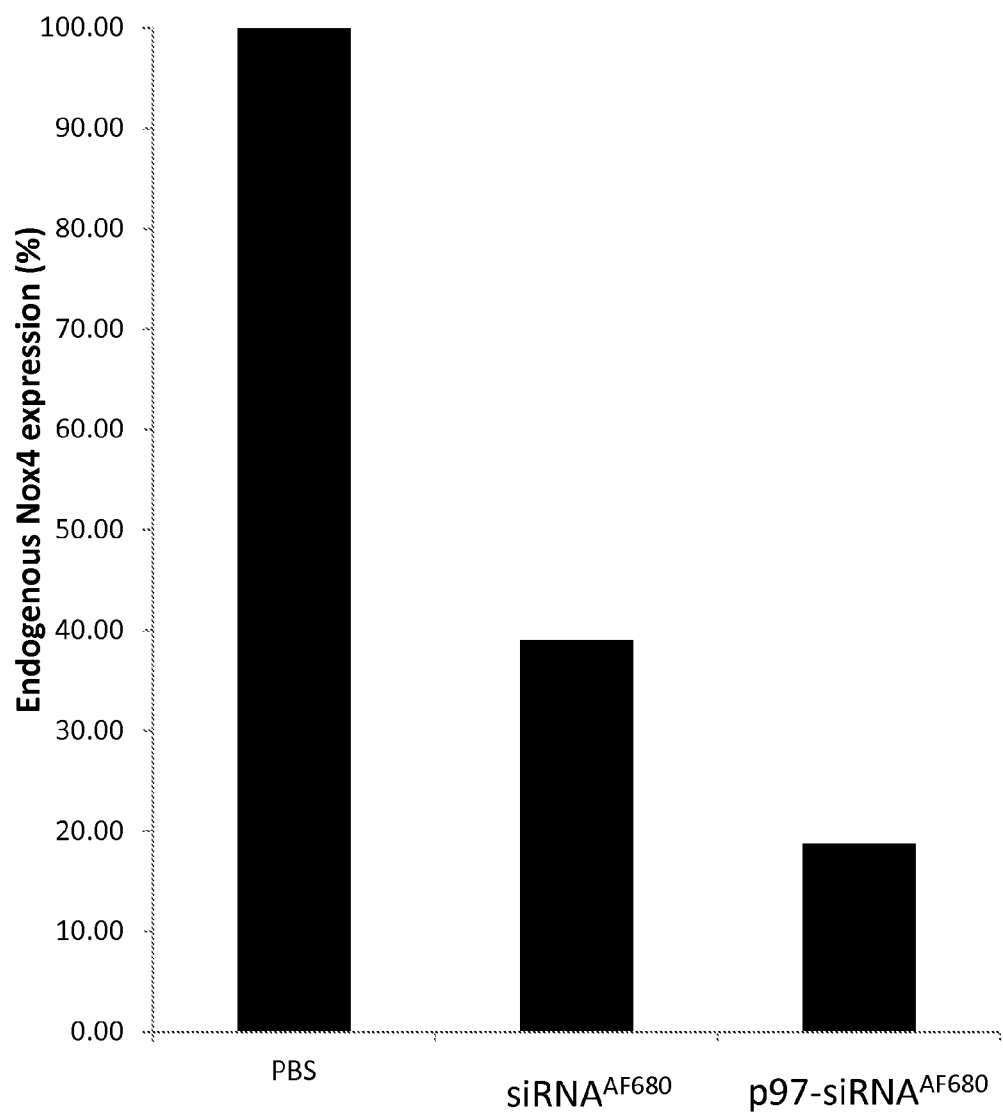
FIGS. 9A-9C show the RT-PCR data analyzed using the $\Delta\Delta CT$ method: =(CT(target, untreated)−CT(ref, untreated))−(CT(target, treated)−CT(ref, treated)).
Figure 9B:
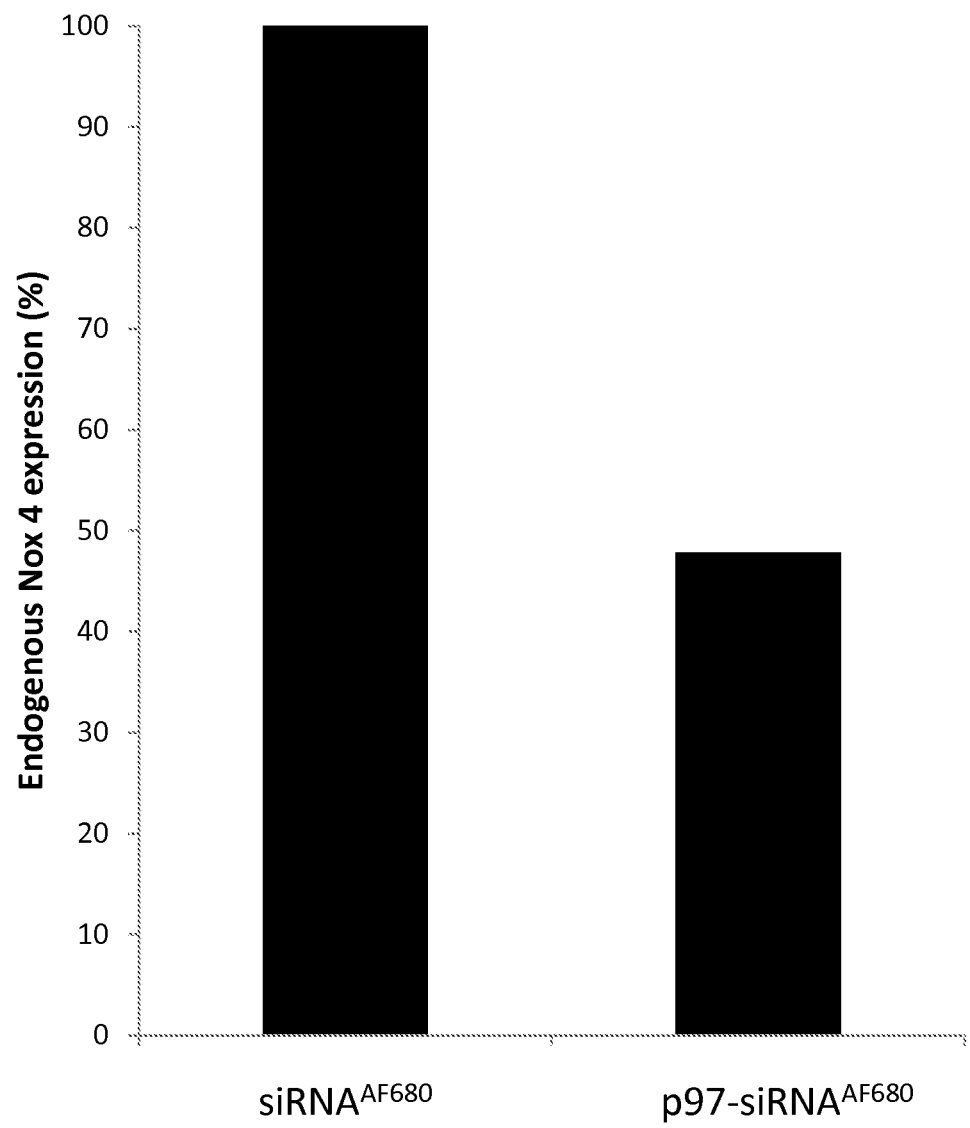
Figure 9C:
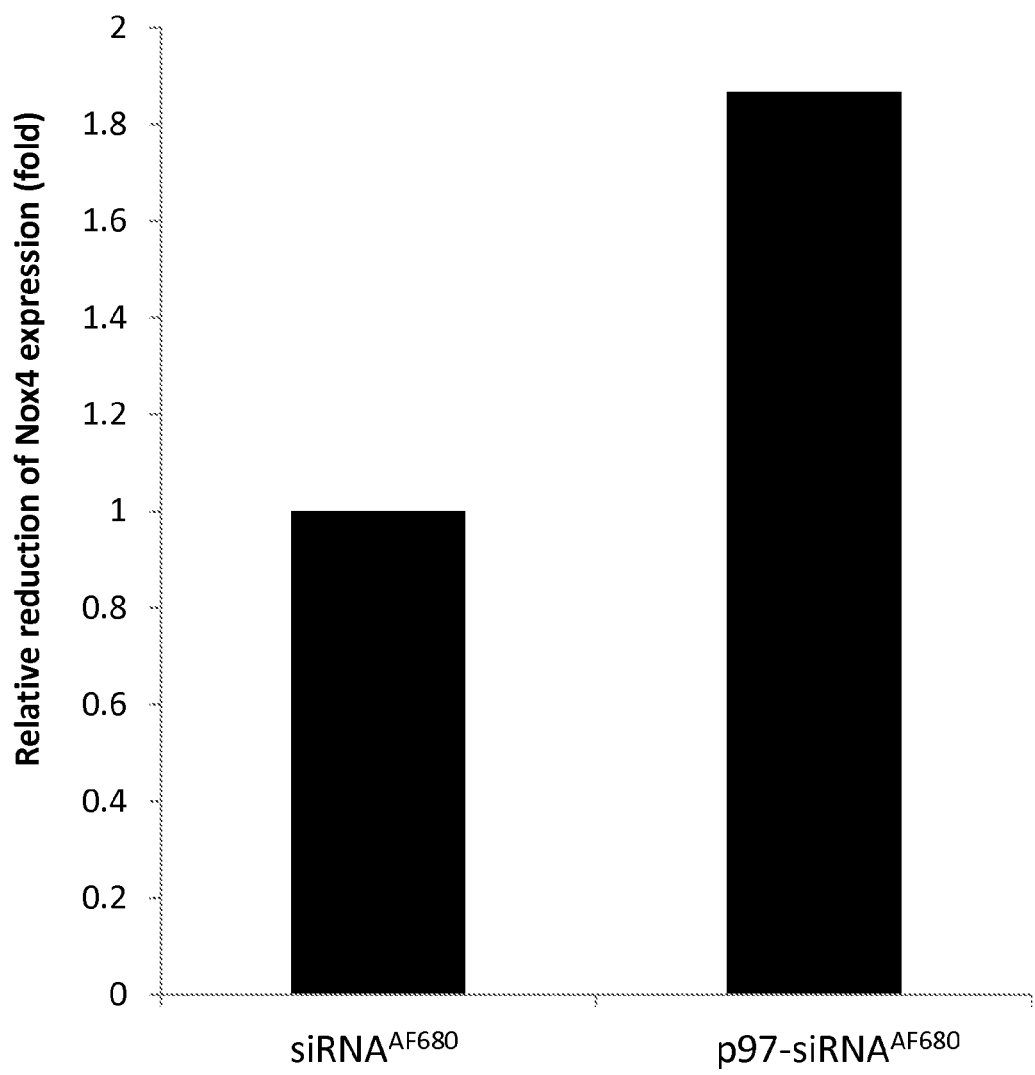

FIGS. 9A-9C show the data analyzed using the ΔΔCT method: =(CT(target, untreated)−CT(ref, untreated))−(CT(target, treated)−CT(ref, treated)). FIG. 9A shows that NOX4 mRNA is significantly down-regulated in brain tissues from mice treated with p97-siRNA conjugate relative to controls (PBS and unconjugated siRNA). FIG. 9B shows the percentage reduction in endogenous NOX4 expression in brain tissues from mice treated with p97-siRNA conjugate relative to unconjugated siRNA. FIG. 9C shows the fold-reduction (~1.8-fold) in NOX4 expression in brain tissues from mice treated with p97-siRNA conjugate relative to unconjugated siRNA.

These data show that conjugation of siRNA (against NOX4 gene) to a p97 peptide was able to facilitate higher transport across the BBB into brain parenchyma. Also, quantification of the mRNA specific to the NOX4 gene by RT-PCR demonstrated a higher down-regulation of NOX4 after treatment with p97-siRNA conjugate relative to unconjugated siRNA.

Example 2

Effect of p97-siRNA Conjugates Ischemic-Induced Stroke Mice Model

The NOX4 gene-targeted p97-siRNA conjugates from Example 1 were tested for their ability to provide neuroprotection in a mouse model of middle cerebral artery occlusion (MCAO) (see, e.g., Chang et al., J Vis Exp. 2761:2011; Althenhöfer et al., Cell. Mol. Life Sci. 69:2327-2343, 2012; and Kleinschnitz et al., PLoS Biol. 8(9): e1000479, 2010).

C57/Bl6 mice were pretreated 3 times (1 hour interval between each injection) with either PBS or 30 mg/kg of siRNA alone or p97-siRNA via intravenous (IV) injection. Animals were subjected to stroke via MCAO about 1 hour following the last injection, as follows. The external and internal carotid arteries (ECA and ICA, respectively) were dissected and isolated and the common carotid artery (CCA) ligated. An 11 cm 8-0 nylon thread coated in dental silicone was inserted into a small hole in the ECA towards the bifurcation of the CCA. The thread was gently introduced into the ICA and fed until only 1 mm is protruding from the hole. The thread passes into the Circle of Willis and occludes the opening of the middle cerebral artery allowing no blood to pass. The thread was left in place for 1 hour and then removed and the ligature on the CCA removed allowing reperfusion of the affected brain area. Mice were sacrificed at 24 hours post reperfusion, and the brains dissected and removed for sample analysis.

Infarct Volume Analysis. To measure ischemic damage at 24 hours after 1 hour MCA occlusion, the brains were removed from euthanized animals, the cerebrum was cut into five 2-mm-thick coronal slices, which were stained with 2% 2,3,5-triphenyltetrazolium chloride (TTC). The brain slices were then cut in half to separate the ischemic hemisphere and the contralateral hemisphere. The ischemic and contralateral brain slices were transferred to separate vials containing 2% of TTC solution and continue to stain at 37° C. for 60 min. Images of the brain slices were obtained with a HP scanner after 10-15 min staining at RT.

When the TTC staining was completed, infarct size was measured by a colorimetric staining method. Briefly, the tissue was rinsed with saline and subsequently exposed to a mixture of ethanol/dimethyl sulfoxide (1:1) to solubilize the formazan product. After 24-hour incubation in the dark, the red solvent extracts were diluted 1:20 with fresh ethanol/dimethyl sulfoxide (1:1) solvent in three glass tubes and then transferred into cuvettes.

Absorbance was measured at 485 nm in a spectrophotometer and the values were averaged. Percentage loss in brain TIC staining in the ischemic side of the brain was compared with the contralateral side of the brain of the same animal using the following equation:

$$\% \text{ loss}=100\times(1-\text{absorbance of ischemic hemisphere}/\text{absorbance of contralateral hemisphere})$$

Figure 10:
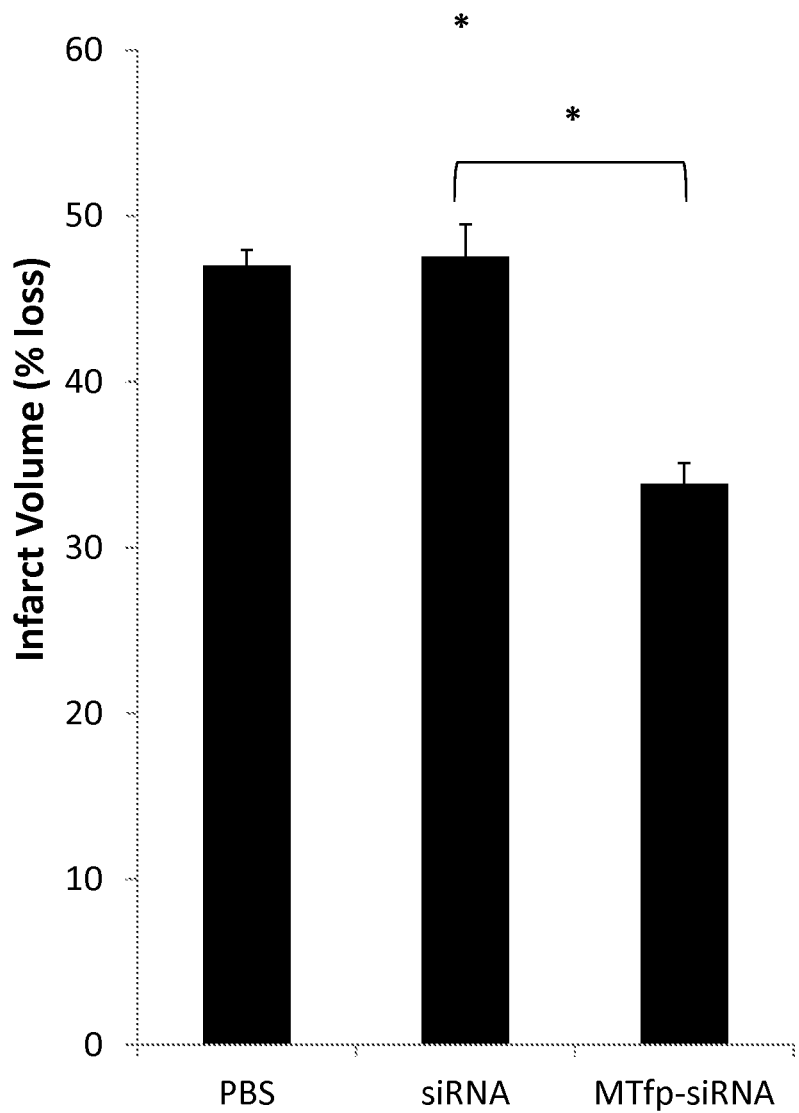
FIG. 10 shows that mice pretreated with p97-siRNA conjugate (MTfp-siRNA) and subject to ischemic stroke induction by middle cerebral artery occlusion (MCAO) had significantly smaller infarct areas relative to the PBS and siRNA-only groups.

No infarct tissue was observed in the brains of the sham group (no MCAO), and both PBS and siRNA treated stroked animals (MCAO) exhibited large infarct areas relative to the sham group. However, as shown in FIG. 10, animals treated with p97-siRNA conjugate (MTfp-siRNA) had significantly smaller infarct areas relative to the PBS and siRNA-only groups. Thus, pretreatment with p97-siRNA conjugates targeted against NOX4 provided neuroprotection in this mouse model of MCAO-induced stroke by significantly reducing the infarct volume in the brain.

Neurological Assessment. Behavioral assessments were performed at 0 and 24 hour after reperfusion by an individual blinded to the treatment of the mice.

The neurological deficits were scored as follows:
normal;
mild turning behavior with or without inconsistent curling when picked up by tail, <50% attempts to curl to the contralateral side;
mild consistent curling, >50% attempts to curl to contralateral side;
strong and immediate consistent curling, mouse holds curled position for more than 1-2 s, the nose of the mouse almost reaches tail;
severe curling progressing into barreling, loss of walking or righting reflex; and
comatose or moribund.

Figure 11:
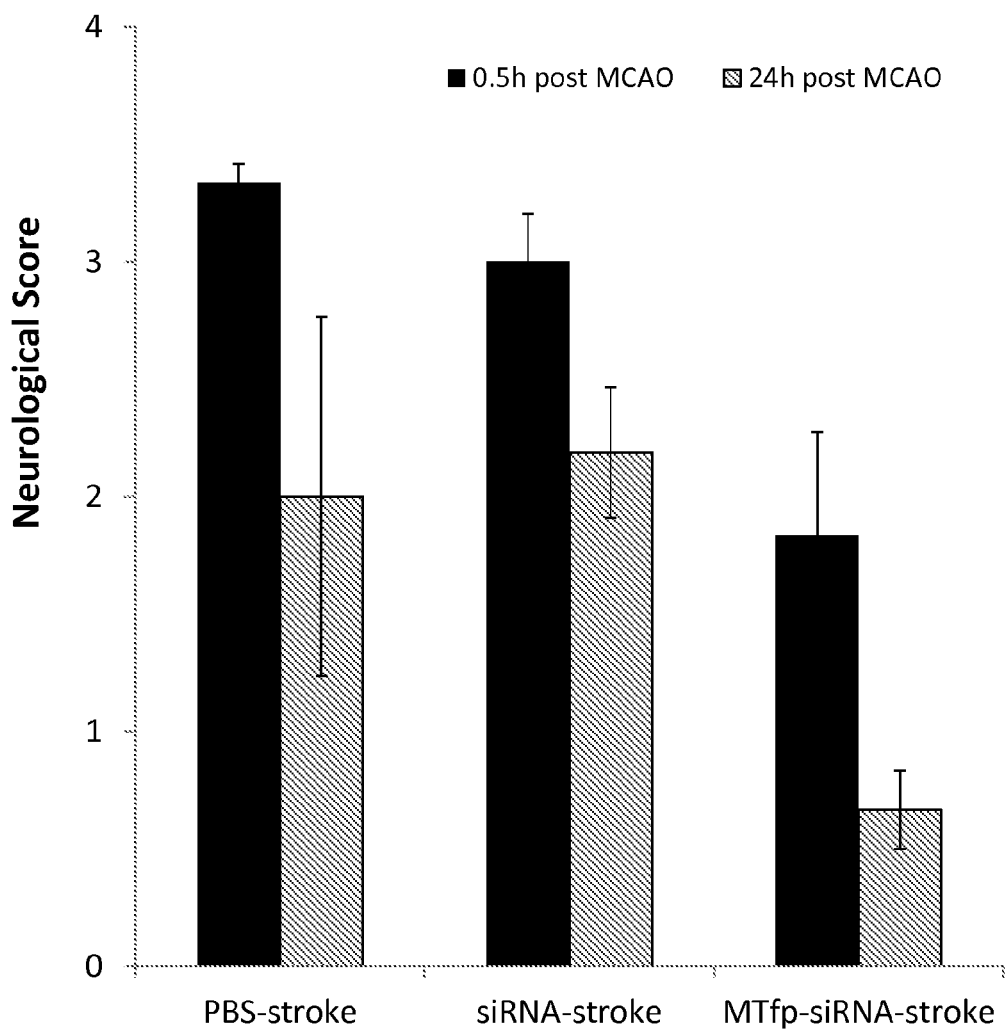
FIG. 11 shows that pretreatment with MTfp-siRNA conjugates improved the neurological deficit in the animals at 0.5 hours post-stroke induction relative to pretreatment with PBS or siRNA-only.

As shown in FIG. 11, pretreatment with MTfp-siRNA conjugates improved the neurological deficit in the animals at 0.5 hours post-stroke induction relative to pretreatment with PBS or siRNA-only.

Figure 12A:
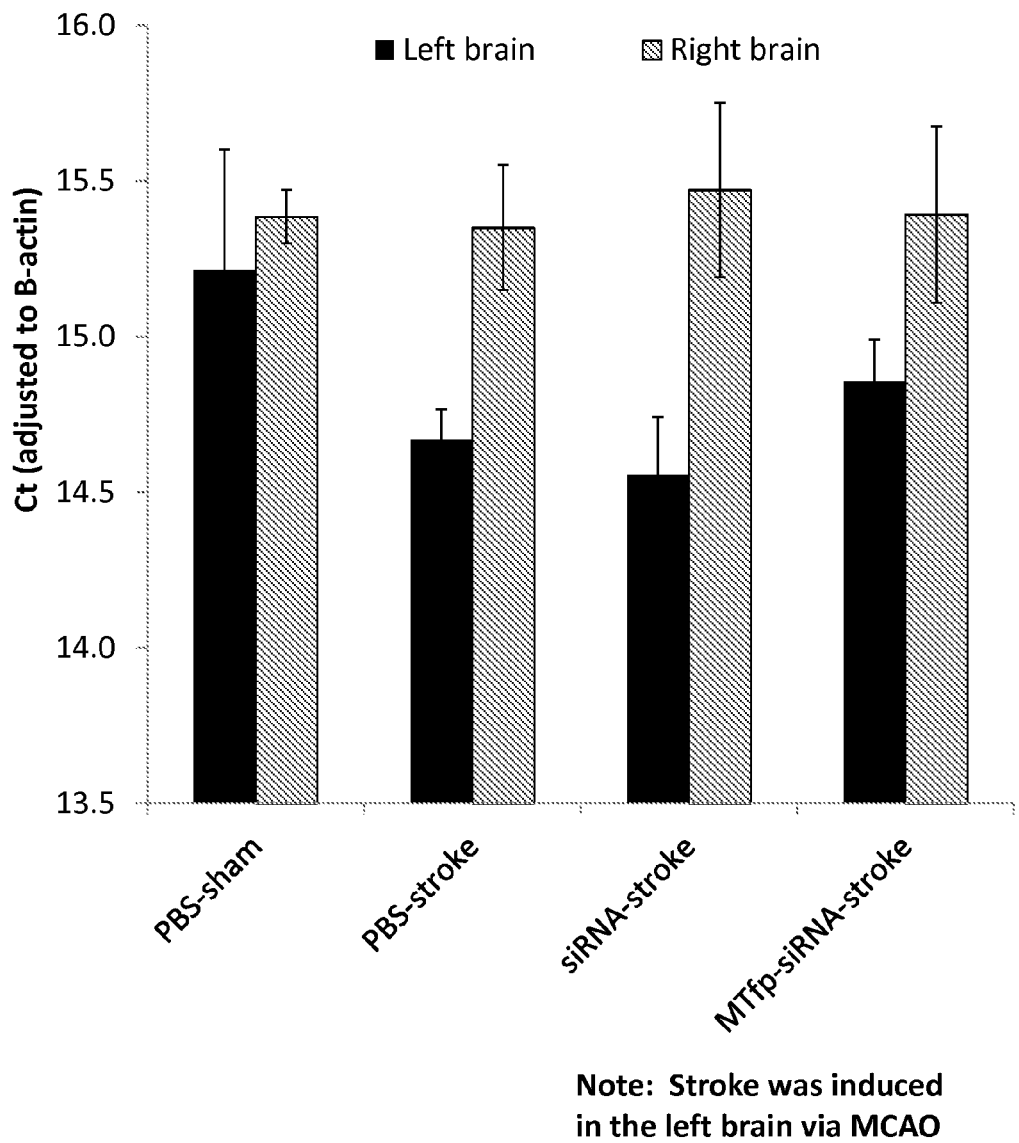
FIGS. 12A-12B show the results of RT-PCR analysis of NOX4 mRNA levels following pretreatment and stroke induction.

NOX4 mRNA Expression. Real-time PCR was performed to analyze mRNA levels of NOX4 following pretreatment and stroke induction by MCAO. FIG. 12A shows that MTfp-siRNA pretreatment led to lower Nox4 induction in the stroke-induced portion of the brain relative to PBS or siRNA-only. Ct (cycle threshold; ΔCt=Ct(nox4, PBS-sham)−Ct(B-actin, PBS-sham) represents the number of cycles required for the fluorescent signal to cross the threshold/exceed background level, and is inversely proportional to the amount of target nucleic acid in the sample (i.e., the lower the Ct level the greater the amount of target nucleic acid in the sample).

Figure 12B:
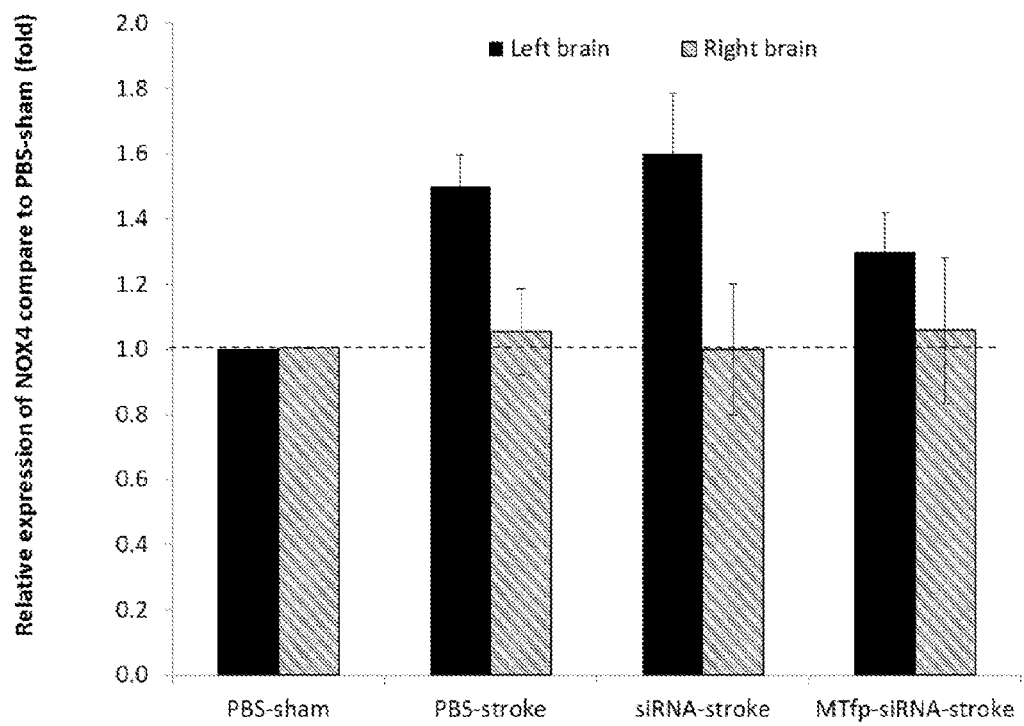

FIG. 12B shows that MTfp-siRNA pretreatment reduced NOX4 mRNA expression in the stroke-induced brain relative to PBS or siRNA-only. These results were analyzed using the ΔΔCT method (ΔΔCT=(CT(Nox4,PBS-sham)−CT(B-actin, PBS-sham))−(CT(Nox4, MTfp-siRNA-stroke)−CT(B-actin, MTfp-siRNA-stroke)).

In summary, p97 (MTfp) facilitated the transport of siRNA (targeting NOX4 gene) across the BBB into the brain. Also, pretreatment with MTfp-siRNA significantly reduced the infarct volume 24 hours after ischemic induction of stroke via MCAO. The smaller infract areas correlated with better neurologic scores in mice injected with MTfp-siRNA prior to induction of stroke. Specifically, pretreatment with MTfp-siRNA improved the neurological deficit in mice at both 0.5 hours and 24 hours post stroke induction relative to pretreatment with PBS or siRNA-only. MTfp-siRNA pretreatment also reduced Nox4 expression at the mRNA level relative to PBS or siRNA-only controls in the stroke-induced brain (left brain).

Thus, these data show that that siRNA can be delivered to the brain at a therapeutic dose after conjugation to p97 polypeptides such as MTfp.

The invention claimed is:

1. A composition comprising a p97 conjugate and a pharmaceutically acceptable carrier, where the conjugate comprises at least one isolated p97 polypeptide of up to 50 amino acids in length, where the polypeptide comprises an amino acid sequence at least 80% identical to DSSHAFTLDELR (SEQ ID NO:14), and where the p97 polypeptide is covalently linked to a) a first polynucleotide of about 15-40 nucleotides in length with or without a linker (L) in between, and (b) a second polynucleotide of about 15-40 nucleotides in length which is complementary to and hybridized to the first polynucleotide, where the first or second polynucleotide is an antisense strand that is complementary to a target mRNA sequence of a human NOX4 gene.

2. The composition of claim 1, where the first and second polynucleotides form 1-3 nucleotide overhang(s) at the 3' end of the antisense strand, the 5' end of the anti-sense strand, or both.

3. The composition of claim 1, where the first polynucleotide is the antisense strand and the second polynucleotide is a sense strand.

4. The composition of claim 1, where the second polynucleotide is the antisense strand and the first polynucleotide is a sense strand.

5. The composition of claim 1, where the first and second polynucleotides are selected from 5'-A UGU UCA CAA AGU CAG GUC TT-3' (SEQ ID NO:31) and 5'-GAC CUG ACU UUG UGA ACA UTT-3' (SEQ ID NO:32).

6. The composition of claim 1, where the first and second polynucleotide strands are CRISPR (clustered regularly interspaced short palindromic repeats) RNA oligonucleotides or small interfering RNAs.

7. The composition of claim 1, where the p97 polypeptide consists of DSSHAFTLDELR (SEQ ID NO: 14), DSSHAFTLDELRYC (SEQ ID NO:29) or DSSHAFTLDELRC (SEQ ID NO:30).

8. The composition of claim 1, where the p97 polypeptide comprises a cysteine residue at the C-terminus, the N-terminus, or both.

9. The composition of claim 1, comprising the linker (L) in between.

10. A pharmaceutical composition comprising the composition of claim 1, where the pharmaceutical composition is sterile and non-pyrogenic.

11. A method for the treatment of a NOX4-associated disease or condition of the CNS in a subject in need thereof, comprising administering to the subject the composition of claim 1 or the pharmaceutical composition of claim 10 and where the disease or condition is a stroke, ischemia, CNS trauma, or neuropathic pain.

12. The method of claim 11, where the composition of claim 1 is administered by intravenous (IV) infusion or subcutaneous injection.

13. The method of claim 11, where the pharmaceutical composition of claim 10 is administered by intravenous (IV) infusion or subcutaneous injection.

* * * * *